US009605057B1

(12) United States Patent
Scherer et al.

(10) Patent No.: US 9,605,057 B1
(45) Date of Patent: Mar. 28, 2017

(54) ENDOTROPHIN NEUTRALIZATION AND USE THEREOF

(71) Applicant: Board of Regents of The University of Texas System, Austin, TX (US)

(72) Inventors: Philipp Erich Scherer, Southlake, TX (US); Jiyoung Park, Dallas, TX (US); Zhiqiang An, Pearland, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 54 days.

(21) Appl. No.: 14/306,784

(22) Filed: Jun. 17, 2014

Related U.S. Application Data

(60) Provisional application No. 61/956,807, filed on Jun. 17, 2013.

(51) Int. Cl.
| | | |
|---|---|---|
| *A61K 39/395* | (2006.01) | |
| *C07K 16/00* | (2006.01) | |
| *C07K 16/18* | (2006.01) | |
| *A61K 33/24* | (2006.01) | |
| *A61K 49/00* | (2006.01) | |
| *A61K 45/06* | (2006.01) | |
| *A61K 39/00* | (2006.01) | |

(52) U.S. Cl.
CPC ............ *C07K 16/18* (2013.01); *A61K 33/24* (2013.01); *A61K 39/3955* (2013.01); *A61K 45/06* (2013.01); *A61K 49/0004* (2013.01); *A61K 2039/505* (2013.01)

(58) Field of Classification Search
None
See application file for complete search history.

(56) References Cited

U.S. PATENT DOCUMENTS

| | | | | |
|---|---|---|---|---|
| 7,374,762 B2 * | 5/2008 | Amphlett | ......... | A61K 47/48384 424/184.1 |
| 2004/0235840 A1 * | 11/2004 | Chari | ............... | A61K 47/48384 514/229.5 |

OTHER PUBLICATIONS

Iyengar et al. Adipocyte-derived collagen VI affects early mammary tumor progression in vivo, demonstrating a critical interaction in the tumor/stroma microenvironment. J Clin Invest. 2005; 115:1163-1176.*
Park et al. Endotrophin—Linking Obesity with Aggressive Tumor Growth. Oncotarget, December, vol. 3, No. 12, 1487-1488.*
Park et al. Adipocyte-derived endotrophin promotes malignant tumor progression. The Journal of Clinical Investigation. 122(111):4243-4256, Nov. 2012.*
Park, Jiyoung, Award No. W81XWH-09-1-0562, Collagen VI: A New Candidate Breast Cancer Marker Linked to Resistance to Platinum-Based Cancer Drugs. Accession No. ADA554275, Sep. 2011, pp. 1-16.*
Park, Jiyoung. Collagen VI: A New Candidate Breast Cancer Marker Linked to Resistance to Platinum-Based Cancer Drugs. Accession No. ADA544415. Sep. 2010, pp. 1-21.*
Owens RJ, Young RJ. The genetic engineering of monoclonal antibodies. J Immunol Methods. 168(2):149-165, 1994.*
Aigner et al. The C5 Domain of Col6A3 is Cleaved Off from the Col6 Fibrils Immediately after Secretion. Biochemical and Biophysical Research Communications 290, 743-748 (2002).*
Nanda et al. TEM8 Interacts with the Cleaved C5 Domain of Collagen α3(VI). Cancer Research 64, 817-820, Feb. 1, 2004.*
Dangi-Garimella et al., "Three-dimensional collagen I promotes gemcitabine resistance in pancreatic cancer through MT1-MMP-mediated expression of HMGA2", *Cancer Res*, 71: 1019-1028, 2011.
Jean et al., "Influence of stress on extracellular matrix and integrin biology", *Oncogene*, 30: 2697-2706, 2011,
Netti et al., "Role of extracellular matrix assembly in interstitial transport in solid tumors", *Cancer Res*, 60: 2497-2503, 2000.
Sherman-Baust et al., "Remodeling of the extracellular matrix through overexpression of collagen VI contributes to cisplatin resistance in ovarian cancer cells", *Cancer Cell*, 3: 377-386, 2003.

\* cited by examiner

*Primary Examiner* — Maher Haddad
(74) *Attorney, Agent, or Firm* — Parker Highlander PLLC

(57) ABSTRACT

Aspects of the present invention relate to methods and reagents for increasing chemosensitivity to platinum-based chemotherapy. In one aspect, a method of increasing chemosensitivity to platinum-based chemotherapy is provided, comprising administering to a patient in need thereof an effective amount of an endotrophin-neutralizing agent. The agent can be a monoclonal antibody, or fragment thereof, capable of binding to the C5 domain of the alpha3 chain of collagen VI. In some embodiments, the method can further include administering an effective amount of thiazolidinedione to said patient.

17 Claims, 43 Drawing Sheets
(43 of 43 Drawing Sheet(s) Filed in Color)

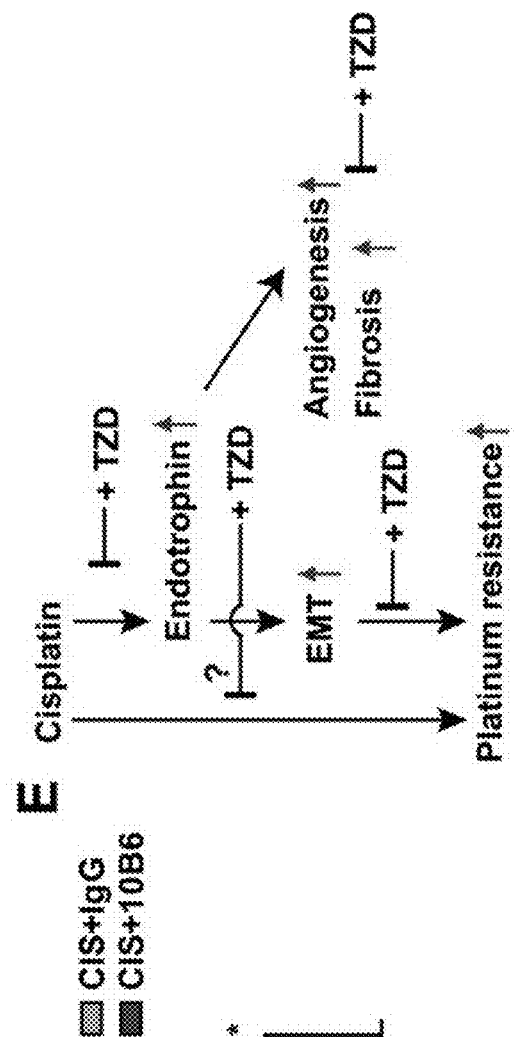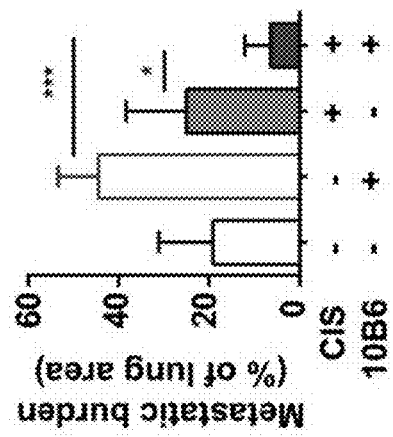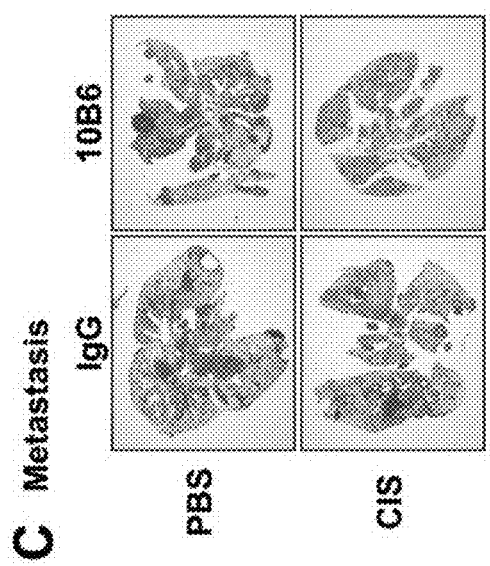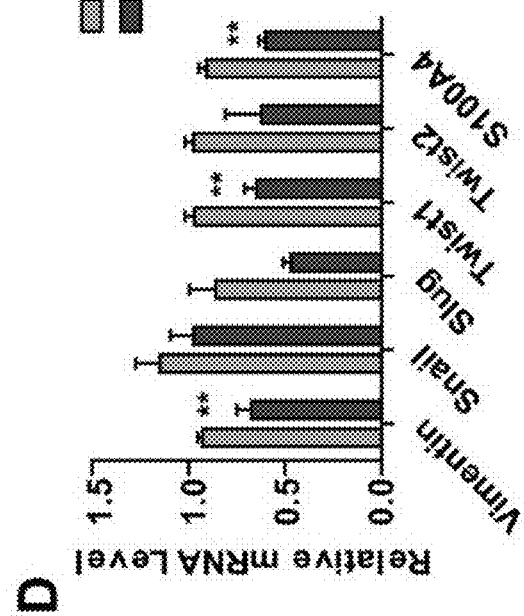
FIGS. 22C-22E

FIG. 28C

>10B6K (SEQ ID NO: 1)   318BP
GACGTCCAGTTGACCCAGTCTCCTTCATTCCTGTCTGCATCTGTGGGAGACAGAGTCACTATCAACTGCAAAGC
AAGTCAGAATATTAACAAGTACTTAAACTGGTATCAGCAAAAGCTTGGAGAAGCTCCCAAACGCCTGATATATA
ATACAAACAATTTGCAAACAGGCATCCCATCAAGGTTCAGTGGCAGTGGATCTGGTACAGATTACACACTCACC
ATCAGCAGCCTGCACCCTGAAGATTTTGCCACATATTTCTGCTTGCAGCATAGTAGTTTGTACACGTTTGGAGC
TGGGACCAAGCTGGAACTGAAA

>10B6K (SEQ ID NO: 2)   106AA
DVQLTQSPSFLSASVGDRVTINCKASQNINKYLNWYQQKLGEAPKRLIYNTNNLQTGIPSRFSGSASGTDYTLT
ISSLHPEDFATYFCLQHSSLYTFGAGTKLELK

| | FR1-IMGT | CDR1-IMGT | FR2-IMGT | CDR2-IMGT | FR3-IMGT | CDR3-IMGT | FR4-IMGT |
|---|---|---|---|---|---|---|---|
| | (1-26) | (27-38) | (39-55) | (56-65) | (66-104) | (105-117) | (118-128) |
| 10B6 (SEQ ID NO: 2) | DVQLTQSPSFLASV GDRVTINCKAS QNI......NKY LNWYQQKL GEAPKRLIY NTN......N NLQTGIP S RFSGSA...SG TDYTLTISSLHP EDFATYFC LQHS....SLYT FGAGTKLELK | | | | | | |
| GKV22S7A1 (SEQ ID NO: 12) (Rattus norvegicus) | DIQMTQSPSFLASV GRVTINCKAS QNI......NKY LNWYQQKL GEAPLLIY NTN......N NLQTGIP S RFSGSS...SG TDYTLTISSLQP EDVATYFC LQHSSRP YT FGAGTKLEIK | | | | | | |
| | V L | | R | | A | H F | I |

FIG. 28D

>10B6H (SEQ ID NO: 3)    360BP

CAGGTGCAGCTGCAGCAGTCTGGACCTGAGCTGGCAAAGCCTGGCTCCTCAGTGAAGATTTCCTGCAAGGCTTC
TGGCTACACCTTTACCAGCTATGAAATGCACTGGATAAAGCAGAGGCCTGGACAGGGCCTTGAGTGGATTGGAT
ATATTTATCCTGAAAGTGGCAGTACAGGCTACAATGAGAAGTTCAAGGGCAAGGCCACACTGACTGTGGACAAA
TCCTCCCCACAGCCTACATGCAACTCAGCAGCCTGACACATCTGCTGTCTATTTCTGTACAAGAGG
ACTACGGGTACTGGGCTATGTTATGGATGTCTGGGGGTCACGGAACTTCAGTCACTGTCCCTCA

>10B6H (SEQ ID NO: 4)    120AA

QVQLQQSGPELAKPGSSVKISCKASGYTFTSYEMHWIKQRPGQGLEWIGYIYPESGSTGYNEKFKGKATLTVDK
SSPTAYMQLSSLTPDNSAVYFCTRGLRVLGYVMDVWGHGTSVTVSS

| | FR1-IMGT | CDR1-IMGT | FR2-IMGT | CDR2-IMGT | FR3-IMGT | CDR3-IMGT | FR4-IMGT |
|---|---|---|---|---|---|---|---|
| | (1-26) | (27-38) | (39-55) | (56-65) | (66-104) | (105-117) | (118-128) |
| 10B6 (SEQ ID NO: 4) | QVQLQQSGP ELAKP GSSVKISCKAS | GYTF....TSYE | MHWIKQRP GQGLEWIGY | IYPE..SGST | GYNEKFK.G KATLTVDKSS PTAYMQLSSLT PDNSAVYFC | AR...... .TRGLRVLGYVMDV | WGHGTSVTVSS |
| IGHV1S127*01 (SEQ ID NO: 13) | QVQLQQSGP ELVKP GASVKISCKAS | GYTF....TSYY | IHWVKQRP GQGLEWIG | VIYP..DGST | NYNEKF.K KATLTADTSS STAYMELSSLT SEDSAVYFC | AR | |
| Mus musculus | | | | | | | |
| | A S | | E S G | | V K R | F DM L G V Y H | |

SEQUENCE LISTING

<160> NUMBER OF SEQ ID NOS: 38

<210> SEQ ID NO 1
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 1

```
gacgtccagt tgacccagtc tccttcattc ctgtctgcat ctgtgggaga cagagtcact      60
atcaactgca aagcaagtca gaatattaac aagtacttaa actggtatca gcaaaagctt     120
ggagaagctc ccaaacgcct gatatataat acaaacaatt tgcaaacagg catcccatca     180
aggttcagtg gcagtgcatc tggtacagat tacacactca ccatcagcag cctgcaccct     240
gaagattttg ccacatattt ctgcttgcag catagtagtt tgtacacgtt tggagctggg     300
accaagctgg aactgaaa                                                   318
```

<210> SEQ ID NO 2
<211> LENGTH: 106
<212> TYPE: PRT
<213> ORGANISM: Artificial sequence
<220> FEATURE:
<223> OTHER INFORMATION: Synthetic peptide

<400> SEQUENCE: 2

Asp Val Gln Leu Thr Gln Ser Pro Ser Phe Leu Ser Ala Ser Val Gly
1               5                   10                  15

Asp Arg Val Thr Ile Asn Cys Lys Ala Ser Gln Asn Ile Asn Lys Tyr
            20                  25                  30

Leu Asn Trp Tyr Gln Gln Lys Leu Gly Glu Ala Pro Lys Arg Leu Ile
        35                  40                  45

Tyr Asn Thr Asn Asn Leu Gln Thr Gly Ile Pro Ser Arg Phe Ser Gly
    50                  55                  60

Ser Ala Ser Gly Thr Asp Tyr Thr Leu Thr Ile Ser Ser Leu His Pro
65                  70                  75                  80

Glu Asp Phe Ala Thr Tyr Phe Cys Leu Gln His Ser Ser Leu Tyr Thr
                85                  90                  95

Phe Gly Ala Gly Thr Lys Leu Glu Leu Lys
            100                 105

<210> SEQ ID NO 3
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 3

```
caggtgcagc tgcagcagtc tggacctgag ctggcaaagc ctggctcctc agtgaagatt      60
tcctgcaagg cttctggcta cacctttacc agctatgaaa tgcactggat aaagcagagg     120
cctggacagg gccttgagtg gattggatat atttatcctg aaagtggcag tacaggctac     180
aatgagaagt tcaagggcaa ggccacattg actgtagaca atcctccccc acagcctac     240 atgcaactca gcagcctgac acctgacaac tctgctgtct atttctgtac aagaggacta     300
cgggtactgg gctatgttat ggatgtctgg ggtcacggaa cttcagtcac tgtctcctca     360
```

<210> SEQ ID NO 4

```
<211> LENGTH: 120
<212> TYPE: PRT
<213> ORGANISM: Artificial sequence
<220> FEATURE:
<223> OTHER INFORMATION: Synthetic peptide

<400> SEQUENCE: 4
```

Gln Val Gln Leu Gln Gln Ser Gly Pro Glu Leu Ala Lys Pro Gly Ser
1               5                   10                  15

Ser Val Lys Ile Ser Cys Lys Ala Ser Gly Tyr Thr Phe Thr Ser Tyr
            20                  25                  30

Glu Met His Trp Ile Lys Gln Arg Pro Gly Gln Gly Leu Glu Trp Ile
        35                  40                  45

Gly Tyr Ile Tyr Pro Glu Ser Gly Ser Thr Gly Tyr Asn Glu Lys Phe
    50                  55                  60

Lys Gly Lys Ala Thr Leu Thr Val Asp Lys Ser Ser Pro Thr Ala Tyr
65                  70                  75                  80

Met Gln Leu Ser Ser Leu Thr Pro Asp Asn Ser Ala Val Tyr Phe Cys
                85                  90                  95

Thr Arg Gly Leu Arg Val Leu Gly Tyr Val Met Asp Val Trp Gly His
            100                 105                 110

Gly Thr Ser Val Thr Val Ser Ser
            115                 120

```
<210> SEQ ID NO 5
<211> LENGTH: 77
<212> TYPE: PRT
<213> ORGANISM: Homo sapiens

<400> SEQUENCE: 5
```

Thr Glu Pro Leu Ala Leu Thr Glu Thr Asp Ile Cys Lys Leu Pro Lys
1               5                   10                  15

Asp Glu Gly Thr Cys Arg Asp Phe Ile Leu Lys Trp Tyr Tyr Asp Pro
            20                  25                  30

Asn Thr Lys Ser Cys Ala Arg Phe Trp Tyr Gly Gly Cys Gly Gly Asn
        35                  40                  45

Glu Asn Lys Phe Gly Ser Gln Lys Glu Cys Glu Lys Val Cys Ala Pro
    50                  55                  60

Val Leu Ala Lys Pro Gly Val Ile Ser Val Met Gly Thr
65                  70                  75

```
<210> SEQ ID NO 6
<211> LENGTH: 68
<212> TYPE: PRT
<213> ORGANISM: Mus musculus

<400> SEQUENCE: 6
```

Thr Glu Pro Leu Phe Leu Thr Lys Thr Asp Ile Cys Lys Leu Ser Arg
1               5                   10                  15

Asp Ala Gly Thr Cys Val Asp Phe Lys Leu Leu Trp His Tyr Asp Leu
            20                  25                  30

Glu Ser Lys Ser Cys Lys Arg Phe Trp Tyr Gly Gly Cys Gly Gly Asn
        35                  40                  45

Glu Asn Arg Phe His Ser Gln Glu Glu Cys Glu Lys Met Cys Ser Pro
    50                  55                  60

Glu Leu Thr Val
65

-continued

<210> SEQ ID NO 7
<211> LENGTH: 6
<212> TYPE: PRT
<213> ORGANISM: Artificial sequence
<220> FEATURE:
<223> OTHER INFORMATION: Synthetic peptide

<400> SEQUENCE: 7

Gln Asn Ile Asn Lys Tyr
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic peptide

<400> SEQUENCE: 8

Leu Gln His Ser Ser Leu Tyr Thr
1               5

<210> SEQ ID NO 9
<211> LENGTH: 8
<212> TYPE: PRT
<213> ORGANISM: Artificial sequence
<220> FEATURE:
<223> OTHER INFORMATION: Synthetic peptide

<400> SEQUENCE: 9

Gly Tyr Thr Phe Thr Ser Tyr Glu
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic peptide

<400> SEQUENCE: 10

Ile Tyr Pro Glu Ser Gly Ser Thr
1               5

<210> SEQ ID NO 11
<211> LENGTH: 13
<212> TYPE: PRT
<213> ORGANISM: Artificial sequence
<220> FEATURE:
<223> OTHER INFORMATION: Synthetic peptide

<400> SEQUENCE: 11

Thr Arg Gly Leu Arg Val Leu Gly Tyr Val Met Asp Val
1               5                   10

<210> SEQ ID NO 12
<211> LENGTH: 107
<212> TYPE: PRT
<213> ORGANISM: Rattus norvegicus

<400> SEQUENCE: 12

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asn Lys Tyr
            20                  25                  30

Leu Asn Trp Tyr Gln Gln Lys Leu Gly Glu Ala Pro Lys Leu Leu Ile

```
              35                  40                  45
Tyr Asn Thr Asn Asn Leu Gln Thr Gly Ile Pro Ser Arg Phe Ser Gly
     50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Leu Gln His Ser Ser Arg Pro Tyr
                 85                  90                  95

Thr Phe Gly Ala Gly Thr Lys Leu Glu Leu Lys
            100                 105

<210> SEQ ID NO 13
<211> LENGTH: 115
<212> TYPE: PRT
<213> ORGANISM: Mus musculus

<400> SEQUENCE: 13

Gln Val Gln Leu Gln Gln Ser Gly Pro Glu Leu Val Lys Pro Gly Ala
1               5                  10                  15

Ser Val Lys Ile Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
         35                  40                  45

Gly Tyr Ile Tyr Pro Arg Asp Gly Ser Thr Asn Tyr Asn Glu Lys Phe
     50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                 85                  90                  95

Ala Arg Tyr Tyr Ala Met Asp Tyr Trp Gly Gln Gly Thr Ser Val Thr
            100                 105                 110

Val Ser Ser
       115

<210> SEQ ID NO 14
<211> LENGTH: 90
<212> TYPE: DNA
<213> ORGANISM: Artificial sequence
<220> FEATURE:
<223> OTHER INFORMATION: Synthetic primer

<400> SEQUENCE: 14
atggacagca aaggttcgtc gcagaaaggg tcccgcctgc tcctgctgct ggtggtgtca      60
aatctactct tgtgccaggg tgtggtctcc                                      90

<210> SEQ ID NO 15
<211> LENGTH: 20
<212> TYPE: DNA
<213> ORGANISM: Artificial sequence
<220> FEATURE:
<223> OTHER INFORMATION: Synthetic primer

<400> SEQUENCE: 15
acgagaacag attccactcc                                                 20

<210> SEQ ID NO 16
<211> LENGTH: 22
<212> TYPE: DNA
<213> ORGANISM: Artificial sequence
<220> FEATURE:
<223> OTHER INFORMATION: Synthetic primer
```

```
<400> SEQUENCE: 16
tcagcagtag cctcatcatc ac                                              22

<210> SEQ ID NO 17
<211> LENGTH: 20
<212> TYPE: DNA
<213> ORGANISM: Artificial sequence
<220> FEATURE:
<223> OTHER INFORMATION: Synthetic primer

<400> SEQUENCE: 17
agagacctac gtcgagcagc                                                 20

<210> SEQ ID NO 18
<211> LENGTH: 20
<212> TYPE: DNA
<213> ORGANISM: Artificial sequence
<220> FEATURE:
<223> OTHER INFORMATION: Synthetic primer

<400> SEQUENCE: 18
gggtccatgg tgatacaagg                                                 20

<210> SEQ ID NO 19
<211> LENGTH: 25
<212> TYPE: DNA
<213> ORGANISM: Artificial sequence
<220> FEATURE:
<223> OTHER INFORMATION: Synthetic primer

<400> SEQUENCE: 19
cccttcaggc caccttcttt gaggt                                           25

<210> SEQ ID NO 20
<211> LENGTH: 20
<212> TYPE: DNA
<213> ORGANISM: Artificial sequence
<220> FEATURE:
<223> OTHER INFORMATION: Synthetic primer

<400> SEQUENCE: 20
gtccagtaac caccctgctg                                                 20

<210> SEQ ID NO 21
<211> LENGTH: 21
<212> TYPE: DNA
<213> ORGANISM: Artificial sequence
<220> FEATURE:
<223> OTHER INFORMATION: Synthetic primer

<400> SEQUENCE: 21
ctgtatggac atcgtcggca g                                               21

<210> SEQ ID NO 22
<211> LENGTH: 20
<212> TYPE: DNA
<213> ORGANISM: Artificial sequence
<220> FEATURE:
<223> OTHER INFORMATION: Synthetic primer

<400> SEQUENCE: 22
acttacacgc cccaaggatg                                                 20

<210> SEQ ID NO 23
```

<210> SEQ ID NO 23
<211> LENGTH: 20
<212> TYPE: DNA
<213> ORGANISM: Artificial sequence
<220> FEATURE:
<223> OTHER INFORMATION: Synthetic primer

<400> SEQUENCE: 23
cggccaggta catcgacttc                                              20

<210> SEQ ID NO 24
<211> LENGTH: 20
<212> TYPE: DNA
<213> ORGANISM: Artificial sequence
<220> FEATURE:
<223> OTHER INFORMATION: Synthetic primer

<400> SEQUENCE: 24
tgcagcttgc catcttggag                                              20

<210> SEQ ID NO 25
<211> LENGTH: 20
<212> TYPE: DNA
<213> ORGANISM: Artificial sequence
<220> FEATURE:
<223> OTHER INFORMATION: Synthetic primer

<400> SEQUENCE: 25
tcagcaagat ccagacgctc                                              20

<210> SEQ ID NO 26
<211> LENGTH: 20
<212> TYPE: DNA
<213> ORGANISM: Artificial sequence
<220> FEATURE:
<223> OTHER INFORMATION: Synthetic primer

<400> SEQUENCE: 26
ctgagatgtg caggtgggtc                                              20

<210> SEQ ID NO 27
<211> LENGTH: 20
<212> TYPE: DNA
<213> ORGANISM: Artificial sequence
<220> FEATURE:
<223> OTHER INFORMATION: Synthetic primer

<400> SEQUENCE: 27
cgattacgag ggcagtggtt                                              20

<210> SEQ ID NO 28
<211> LENGTH: 20
<212> TYPE: DNA
<213> ORGANISM: Artificial sequence
<220> FEATURE:
<223> OTHER INFORMATION: Synthetic primer

<400> SEQUENCE: 28
agtcccctag tcgtcctcac                                              20

<210> SEQ ID NO 29
<211> LENGTH: 20
<212> TYPE: DNA
<213> ORGANISM: Artificial sequence
<220> FEATURE:
<223> OTHER INFORMATION: Synthetic primer

<400> SEQUENCE: 29
ggcaatccca cttatggcct                                                 20

<210> SEQ ID NO 30
<211> LENGTH: 20
<212> TYPE: DNA
<213> ORGANISM: Artificial sequence
<220> FEATURE:
<223> OTHER INFORMATION: Synthetic primer

<400> SEQUENCE: 30
tccgtgacag ttaggttggc                                                 20

<210> SEQ ID NO 31
<211> LENGTH: 20
<212> TYPE: DNA
<213> ORGANISM: Artificial sequence
<220> FEATURE:
<223> OTHER INFORMATION: Synthetic primer

<400> SEQUENCE: 31
gccagcagta tgaaagcgtg                                                 20

<210> SEQ ID NO 32
<211> LENGTH: 20
<212> TYPE: DNA
<213> ORGANISM: Artificial sequence
<220> FEATURE:
<223> OTHER INFORMATION: Synthetic primer

<400> SEQUENCE: 32
acctgtctcc ggtactcgtt                                                 20

<210> SEQ ID NO 33
<211> LENGTH: 20
<212> TYPE: DNA
<213> ORGANISM: Artificial sequence
<220> FEATURE:
<223> OTHER INFORMATION: Synthetic primer

<400> SEQUENCE: 33
ttgtgtccac cttccacaaa                                                 20

<210> SEQ ID NO 34
<211> LENGTH: 20
<212> TYPE: DNA
<213> ORGANISM: Artificial sequence
<220> FEATURE:
<223> OTHER INFORMATION: Synthetic primer

<400> SEQUENCE: 34
tgttgctgtc caagttgctc                                                 20

<210> SEQ ID NO 35
<211> LENGTH: 20
<212> TYPE: DNA
<213> ORGANISM: Artificial sequence
<220> FEATURE:
<223> OTHER INFORMATION: Synthetic primer

<400> SEQUENCE: 35
acgcccatca ccactctaac                                                 20

<210> SEQ ID NO 36
<211> LENGTH: 20
<212> TYPE: DNA

```
<213> ORGANISM: Artificial sequence
<220> FEATURE:
<223> OTHER INFORMATION: Synthetic primer

<400> SEQUENCE: 36
ctaaactgca cgaccccaat                                                    20

<210> SEQ ID NO 37
<211> LENGTH: 19
<212> TYPE: DNA
<213> ORGANISM: Artificial sequence
<220> FEATURE:
<223> OTHER INFORMATION: Synthetic primer

<400> SEQUENCE: 37
ggcatgcggc ccgtctctc                                                     19

<210> SEQ ID NO 38
<211> LENGTH: 20
<212> TYPE: DNA
<213> ORGANISM: Artificial sequence
<220> FEATURE:
<223> OTHER INFORMATION: Synthetic primer

<400> SEQUENCE: 38
cttccctggg catcacggcg                                                    20
```

ENDOTROPHIN NEUTRALIZATION AND USE THEREOF

This application claims benefit of priority to U.S. Provisional Application Ser. No. 61/956,807, filed Jun. 17, 2013, the entire contents of which are hereby incorporated by reference.

STATEMENT OF GOVERNMENT LICENSE RIGHTS

This invention was made with government support under Grant No. USAMRMC BC085909 awarded by the Department of Defense. The government has certain rights in the invention.

INCORPORATION OF SEQUENCE LISTING

The sequence listing that is contained in the file named "UTSH0303US_ST25.txt", which is 13 KB (as measured in Microsoft Windows®) and was created on Jun. 9, 2014, is filed herewith by electronic submission and is incorporated by reference herein.

BACKGROUND

The platinum-based chemotherapeutic agent cisplatin (cis-diammine-dichloro-platinum) has been well established in clinical treatment regimens due to its effectiveness on human tumor cells, such as in the context of ovarian, lung, testicular and breast cancer (Kelland, 2007; Lee et al, 2004; Sirohi et al, 2008). Cisplatin triggers formation of intrastrand and inter-strand DNA-adducts, which leads to cell cycle arrest, followed by apoptosis (Kelland, 2007). However, an inherent or acquired resistance to cisplatin is a major clinical drawback for patients who relapse after an initial favorable responses (Galluzzi et al, 2012). Cisplatin resistance is a complex problem which involves multiple pathways including increased drug efflux, evasion of apoptotic pathways, a bypass of the replication checkpoint, increased cell proliferation and increased DNA damage repair (Galluzzi et al, 2012). To overcome the drug resistance against platinum-based chemotherapy, combination therapies with peroxisome proliferator-activated receptor gamma (PPARγ) agonists, the thiazolidinediones (TZDs), have been performed. The basis for this approach is the growth inhibitory effect of these PPARγ agonists on transformed cells through both PPARγ-dependent and -independent pathways (Blanquicett et al, 2008; Mueller et al, 1998; Palakurthi et al, 2001; Satoh et al, 2002). PPARγ is a member of the nuclear hormone receptor superfamily and a key transcription factor for adipogenesis. It is also involved in various physiological processes, such as cell proliferation, angiogenesis, inflammation and lipid partitioning (Tontonoz & Spiegelman, 2008). Combination therapies with TZDs have been shown to display beneficial effects on cancer cell death, while also leading to a reduction of overall systemic toxicity to these chemotherapeutic regimens (Girnun et al, 2008; Girnun et al, 2007; Tikoo et al, 2009). However, the detailed molecular basis underlying the beneficial effects of TZDs to platinum treatment has yet to be documented prior to the present invention.

In the tumor microenvironment, both stromal and cancer cells contribute to various types of extracellular matrix (ECM) proteins to actively remodel the microenvironment favorably for tumor growth and metastasis. Such ECM proteins include fibronectin, laminin, collagen I (*COL1*), collagen IV (COL4) and collagen VI (COL6), and these ECM components are markedly modulated in response to chemotherapy (Dangi-Garimella et al, 2011; Sherman-Baust et al, 2003; Su et al, 2007). They have been suggested to cause drug resistance in solid tumors, including small-cell lung cancer, ovarian cancer, pancreatic cancer and breast cancer (Helleman et al, 2008; Rintoul & Sethi, 2001; Sherman-Baust et al, 2003; Shields et al, 2012) through multiple pathways. These include an induction of anti-apoptotic pathways (Sethi et al, 1999), decreased drug transport (Netti et al, 2000) and increased survival signals, such as those mediated through integrin-based pathways (Jean et al, 2011). COL6 is composed of three alpha chains; α1, α2 and α3. Particularly, the α3 chain of COL6 (COL6A3) has been highlighted as a promising candidate triggering drug resistance against platinum-based therapeutics since its levels are vastly increased in the cisplatin-resistant cancer cells in vitro (Sherman-Baust et al, 2003; Varma et al, 2005). Nevertheless, the more detailed mechanism underlying how COL6A3 regulates drug-resistance has remained elusive. Furthermore, compositions useful for inhibiting COL6A3 have yet to be characterized in connection with chemotherapy.

SUMMARY OF THE INVENTION

Aspects of the present invention relate to methods and reagents for increasing chemosensitivity to platinum-based chemotherapy. In one aspect, a method of increasing chemosensitivity to platinum-based chemotherapy is provided, comprising administering to a patient in need thereof an effective amount of an endotrophin-neutralizing agent. The agent can be a monoclonal antibody, or fragment thereof, capable of binding to the C5 domain of the alpha3 chain of human collagen VI (e.g., SEQ ID NO: 5). In some embodiments, the method can further include administering an effective amount of thiazolidinedione to said patient.

In a further embodiment there is provided a method of treating a cancer patient comprising administering an effective amount of an endotrophin-neutralizing agent (e.g., an antibody that binds that binds to the C5 domain of the alpha3 chain of human collagen VI) or TGFβ antagonist (e.g., an antibody that binds to TGFβ). In some aspects, such a method is further defined as a method for increasing chemosensitivity to platinum-based chemotherapy or for inhibiting angiogenesis in the patient. In certain aspects, the patient is a cancer patient, such as a patient having a breast or colon cancer.

In further aspects, a method of the embodiments further comprises administering at least a second anti-cancer therapy to a patient. For example, the second anti-cancer therapy can be administered before, after or essentially simultaneously with an endotrophin-neutralizing agent or a TGFβ antagonist. In some aspects, the second anti-cancer therapy is a chemotherapy, radiotherapy, gene therapy, surgery, hormonal therapy, anti-angiogenic therapy or cytokine therapy. In preferred aspects, the chemotherapy comprises a platinum-based chemotherapy, such as cisplatin, oxaliplatin or carboplatin. In still further aspects, a method of the embodiments further comprises administering thiazolidinedione to the patient (e.g., in conjunction with a platinum-based chemotherapy).

In further aspects, a patient for treatment according to the embodiments is a patient who has been determined to express an elevated level of endotrophin relative to control patient. For example, in some cases, a patient can be determined to have an elevated level of endotrophin by measuring the level an endotrophin polypeptide in a sample from the patient such as a serum, stool or biopsy sample. In still further aspects, an elevated level of endotrophin can be determined by measuring an elevated level of COL6A3 RNA in a sample (e.g., a cancer cell sample) of the patient.

A further embodiment of the present invention includes a monoclonal antibody, or fragment thereof, capable of binding to the C5 domain of the alpha3 chain of human collagen VI (SEQ ID NO: 5) or the C5 domain of the alpha3 chain of mouse collagen VI (SEQ ID NO: 6). In some aspects, the antibody competes for binding of the C5 domain of the alpha3 chain with the 10B6 monoclonal antibody. In certain embodiments, the monoclonal antibody, or fragment thereof, includes: a) a light chain comprising three light chain complementary regions (CDRs) having the following amino acid sequences: i) the light chain CDR1: QNINKY (SEQ ID NO: 7); ii) the light chain CDR2: NTN; iii) the light chain CDR3: LQHSSLYT (SEQ ID NO: 8); and a light chain framework sequence from an immunoglobulin light chain; and b) a heavy chain comprising three heavy chain complementary regions (CDRs) having the following amino acid sequences: i) the heavy chain CDR1: GYTFTSYE (SEQ ID NO: 9); ii) the heavy chain CDR2: IYPESGST (SEQ ID NO: 10); iii) the heavy chain CDR3: TRGLRVLGYVMDV (SEQ ID NO: 11); and a heavy chain framework sequence from an immunoglobulin heavy chain. In some embodiments, the monoclonal antibody, or fragment thereof may include: i) the light chain variable region with the amino acid sequence of SEQ ID NO: 2; and ii) the heavy chain variable region with the amino acid sequence of SEQ ID NO: 4. In some aspects, an antibody of the embodiments is a recombinant and/or purified antibody. For example, the recombinant antibody can be a human, humanized antibody or de-immunized antibody. In still further aspects, the antibody is an IgG, IgM, IgA or an antigen binding fragment thereof. In yet further aspects, the antibody is a Fab', a F(ab')2, a F(ab')3, a monovalent scFv, a bivalent scFv, or a single domain antibody.

In still further aspects, an antibody (or fragment thereof) in accordance with the embodiments is conjugated or fused to an imaging agent or a cytotoxic agent. For example, the imagining agent can be an MRI contrast agent, a radionuclide or a fluorescence moiety. In certain aspects, the antibody is conjugated to a chemotherapeutic agent such as a platinum-base chemotherapeutic. In still further aspects, an antibody can be fused to a toxin moiety such as gelonin, granzyme or a bacterial toxin. Such antibody conjugates and fusions can likewise be employed in the methods of the embodiments.

In yet a further embodiment there is provided a pharmaceutical composition comprising an antibody of the embodiments.

Another aspect of the invention relates to a method of treating a metabolic disorders-related disease (e.g., diabetes), comprising administering to a patient in need thereof an effective amount of an endotrophin-neutralizing agent. The agent can be a monoclonal antibody, or fragment thereof, capable of binding to the C5 domain of the alpha3 chain of human collagen VI (e.g., SEQ ID NO: 5).

In some embodiments, endotrophin, a cleavage product of COL6A3 is identified as being actively involved in mammary tumor progression through enhancing the epithelial-mesenchymal transition (EMT), fibrosis and chemokine activity, thereby recruiting stromal cells to the tumor microenvironment. Notably, all of these activities are associated with acquired drug resistance. In this study, increased levels of endotrophin following cisplatin exposure are reported. This causes cisplatin-resistance through enhancing the EMT. Furthermore, endotrophin levels were decreased by combination therapy with TZD, leading to a decrease of EMT, fibrosis and vasculature, thereby enhancing cisplatin sensitivity. Taken together, these results suggest that the beneficial effects of TZDs on platinum-based chemotherapy are mediated through the inhibition of endotrophin in mammary tumors, and that the neutralization of endotrophin activity is a key determinant to unleash the full beneficial effects of TZDs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) COL6 is composed of COL6α1, -α2, and -α3 chains. The C5 domain of the α3 chain, cleaved off the COL6 microfilament, is highlighted in red. Shown are amino acid sequences compared between the human (SEQ ID NO: 5) and mouse (SEQ ID NO: 6) COL6α3-05 domain. Conserved sequences are highlighted in yellow. (FIG. 1B) Western blots showing abundant secretion of ETP from adipocytes. Conditioned media from 3T3-L1 preadipocytes and fully differentiated adipocytes were subjected to Western blotting using α-mETP and α-COL6. Arrows indicate the secreted form of ETP. (FIG. 1C) ETP immunostaining of mammary gland tissues from obese animals, ob/ob and db/db mice, compared with lean controls (n=5 per group). Arrows indicate crown structure. Scale bars: 50 µm. (FIG. 1D and FIG. 1E) holo-COL6 and ETP immunostaining of tumor tissues from 9-week-old PyMT mice with α-COL6 (FIG. 1D) and α-mETP antibody (FIG. 1E), respectively. Lung tissues from 13-week-old PyMT mice were used for metastasized tumor lesions (FIG. 1F). Scale bars: 50 µm. (FIG. 1G) α-COL6- and α-ETP-positive staining area in tumor or stroma for the primary tumors. Data are mean±SEM of multiple fields in n=5 per group. ***P<0.001 vs. tumor, unpaired t test.

(FIG. 2A and FIG. 2B) Human cancer tissues compared with those of benign tissues were immunostained with human ETP-specific polyclonal antibody. Human samples for breast cancer (FIG. 2A) and colon cancer (FIG. 2B) were analyzed. Scale bars: 25 µm. (FIG. 2C and FIG. 2D) Whole body in vivo imaging of injected ETP. IRD-800 fluorescence-labeled ETP protein (10 µg) was intravenously injected into WT, 8-week-old PyMT, and 10-week-old PyMT mice by tail vein. (FIG. 2C) ETP levels were visualized by the Licor Infrared Scanner 10-90 minutes after injection. Arrows indicate mammary tumors. L, liver; B, bladder; T, tumor. IgG was used as a negative control. (FIG. 2D) Tissues were excised 2 hours after injection, and ETP-positive fluorescence signals were determined with a Licor Infrared Scanner. Quantified values were normalized to total area and represented as percentage of WT. ***P<0.001.

(FIG. 3A) ETP immunostaining showing strong ETP positive signal in mammary ductal epithelium in the transgenic mice lines (ETP low and high). Scale bars: 50 µm. (FIG. 3B and FIG. 3C) Antiapoptotic effects of ETP. (FIG. 3B) Apoptosis for mammary epithelial cells during involution was determined by TUNEL assay on mammary glands of WT, ETP, and mice 2 days after forced weaning Arrows indicate TUNEL-positive apoptotic cells. Scale bars: 50 µm. (FIG. 3C) Quantification of TUNEL-positive cells, represented as mean±SEM (multiple images, n=3 per group). ***P<0.001, *P<0.05 vs. WT, unpaired t test. (FIG. 3D and FIG. 3E) Promitotic effects of ETP. High ETP expressers (32 weeks old) spontaneously developed tumors. (FIG. 3D) Whole body image (left; arrows indicate tumors) and H&E staining of mammary gland (middle) and lung (right) tissue. Boxed regions are shown at higher magnification below. Scale bars: 200 µm. (FIG. 3E) Cell proliferation was determined by Ki67 staining with mammary glands of 32-week-old ETP high-expressing and WT mice. Scale bars: 50 µm.

(FIG. 4A) ETP immunostaining, with a high ETP-positive signal in tumor tissues from 12-week-old PyMT and PyMT/ETP mice. Scale bars: 50 µm. Intensity of ETP staining was quantified and represented as mean±SEM (n=5 per group). *P=0.02 vs. PyMT, unpaired t test. (FIG. 4B) Whole-mount staining of mammary gland tissues from 8-week-old PyMT and PyMT/ETP mice, with early neoplastic lesion areas increased by ETP. (FIG. 4C) Tumor volume was determined by weekly caliper measurements from PyMT (n=35) and PyMT/ETP (n=38) mice. Results are represented as mean±SEM. P=NS, 2-way ANOVA. (FIG. 4D and FIG. 4E) ETP augmented pulmonary metastasis. (FIG. 4D) Pulmonary metastatic growth was determined by measuring the tumor incidence in lung tissues (8- to 17-week-old, n=22-25 per group). H&E-stained preparations for lung tissues were used for analysis. Shown is percent metastasis-free mice over time. *P=0.025, log-rank test. (FIG. 4E) Representative H&E stain for lung tissues showing the degree of pulmonary metastasis in 15- and 17-week-old PyMT and PyMT/ETP mice. (FIG. 4F) Representative whole-body images for tumor burden. Tumor volume for 13-week-old FP635/PyMT and FP635/PyMT/ETP mice was monitored by IVIS fluorescence scanner. Metastatic burden was determined by fluorescence signals in lung tissues. Quantified results are represented as mean±SEM (n=8-9 per group). *P=0.0117, **P=0.0011 vs. PyMT, unpaired t test.

(FIG. 5A) Proliferation indices were determined by immunostaining with Ki67. Quantified results represent mean±SEM (n=5 per group). P=NS vs. PyMT, unpaired t test. (FIG. 5B) Fibrosis indices were determined by Masson's Trichrome C stain. Percent fibrotic area over the tumor lesions was quantified. Data represent mean±SEM (n=5 per group). P=0.01 vs. PyMT, unpaired t test. Arrows indicate collagen fibrils. (FIG. 5C) Functional blood vessel areas were determined by lectin perfusion. Podoplanin (lymphangiogenesis marker) and DAPI (nucleus) were costained. Quantified results represent mean±SEM (n=5 per group). P=0.003 vs. PyMT, unpaired t test. (FIG. 5D) Hypoxia was determined by pimonidazole-HCl injection. Hypoxic lesions were stained in dark brown. Quantified results represent mean±SEM (n=5 per group). ***P=0.0007 vs. PyMT, unpaired t test. (FIGS. 5E-5H) Total RNA was prepared from the tumor tissues from PyMT/ETP and PyMT mice. mRNA levels for the genes responsible for fibrosis and EMT (FIG. 5E and FIG. 5F), angiogenesis and lymphangiogenesis (FIG. 5G), and inflammation (FIG. 5H) were determined by qRT-PCR. mRNA levels were normalized with β-actin and represented as mean±SEM (n=8 per group). Relative values of each gene are represented as fold change relative to PyMT. *P<0.05, ***P<0.001 vs. PyMT, 2-way ANOVA. Scale bars: 50 µm (FIGS. 5A-5C); 100 µm (FIG. 5D). Insets in FIG. 5A are enlarged ×5.

(FIG. 6A) E-cadherin immunostaining for tumor tissues from PyMT and PyMT/ETP. (FIG. 6B and FIG. 6C) SBE-luciferase reporter assay. See Supplemental Methods for details. Data represent fold increase (3 independent experiments). **P<0.01, *P<0.05, 2-way ANOVA. pRA-ctrl, empty; pRA-sETP, secretion form; pRA-ETP, intracellular form. (FIGS. 6D-6G) Allografts of Met-1 cells in the presence of either ETP (20 ng/plug) or PBS mixed with 1D11 or IgG (10 µg/plug) within a Matrigel plug. 10 days after implantation, additional 1D11 or IgG (100 µg) was i.p. injected once a week during tumor progression. (FIG. 6D) Tumor volumes represent means±SEM (n=5 per group). *P<0.05, 2-way ANOVA. (FIG. 6E) H&E staining. The ratio of stromal area in tumor tissues was quantified. Data represent mean±SEM (n=5 per group). *P<0.05, unpaired t test. T; tumor and S; stroma. (FIG. 6F) Fibrosis was determined by Masson's Trichrome C stain. Data represent mean±SEM (n=5 per group). P<0.01, *P<0.001, unpaired t test. (FIG. 6G) Western blotting for EMT markers E-cadherin, vimentin, and α-SMA. β-actin, loading control. Data represent fold increase (n=5 per group). *P<0.05, P<0.01, *P<0.001, unpaired t test. (FIG. 6H) Control and ETP$^+$-cancer cells were isolated from FP635/PyMT and FP635/PyMT/ETP mice and conveyed into WT mice by tail vein injection (0.5×10$^6$ cells/mouse). Either IgG or 1D11 (100 µg) was i.p. injected every 5 days. 20 days post injection, metastasized cancer cells in the lung tissues were determined by fluorescence intensity. Data represent fold increase (n=3-4 per group). **P<0.01, *P<0.05, unpaired t test. Scale bars: 20 µm (FIG. 6A); 50 µm (FIG. 6E); 100 µm (FIG. 6F).

(FIG. 7A) Tumor growth significantly increased in ETP$^+$-tumor tissue allograft into WT mice. Tumor volume was determined 1 month after implantation (representative images). Data represent mean±SEM (n=5 per group). *P<0.001, unpaired t test. (FIG. 7B) In vivo Matrigel bioassay. Matrigel (50 µl) was mixed with ETP (100 ng/plug) or PBS and implanted into WT mice in the presence of IgG, 1D11, or 10B6 (20 µg/plug). 2 days after implantation, plugs were excised and stained for FIG. 7H & FIG. 7E. Scale bars: 100 µm. (FIGS. 7C-7H) Cancer cells were plated in the bottom chamber 1 day prior to seeding MS-1 cells (5×10$^5$ cells/well) and macrophages (1×10$^5$ cells/well) atop the membrane chamber in Transwell and incubated for 18-24 hours (FIG. 7C). (FIGS. 7D, 7E, 7F, 7G) Representative images of multiple independent experiments. Scale bars: 100 µm. (FIG. 7H) Quantitation (mean±SEM; n=3 per group). *P<0.001, **P<0.05, *P<0.01, unpaired t test. (FIG. 7I) MS-1 migration assay. MS-1 cells (5×10$^5$ cells/well) were plated atop the chamber in Transwell and incubated for 24 hours. Chemotaxis was set up by following cell migration from DMEM/serum-free to DMEM/2% FBS/PBS or DMEM/2% FBS/ETP protein (1 µg/well). Images are representative of multiple independent experiments. Data represent mean±SEM (n=3 per group). ***P=0.008, unpaired t test. Scale bars: 100 µm.

(FIG. 8A) 10B6 (200 µg/mouse) was i.p. injected twice weekly into PyMT mice from 9 to 13 weeks of age. Tumor growth (mean±SEM; n=4-6 per group) was determined by weekly caliper measurements. *P<0.05, P<0.01, *P<0.001 vs. IgG control, 2-way ANOVA. (FIG. 8B) Primary mammary epithelial cancer cells were isolated from 12-week-old FP635/PyMT and FP635/PyMT/ETP mice and implanted into WT recipients with the same volume of Matrigel. For the 10B6 group, 10B6 was added in a Matrigel plug (10 μg/plug) admixed with ETP$^+$-cancer cells (i.e., ETP$^+$/10B6). A representative whole-body image was acquired 25 days after implantation using IVIS fluorescence scanner. Artificial color indicates fluorescence signal intensity accounts for tumor volume (AU). Quantitative results are represented as mean±SEM (n=3 per group). *P<0.05, unpaired t test. (FIGS. 8C-8I) 6 weeks after implantation, tumor tissues were excised from Ctrl-, ETP$^+$-, and ETP$^+$/10B6-cancer cells allografted mice and stained for H&E (FIG. 8C), Masson's Trichrome C (FIG. 8D), α-SMA (FIG. 8E), FSP-1 (FIG. 8F), CD31 (FIG. 8G), F4/80 (FIG. 8H), and Ki67 (FIG. 8I). Quantified results in FIGS. 8D-8I are mean±SEM (multiple images, n=3 per group). *P<0.05, **P<0.01, unpaired t test. Scale bars: 50 μm. (FIG. 8J) Working model for ETP in mammary tumor progression.

FIG. 9A. HEK-293 cell produced mouse endotrophin was subjected to Western blotting using rabbit anti-mouse endotrophin polyclonal antibody. FIG. 9B. Bacterially produced GST-fused recombinant human endotrophin protein was subjected to western blotting using a rabbit anti-human endotrophin polyclonal antibody. GST protein was used as a negative control. The arrow points at endotrophin. FIG. 9C. Rat anti-mouse endotrophin monoclonal antibodies efficiently capture the native form of endotrophin protein. IRD (infrared dye)-800 labeled native form of endotrophin protein was incubated with either endotrophin monoclonal antibodies, including 4D1, 4F8, 10B6-A11, 10B6-B5, and 10B6-C3 or a rat-IgG for 2 hours at room temperature and subsequently incubated with Protein G Sepharose for 1 hour. The protein-Sepharose complex was separated on a 10-20% Tricine gel after 3 times washing with PBS. Captured endotrophin protein was visualized on a Licor Odyssey Infrared Scanner (Licor Bioscience). Green color represents the IRD800 channel.

FIGS. 10A-10B. Endotrophin is highly expressed in human breast cancer (FIG. 10A) and colon cancer (FIG. 10B) tissues compared to samples obtained from benign lesions. Human breast and colon cancer samples (UTSW Medical Cancer Human Tissue Bank) were immunostained with polyclonal human endotrophin antibodies (TX933). Human samples for breast- and colon cancer patients were analyzed. Scale bars: 100 μm (10×) and 25 μm (40×). FIG. 10C. COL6 immunostaining for adipose tissues of obese animals such as ob/ob and db/db mice compared to lean control mice (pan-collagen 6 antibody, Abcam, Ab6588). Scale bars: 50 μm. FIG. 10D. Endotrophin mRNA levels in various cell lines: mRNA levels for endotrophin were determined by qRT-PCR with various cell lines such as MS1 (mouse endothelial cells), mouse primary macrophages, and Met-1 (mouse mammary cancer cells). qRT-PCR results were normalized with β-actin. FIGS. 10E-10F. Tissue distribution of COLE. Various tissues were collected from 10-week-old FVB WT mice or tumor tissues from PyMT mice and analyzed for COL6A1, -A2, and -A3 mRNA levels. qRT-PCR results were normalized with 18S RNA (FIG. 10E). p<0.01, *p<0.001 vs. mammary gland (M. gland) by 2-way ANOVA (n=4/group). Results were normalized with β-actin and represented as mean±SEM (FIG. 10F).

FIG. 11A. Diagram for the MMTV-endotrophin transgenic mice. FIG. 11B. Tissue distributions of endotrophin transgene. mRNA levels for the endotrophin transgene were determined by qRT-PCR with various tissues from low expressers (line 2145, left Y-axis) and high expressers (line 2246, right Y-axis). Results were normalized with β-actin. FIGS. 11C-11D. Mammary ductal epithelium growth develops normally in the endotrophin transgenic mice. Morphological analysis of ductal epithelial growth was performed with whole mount preparations (FIG. 11C) and H&E stain (FIG. 11D) of inguinal mammary glands from 8-week-old WT, and endotrophin transgenic (ETP-Tg; low and high expresser) mice. Scale bars: 50 μm in H&E. FIG. 11E. Tissue fibrosis was determined by Masson's Trichrome C staining of 8-week-old mice. Collagen fibrils are stained with blue. Scale bars: 50 μm. Quantified results are represented as mean±SEM (n=5/group). p=n.s (no significance) vs. WT by unpaired t-test. FIG. 11F. Reproduction was determined by measuring pregnancy incidence, litter size, and duration of pregnancy (from mating to delivery). n=5-9 per group. FIG. 11G. The rate of involution was determined by morphological analysis with H&E preparations of mammary gland at indicated days after forced weaning.

FIG. 12A. Infrared fluorescence protein (FP635) is exclusively expressed in the mammary ductal epithelium under the control of MMTV promoter. A MMTV-FP635 transgenic mouse line was established starting with 7 independent founders by screening for FP635 fluorescence protein expression in frozen sectioned mammary gland tissues. Images were acquired using a Leica confocal microscope. The DAPI stain highlights nuclei. FIG. 12B. Longitudinal whole body in vivo tumor imaging with MMTV-FP635 transgenic mice (FP635/PyMT). Female MMTV-FP635 mice were crossed with male MMTV-PyMT mice to obtain female FP635/PyMT mice. Tumor volume for the PyMT/FP635 mice at indicated time points was determined by integration of infrared fluorescence signal expressed in the ductal epithelium during tumor progression. Images were acquired with a Maestro Fluorescence Scanner.

FIG. 13A. cDNA microarrays for tumor tissues from PyMT vs. PyMT/ETP were analyzed. Diagram represents % of modulated genes by PyMT/ETP vs. PyMT. Functional annotation for genes significantly changed by endotrophin is represented as a bar-graph. Analysis was performed with DAVID Bioinformatics Resources 6.7, National Institute of Allergy and Infectious Diseases (NIAID), NIH (http://david.abcc.ncifcrf.gov/home.jsp). FIG. 13B. Canonical pathway analysis for the cDNA microarray data was performed with Ingenuity System (http://www.ingenuity.com). Top 5 ranked canonical pathways are represented as a bar graph.

FIG. 14A. Supernatants were subjected to SDS-PAGE and Coomassie staining to check for endotrophin secretion. FIG. 14B. Cell lysates and supernatants were subjected to western blotting with anti-mouse endotrophin antibody. Intracellular endotrophin was presented in both ETP- and sETP-expressing cells. Whereas only sETP-overexpressing cells secrete endotrophin into the media, since the adiponectin signal sequence is an inefficient signal for secretion of a passenger protein. Arrow indicates secreted endotrophin.

FIG. 15A. Endotrophin$^{+-}$cancer cells grow at comparable rates as ctrl-cancer cells. An equal number of cancer cells were freshly isolated from tumor tissues of PyMT (ctrl-cancer cells) and PyMT/endotrophin (ETP$^{+-}$cancer cells) and implanted into WT mice ($1 \times 10^6$ cells/mouse). Tumor volume was determined 1 month post-implantation. Quantitative results are represented as mean±SEM (n=7/group). p=n.s vs. Ctrl-cancer cells by unpaired t-test. FIG. 15B. Met-1 cells were seeded into the 96 well plates and incubated with DMEM/10% FBS/PBS, DMEM/10% FBS/endotrophin, or conditioned media acquired from HEK293 or HEK293/endotrophin-overexpressing cells for 24 hours. Mitotic activity was measured with a Mitotic Index Assay Kit (Active Motif) following the manufacturer's protocol. Paclitaxel (1 μM) was used as a positive control of mitosis. Quantified results are represented as mean±SEM (n=10/group) p=n.s vs. PBS or Ctrl-media by unpaired t-test. FIG. 15C. Human breast cancer cells, MCF7 ($0.1 \times 10^5$) were plated in the 24 well plates with or without recombinant endotrophin protein and cell numbers were counted over time. The quantification of results is represented as mean±SEM (n=6/group, triplicate). p=n.s vs. PBS by unpaired t-test. FIG. 15D. Tumor tissues taken from FIG. 15A were immunostained for endothelium with anti-endomucin antibody (Santa Cruz. Biotechnology, Inc., sc-65495), demonstrating that the vascularization is significantly increased in ETP$^{+-}$cancer cells compared to Ctrl-cancer cells. Endomucin positive area was quantified and represented as mean±SEM (multiple images, n=4/group). ***p=0.0008 vs. ctrl by unpaired t-test. Scale bars: 200 μm.

FIGS. 16A-16C. Angiogenesis is significantly increased in ETP$^+$-tumors. Blood vessel area was determined by immunostaining with CD31; Functional vessel area was determined by lectin perfusion for Ctrl-tumors, tumor size adjusted Ctrl (SA)-tumors and ETP$^+$-tumors. DAPI (nucleus) was co-stained. Scale bars: 100 μm. CD31$^+$-area for blood vessel area (FIG. 16B) and functional vessel area (FIG. 16C) were quantified and represented as mean±SEM (5 independent images, n=5/group). *p<0.05 vs. Ctrl (SA)-tumor by unpaired t-test. FIGS. 16D-16E. Hypoxia regions were determined with a hypoxia probe (pimonidazole-HCL). Quantified results are represented as mean±SEM. p<0.005 vs. Ctrl (SA)-tumor by unpaired t-test. FIGS. 16F-16G. Fibrosis indices were determined by Masson's Trichrome C stain. Scale bars: 50 μm. Quantified results are represented as mean±SEM. p<0.005 vs. Ctrl (SA)-tumor by unpaired t-test. FIG. 16H. Immunostaining for α-SMA$^+$ myofibroblasts. FIGS. 16I-16J. Immunostaining for F4/80$^+$ macrophages. DAPI (nucleus) was co-stained. Scale bars: 100 μm. Quantified results are represented as mean±SEM. *p=0.03 vs. Ctrl (SA)-tumor by unpaired t-test.

FIG. 17A. in vivo Matrigel bioassays were performed as described in FIG. 6J. Matrigel plugs were analyzed by H&E and immunostaining for CD31 (endothelial cell marker). Scale bars: 200 μm (H&E), and 50 μm (CD31). FIG. 17B. in vitro Angiogenesis assay. MS-1 cells ($5 \times 10^4$ cells/well) were plated in triplicate on the matrigel coated 12-well plates. Tubule formation was assessed 3 hours after incubation with conditioned media derived from H293 or H293-endotrophin overexpressing cells in the presence or absence of 10B6 (10 μg/well). Scale bars: 500 μm.

FIG. 19A. FP635/PyMT mice were given TZD containing chow (supply approx. 20 mg/kg/day, rosiglitazone) or normal-diet (ND) starting at 8-weeks of age, and cisplatin (1 mg/kg) or PBS treatment was initiated at 10 weeks of age (ip., 3 times/week) over the course of tumor progression. Tumor burden was monitored with a fluorescence scanner (IVIS, Caliper life science). Quantified results are represented as mean±SD (n=8-9/group). *p=0.04, ND/CIS vs. TZD/CIS by unpaired student t-test. Metastatic burden was determined by fluorescence signals in lung tissues.

FIG. 19B. Primary cancer cells isolated from tumors in PyMT mice were implanted into WT mice. TZD were given 5 days prior to cisplatin treatment (1 mg/kg, every 5 days). Tumor volumes were determined by caliper measurement and represented as mean±SD (n=5-6/group). *p<0.05 and **p<0.001, ND/CIS vs. TZD/CIS by 2-way ANOVA. FIGS. 19C-19D. Total RNA was extracted from tumor tissues in each group. mRNA levels for collagens such as COL1A1, COL6A1, -A2, and -A3 (FIG. 19C), and EMT genes such as E-cadherin, N-cadherin, Vimentin, Snail, Slug, Twist1 and Twist2 (FIG. 19D) were determined by qRT-PCR and normalized with 36B4. Quantitative results represent mean±SD (n=7/group). *p<0.05, p<0.01, *p<0.001 ND/PBS vs. ND/CIS; ###p<0.001 ND/CIS vs. TZD/CIS by 2-way ANOVA. FIGS. 19E-19F. EMT indices were determined by immunostaining with E-Cadherin (FIG. 19E) and Vimentin (FIG. 19F). Cytokeratin (epithelial cells) and DAPI (nucleus) were co-stained. Staining positive area was quantified (multiple images, n=5/group). **p=0.014 (E) and *p=0.015 (F), ND/CIS vs. TZD/CIS by unpaired student t-test. Scale bars: 100 μm.

FIG. 20A. 10-weeks-aged PyMT and PyMT/endotrophin (PyMT/ETP) mice were given high dosage of cisplatin (2.5 mg/kg, ip., 2 times/week). Tumor growth was determined by caliper measurements. Data represent mean±SD (n=7-10/group). ***p<0.001, PyMT/CIS vs. PyMT/ETP/CIS by 2-way ANOVA. FIGS. 20B-20C. A piece of tumors taken from PyMT (Ctrl-tumor) and PyMT/endotrophin (ETP$^+$-tumor) mice were implanted into isogenic wild-type hosts. Cisplatin (1 mg/kg, ip., 2 times/week) were injected at 3-weeks post implantation for tumor progression. Tumor volume was determined by caliper measurement. Quantification (FIG. 20B) and representative images (FIG. 20C) showing increased cisplatin resistance in ETP$^+$-tumors. Data represent mean±SD (n=7-8/group). *p<0.05 vs. Ctrl-tumors by 2-way ANOVA. Representative images were taken at 70-days post implantation. Scale: 10 mm.

FIGS. 21A-21B. Schematic diagram for allografts (FIG. 21A), indicating cancer cells ($0.5 \times 10^6$ cells/mouse) were isolated from tumors in PyMT (Ctrl) and PyMT/endotrophin (ETP) mice and implanted into wild-type hosts. Host mice were given TZD (20 mg/kg) or ND diet at 10 days before implantation for tumor progression. Cisplatin (1 mg/kg, ip., every 5 days) was administered at 3-weeks post implantation. Quantification of tumor volume (FIG. 21B), showing TZD suppressed tumor growth in endotrophin$^+$-tumors. Data represent mean±SD (n=8-9/group). *p=0.05, p=0.01 and *p=0.001 Ctrl/ND vs. ETP/ND; $^{\#}$p=0.01 and $^{\#\#}$p=0.001 ETP/ND vs. ETP/TZD by unpaired student t-test. FIGS. 21C-21F. Histological analysis of tumors in allografts after cisplatin treatment. H&E staining and necrotic area quantification (FIG. 21C), showing significantly increased chemo-sensitivity in endotrophin$^+$ tumors upon combination of TZD with cisplatin. Necrotic area (*). *p<0.0001, and $^{\#\#}$p=0.0018. Vimentin staining quantification (FIG. 21D), showing decreased EMT in both Ctrl- and endotrophin$^+$-tumors by TZD. *p<0.0001 and $^{\#\#\#}$p<0.0001. Quantification of perfused lectin staining (FIG. 21E), showing the increased functional blood vessels in endotrophin$^+$-tumors was decreased by TZD. *p=0.015, p=0.001 and $^{\#\#}$p=0.0088. Masson's Trichrome C staining quantification (FIG. 21F), showing increased fibrosis in endotrophin$^+$-tumors was decreased by TZD. *p<0.0001 and $^{\#\#}$p=0.0013. Scales: 200 μm (FIG. 21A), 100 μm (FIGS. 21D-21E) and 50 μm (FIG. 21F). Statistics (*Ctrl/ND/CIS vs. Ctrl/TZD/CIS or ETP/ND/CIS; $^{\#}$ETP/ND/CIS vs. ETP/TZD/CIS) were analyzed by unpaired student t-test.

FIGS. 22A-22E. Neutralizing endotrophin activities with monoclonal antibodies sensitizes tumors to cisplatin treatment. FIG. 22A. Pieces of tumors from PyMT mice were implanted into wild-type hosts. Tumor-bearing mice were given cisplatin (1 mg/kg, ip., every 5 days) or PBS, combined with either TZD (20 mg/kg) or anti-endotrophin monoclonal antibodies (100 μg/mouse, once a week) for tumor progression. Tumor volumes were determined by caliper measurements. Data represent mean±SD (n=5/group). *p<0.05, p<0.01, *p<0.001 vs. Cisplatin by 2-way ANOVA. FIGS. 22B-22D. 4T1 ($0.5 \times 10^6$/mouse) cells were xenografted in nude mice and monitored tumor growth (FIG. 22B) and metastasis (FIG. 22C). Cisplatin (lmg/kg, every 5 days, i.p) with either 10B6 or IgG control (100 μg/mouse, once a week, i.p) was given to tumor-bearing mice from 12-days after implantation. Tumor volumes were determined by caliper measurements. Data represent mean±SD (n=5/group). *p<0.05, *p<0.001 vs. Cisplatin+IgG by 2-way ANOVA. Metastatic burden was determined by measuring metastatic lesion area in lung tissues with H&E stains. Quantified data represent mean±SD (n=5/group). *p=0.0007 and *p=0.0209 vs. CIS/10B6 by unpaired student t-test. mRNA levels for EMT markers such as vimentin, snail, slug, twist1, twist2 and S100S4 were determined by RT-qPCR (FIG. 22D). Values are normalized with 36B4 and represented as mean±SD (n=5/group). p=0.0070, p=0.0045, **p=0.0022 for vimentin, twist1, and S100A4, respectively by unpaired student t-test. FIG. 22E. Summary of study. Increased endotrophin following cisplatin treatment confers cisplatin resistance, and beneficial effects of TZDs on cisplatin sensitivity are mediated through both a suppression of endotrophin levels and its downstream pathways, including EMT, fibrosis and angiogenesis.

FIG. 24A. Two cohorts of mice (n=8) were exposed to high fat diet for 45 days after weaning. At the indicated time points (arrowheads), mice were treated with anti-endotrophin monoclonal antibodies (100 μg/mouse) or equivalent amounts of non-immune antibody. Body weights were monitored. FIG. 24B. Glucose infusion rate and FIG. 24C. Suppression of hepatic glucose efflux was measured in a hyperinsulinemic euglycemic clamp. FIG. 24D. Table of parameters measured prior and during the clamp. Significant differences as indicated by unpaired student t-test.

FIG. 26A. Two cohorts of mice (n=8) were exposed to high fat diet for 45 days after weaning. At the indicated time points (arrowheads), mice were treated with anti-endotrophin monoclonal antibodies (100 g/mouse) or equivalent amounts of non-immune antibody. Body weights were monitored. FIG. 26B. Plasma Triglycerides and FIG. 26C. plasma free fatty acids (NEFAs) and FIG. 26D. plasma cholesterol were measured. FIG. 26E. Hepatic triglycerides and FIG. 26F. hepatic cholesterol were measured. Significant differences as indicated by unpaired student t-test. FIG. 26G. Hepatic histology (H&E stain) clearly reveals differences in hepatic lipid accumulation. Scale bar=25 μm.

FIGS. 28A-28D: 10B6 mAb information. FIG. 28A: 10B6 rat hybridoma cell line expressing an anti-mouse endotrophin monoclonal antibody. FIG. 28B: transient expression of cloned 10B6 antibody as a rat/human chimera in HEK293 cells. FIG. 28C: 10B6 Kappa chain sequence (coding DNA (SEQ ID NO: 1) and amino acid (SEQ ID NO: 2) sequences) and alignment with IGKV22S7*01 (SEQ ID NO: 12). FIG. 28D: 10B6 heavy chain sequence (coding DNA (SEQ ID NO: 3) and amino acid (SEQ ID NO: 4) sequences) and alignment with IGHV1S12*01 (SEQ ID NO: 13).

DETAILED DESCRIPTION

Figure 27:
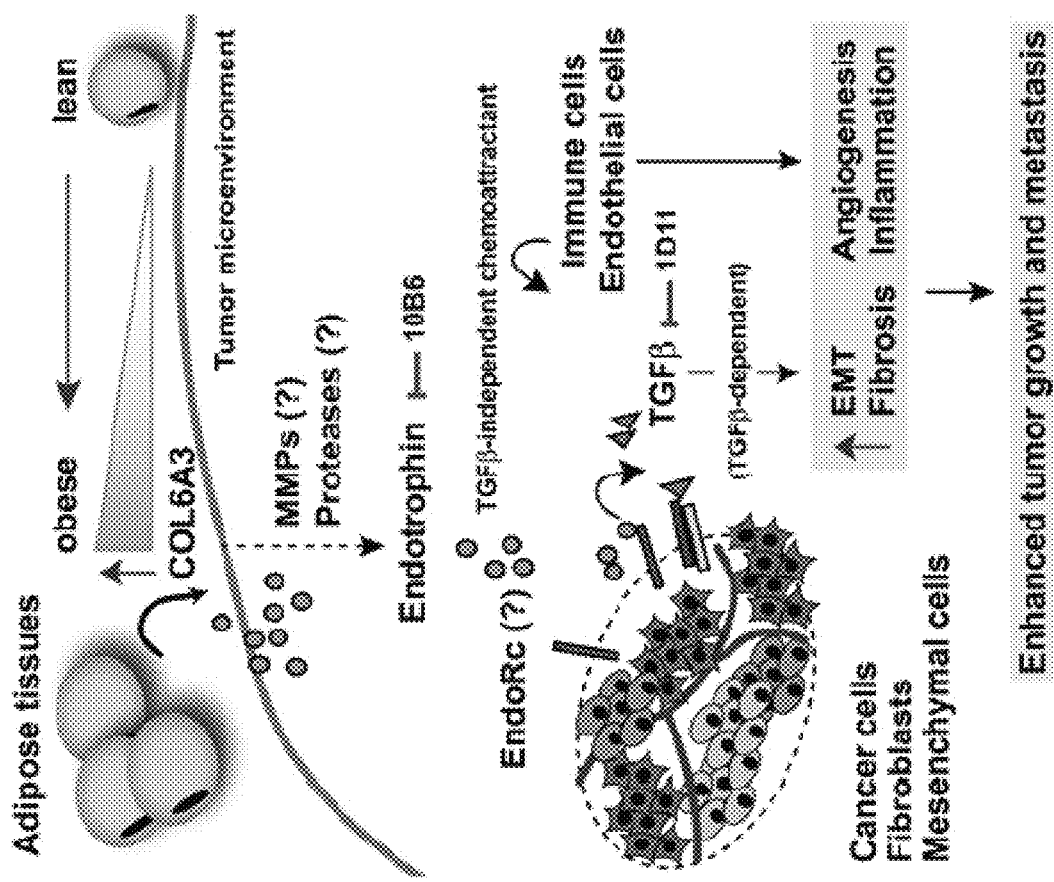
FIG. 27: Endotrophin-mediated changes in the tumor stroma. Adipocyte-derived COL6A3 levels are increased during obesity. Endotrophin is cleaved from the COL6A3 parent chain within the tumor microenvironment. Endotrophin potentiates TGFβ-dependent epithelial-mesenchymal transition (EMT) and fibrosis and displays chemoattractive activity, recruiting endothelial cells and macrophages, leading to enhanced angiogenesis and chronic inflammation. All of these activities induced by endotrophin synergistically lead to enhanced tumor growth and metastasis. Either the endotrophin neutralizing monoclonal antibody (10B6) or the TGFβ antagonizing monoclonal antibody (1D11) differentially attenuate a subset of endotrophin effects. EndoRc: endotrophin receptor.

Collagen VI (COL6, encoded by the COL6A1, COL6A2, and COL6A3 genes) is an extracellular matrix protein that forms a microfilamentous network in various connective tissues, including skeletal muscle, cartilage, skin and adipose tissue. Among the various tissues, adipose tissue is by far the most abundant source of COL6 microfilaments. Clinically, mutations in COL6 develop mild muscle myopathies (such as Bethlem myopathy and Ullrich congenital muscular dystrophy), with symptoms of muscle weakness and apoptosis combined with joint hyperlaxity and contracture. A genetically engineered mouse model, deficient in COL6 microfilament formation and secretion, has been widely used to investigate the roles of COL6 under physiological and pathological conditions. COL6 deficiency in mice leads to the development of muscle dystrophies resembling Bethlem myopathy in man. In the area of tumor biology, COL6 has been identified as a tumor-promoting factor abundantly produced and released from adipocytes. Subsequent analysis of the COL6 functional null mice bred into the murine MMTV-PyMT mammary tumor model (mouse mammary tumor virus-polyoma middle T antigen) showed a significant attenuation of early onset mammary tumor progression. Specifically, the carboxyl-terminal domain of the COL6A3 chain is massively upregulated in the malignant tumors of human patients compared to the remaining part of COL6A3 chain. As follow-up analysis demonstrated, the cleavage product from the carboxyl-terminus of the COL6A3 chain (referred to as endotrophin) accounts for the tumor-promoting effects associated with COL6. Ectopic expression of the isolated endotrophin fragment within the tumor microenvironment of MMTV-PyMT mice drives an increase of both primary tumor growth and pulmonary metastasis through an enhancement of the expansion of the tumor stroma. Additional prominent effects associated with endotrophin overexpression in the tumor stroma include an increase in fibrosis, angiogenesis and inflammation through increased fibrogenesis, a stimulation of epithelial-mesenchymal transition (EMT) and chemokine activities; these are well-established stromal phenomena that support aggressive traits of tumors (FIG. 27). Indeed, neutralizing monoclonal antibodies against endotrophin suppress tumor growth and reduce metastatic growth in MMTV-PyMT mice. EMT of tumors conveys metastatic traits and multiple drug resistances to cancer cells. Since endotrophin is a potent stimulator of EMT, it suggests that the neutralization of endotrophin may lend itself to enhance chemosensitivity in combination with conventional therapeutic regimens, though this remains to be directly shown.

Adipose tissue is a crucial organ for the maintenance of whole body energy homeostasis, and also a major source of COL6. The roles of COL6 in metabolic homeostasis were examined even without a tumor burden. Metabolic characterization of the COL6A1 functional null mice bred with a genetically obese animal model, the ob/ob mouse, reveals that COL6 deficiency improves systemic metabolic profiles, including enhanced insulin sensitivity and glucose metabolism. This is likely due to a number of changes, but the reduced fibrotic stress commonly seen in hypertrophic adipose tissues in obese status is likely to be a contributing factor. COL6 is upregulated in obese and dysfunctional adipose tissue, and anti-diabetic treatment regimens lead to a suppression of COL6 expression. Tumor lesions in the microenvironment lead to a further local enrichment of endotrophin, either through stimulation of syntheses and/or cleavage of endotrophin from the mature protein, or through an induction of production within the tumor lesions themselves. As such, endotrophin is likely to constitute one of the risk factors that mediate the more aggressive lesion growth and worse prognosis seen in patients with higher body mass indices (BMIs). More importantly, it is likely that endotrophin plays a pro-fibrotic and pro-inflammatory role in a number of additional tissues, even in the absence of a tumor challenge. This may be relevant for adipose tissues, liver and kidney, all tissues that are prone to fibrosis and chronic inflammation under pathological conditions. Therefore, inhibition of endotrophin activity under such pathological conditions is likely to be associated with clinical improvements.

Endotrophin (ETP) is the major mediator of the COL6-mediated tumor effects. ETP augmented fibrosis, angiogenesis, and inflammation through recruitment of macrophages and endothelial cells. Moreover, ETP expression was associated with aggressive mammary tumor growth and high metastatic growth. These effects were partially mediated through enhanced TGF-β signaling, which contributes to tissue fibrosis and epithelial-mesenchymal transition (EMT) of tumor cells. The results highlight the crucial role of ETP as an obesity-associated factor that promotes tumor growth in the context of adipocyte interactions with tumor and stromal cells.

In addition, relationship between thiazolidinediones (TZDs), endotrophin and cisplatin resistance was examined in the context of a mammary tumor model. COL6A3 levels are significantly increased in response to cisplatin exposure in tumors. Endotrophin, in turn, causes cisplatin resistance. The effects of endotrophin can be bypassed by administering TZDs in wild-type mice (leading to a downregulation of endotrophin). This sensitizes tumors to cisplatin partly through the suppression of endotrophin-induced epithelial-mesenchymal transition (EMT). Therefore, the chemosensitization obtained with TZDs is achieved through a downregulation of endotrophin. Treatment with an endotrophin neutralizing monoclonal antibody in combination with cisplatin completely inhibits tumor growth of allografts of MMTV-PyMT tumors. Combined, the data suggest that endotrophin levels are a strong prognostic marker for the effectiveness of the combination therapy of TZDs with cisplatin. Furthermore, neutralization of endotrophin activity dramatically improves the therapeutic response to combination therapy.

I. Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

As used herein, the following terms and phrases are intended to have the following meanings:

The articles "a" and "an" are used herein to refer to one or to more than one (i.e., to at least one) of the grammatical object of the article. By way of example, "an element" means one element or more than one element.

As used herein, the term "about" means within 20%, more preferably within 10% and most preferably within 5%.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single antibody; (vi) the dAb fragment which consists of a VH domain; (vii) isolated CDR regions; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) "linear antibodies" comprising a pair of tandem Fd segments (VH-CH1-VH-CH1) which, together with complementary light chain polypeptides, form a pair of antigen binding regions.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

A "constant region" of an antibody refers to the constant region of the antibody light chain or the constant region of the antibody heavy chain, either alone or in combination. The constant regions of the light chain (CL) and the heavy chain (CH1, CH2 or CH3, or CH4 in the case of IgM and IgE) confer important biological properties such as secretion, transplacental mobility, Fc receptor binding, complement binding, and the like. By convention the numbering of the constant region domains increases as they become more distal from the antigen binding site or amino-terminus of the antibody.

The term "heavy chain" as used herein refers to the larger immunoglobulin subunit which associates, through its amino terminal region, with the immunoglobulin light chain. The heavy chain comprises a variable region (VH) and a constant region (CH). The constant region further comprises the CH1, hinge, CH2, and CH3 domains. In the case of IgE, IgM, and IgY, the heavy chain comprises a CH4 domain but does not have a hinge domain. Those skilled in the art will appreciate that heavy chains are classified as gamma, mu, alpha, delta, or epsilon ($\gamma$, $\mu$, $\alpha$, $\delta$, $\epsilon$), with some subclasses among them (e.g., $\gamma$1-$\gamma$4). It is the nature of this chain that determines the "class" of the antibody as IgG, IgM, IgA IgG, or IgE, respectively. The immunoglobulin subclasses (isotypes), e.g., IgG1, IgG2, IgG3, IgG4, IgA1, etc. are well characterized and are known to confer functional specialization.

The term "light chain" as used herein refers to the smaller immunoglobulin subunit which associates with the amino terminal region of a heavy chain. As with a heavy chain, a light chain comprises a variable region (VL) and a constant region (CL). Light chains are classified as either kappa or lambda ($\kappa$, $\lambda$). A pair of these can associate with a pair of any of the various heavy chains to form an immunoglobulin molecule. Also encompassed in the meaning of light chain are light chains with a lambda variable region (V-lambda) linked to a kappa constant region (C-kappa) or a kappa variable region (V-kappa) linked to a lambda constant region (C-lambda).

As used herein, "neutralize" and permutations thereof refer to an agent that is capable of inhibiting (partially or completely), reducing or abolishing an activity of a target (e.g., endotrophin).

"Nucleic acid," "nucleic acid sequence," "oligonucleotide," "polynucleotide" or other grammatical equivalents as used herein means at least two nucleotides, either deoxyribonucleotides or ribonucleotides, or analogs thereof, covalently linked together. Polynucleotides are polymers of any length, including, e.g., 20, 50, 100, 200, 300, 500, 1000, 2000, 3000, 5000, 7000, 10,000, etc. A polynucleotide described herein generally contains phosphodiester bonds, although in some cases, nucleic acid analogs are included that may have at least one different linkage, e.g., phosphoramidate, phosphorothioate, phosphorodithioate, or O-methylphophoroamidite linkages, and peptide nucleic acid backbones and linkages. Mixtures of naturally occurring polynucleotides and analogs can be made; alternatively, mixtures of different polynucleotide analogs, and mixtures of naturally occurring polynucleotides and analogs may be made. The following are non-limiting examples of polynucleotides: a gene or gene fragment, exons, introns, messenger RNA (mRNA), transfer RNA, ribosomal RNA, ribozymes, cDNA, cRNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form. A polynucleotide is composed of a specific sequence of four nucleotide bases: adenine (A), cytosine (C), guanine (G), thymine (T), and uracil (U) for thymine when the polynucleotide is RNA. Thus, the term "polynucleotide sequence" is the alphabetical representation of a polynucleotide molecule. Unless otherwise indicated, a particular polynucleotide sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

The terms "peptide," "polypeptide" and "protein" used herein refer to polymers of amino acid residues. These terms also apply to amino acid polymers in which one or more amino acid residues is an artificial chemical mimetic of a corresponding naturally occurring amino acid, as well as to naturally occurring amino acid polymers, those containing modified residues, and non-naturally occurring amino acid polymers. In the present case, the term "polypeptide" encompasses an antibody or a fragment thereof.

A "variable region" of an antibody refers to the variable region of the antibody light chain or the variable region of the antibody heavy chain, either alone or in combination. The variable regions of both the light (VL) and heavy (VH) chain portions determine antigen recognition and specificity. VL and VH each consist of four framework regions (FR) connected by three complementarity determining regions (CDRs) also known as hypervariable regions. The CDRs complement an antigen's shape and determine the antibody's affinity and specificity for the antigen. There are six CDRs in both VL and VH. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (the Kabat numbering scheme; see Kabat et al., Sequences of Proteins of Immunological Interest (5th ed., 1991, National Institutes of Health, Bethesda Md.)); and (2) an approach based on crystallographic studies of antigen-antibody complexes (the Chothia numbering scheme which corrects the sites of insertions and deletions (indels) in CDR-L1 and CDR-H1 suggested by Kabat; see Al-lazikani et al. (1997) J. Molec. Biol. 273:927-948)). Other numbering approach or scheme can also be used. As used herein, a CDR may refer to CDRs defined by either approach or by a combination of both approaches or by other desirable approaches. In addition, a new definition of highly conserved core, boundary and hyper-variable regions can be used.

Other terms used in the fields of recombinant nucleic acid technology, microbiology, immunology, antibody engineering, and molecular and cell biology as used herein will be generally understood by one of ordinary skill in the applicable arts.

II. Antibodies and Modifications of Antibodies

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557, incorporated herein by reference). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024, each incorporated herein by reference.

In further embodiments, antibody molecules, or fragments thereof may be used to target some marker on the surface of a target cell. The antibody alone may serve as an effector of therapy or it may recruit other cells to actually affect cell killing. The antibody may also be conjugated to a drug or toxin (e.g., chemotherapeutic, radionuclide, ricin A chain, cholera toxin, pertussis toxin, etc.) and thus may merely serve as a targeting agent.

In certain embodiments, are antibody conjugates. The conjugate can be, for example, a specific binding agent (such as an antibody) of the invention conjugated to other proteinatious, carbohydrate, lipid, or mixed moiety molecule(s). Such antibody conjugates include, but are not limited to, modifications that include linking it to one or more polymers. In certain embodiments, an antibody is linked to one or more water-soluble polymers. In certain such embodiments, linkage to a water-soluble polymer reduces the likelihood that the antibody will precipitate in an aqueous environment, such as a physiological environment. In certain embodiments, a therapeutic antibody is linked to a water-soluble polymer. In certain embodiments, one skilled in the art can select a suitable water-soluble polymer based on considerations including, but not limited to, whether the polymer/antibody conjugate will be used in the treatment of a patient and, if so, the pharmacological profile of the antibody (e.g., half-life, dosage, activity, antigenicity, and/or other factors).

In further embodiments, the conjugate can be, for example, a cytotoxic agent. Cytotoxic agents of this type may improve antibody-mediated cytotoxicity, and include such moieties as cytokines that directly or indirectly stimulate cell death, radioisotopes, chemotherapeutic drugs (including prodrugs), bacterial toxins (e.g., *pseudomonas* exotoxin, diphtheria toxin, etc.), plant toxins (e.g., ricin, gelonin, etc.), chemical conjugates (e.g., maytansinoid toxins, calechaemicin, etc.), radioconjugates, enzyme conjugates (e.g., RNase conjugates, granzyme antibody-directed enzyme/prodrug therapy), and the like. In one aspect, the cytotoxic agent can be "attached" to one component of a bi-specific or multi-specific antibody by binding of this agent to one of the alternative antigen recognition sites on the antibody. As an alternative, protein cytotoxins can be expressed as fusion proteins with the specific binding agent following ligation of a polynucleotide encoding the toxin to a polynucleotide encoding the binding agent. In still another alternative, the specific binding agent can be covalently modified to include the desired cytotoxin.

In additional embodiments antibodies, or fragments thereof, can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising an antibody molecule, wherein the molecule preferably further comprises a reporter group selected from the group consisting of a radiolabel, a fluorescent label, an enzyme, a substrate, a solid matrix, and a carrier. Such labels are well known to those of skill in the art, e.g., biotin labels are particularly contemplated. The use of such labels is well known to those of skill in the art and is described in, e.g., U.S. Pat. No. 3,817,837; U.S. Pat. No. 3,850,752; U.S. Pat. No. 3,996,345 and U.S. Pat. No. 4,277,437, each incorporated herein by reference. Other labels that will be useful include but are not limited to radioactive labels, fluorescent labels and chemiluminescent labels. U.S. Patents concerning use of such labels include for example U.S. Pat. No. 3,817, 837; U.S. Pat. No. 3,850,752; U.S. Pat. No. 3,939,350 and U.S. Pat. No. 3,996,345. Any of the peptides of the present invention may comprise one, two, or more of any of these labels.

III. Examples

Example 1

Adipocyte-Derived Endotrophin Promotes Malignant Tumor Progression

Breast cancer is the most common malignancy found in women. Among a number of risk factors, obesity ranks high and contributes significantly to postmenopausal breast cancer risk. Epidemiological evidence supports a tight association among obesity, cancer incidence, and mortality. Hence, the adipocyte, as a major constituent of the mammary tumor stroma, is a likely contributor to tumor growth. The interactions between malignant epithelial cancer cells and the surrounding stromal cells have a profound impact on tumor physiology, including cell growth, survival, metastasis, and recurrence. Numerous studies have documented contributions of stromal cells to tumor growth, through factors released from tumor-associated macrophages, fibroblasts, and endothelial cells. However, less is known about adipocyte factors that dominate the tumor microenvironment; such factors are either permissive or, in some cases, actively contributing to tumor cell growth.

The adipocyte is an established endocrine organ, secreting various signaling molecules—such as adipokines, chemokines, and extracellular matrix (ECM) constituents—in response to nutritional or hormonal stimuli. Adipocyte-derived factors involved in tumor progression include proteins such as adiponectin, leptin, TNF-α, monocyte chemotactic protein-1 (MCP-1), IL-6, and ECM components that control tumor cell behavior within the tumor microenvironment. Key signaling networks associated with cell proliferation, angiogenesis, inflammation, and apoptosis are activated by adipokines; these include PI3K, ERK1/2, STAT3, and NF-κB. Such pathways are frequently activated in tumor tissues.

Collagen type VI (COL6; encoded by Col6a1, Col6a2, and Col6a3) is ubiquitously expressed throughout connective tissues, such as blood vessels, muscle, lung, and skin. However, adipose tissue (AT) is the most abundant source of COL6. COL6 is a large collagenous glycoprotein composed of 3 chains, α1, α2, and α3, that are intracellularly assembled from heterotrimeric monomers to tetramers. Once secreted into the extracellular space, COL6 tetramers associate into microfibrils. Subsequently, the carboxyterminal C5 domain of the α3 chain is proteolytically cleaved off from the COL6 microfibrils. However, the details of this cleavage event and the functional role of the cleavage product, the C5 domain, remain unknown, with the exception that the C5 domain plays an important structural role for COL6 microfibril formation. Adipocyte-derived COL6 is a tumor-promoting factor in the background of the mammary tumor virus—polyoma middle T antigen (MMTV-PyMT) mammary tumor mouse model (referred to herein as PyMT mice). Notably, the carboxyterminal domain of the COL6α3 chain is stable and highly enriched in human breast cancer specimens compared with full-length COL6α3. However, prior to this study, it remains unknown whether the cleaved C5 fragment of the COL6α3 chain, referred to herein as endotrophin (ETP), participates in mammary tumor progression.

The studies herein examined whether ETP regulates tumor cell growth and metastasis on its own, independent of other COL6 subunits, or the remainder of the COL6α3 chain. It is widely appreciated that the ECM provides mechanical and structural support within the microenvironment.

In addition, ECM-derived proteolytic fragments can directly activate various signaling pathways, influencing events in neighboring cells that express ECM receptors, such as integrins. To better define the role of ETP in tumor progression within the local tumor microenvironment, independent of the rest of the COL6 complex, transgenic mice that harbor ETP with a signal sequence was generated under the control of the mammary epithelial specific MMTV promoter. MMTV-ETP transgenic mice were characterized either independently (referred to herein as ETP mice), in the background of PyMT mice (PyMT/ETP mice), or with tumor implantations into isogenic mice. These mouse models were used in combination with specific ETP neutralizing antibodies to evaluate their therapeutic potential. The aim of the studies was to identify and define mechanisms responsible for the effects of COL6 on tumor growth and metastasis and further establish which signaling pathways play critical roles mediating the potent ETP effects.

Results

ETP is Abundant in Tumor Tissues.

Figures 1A, 1B, 1C, 1D, 1E, 1F, 1G:
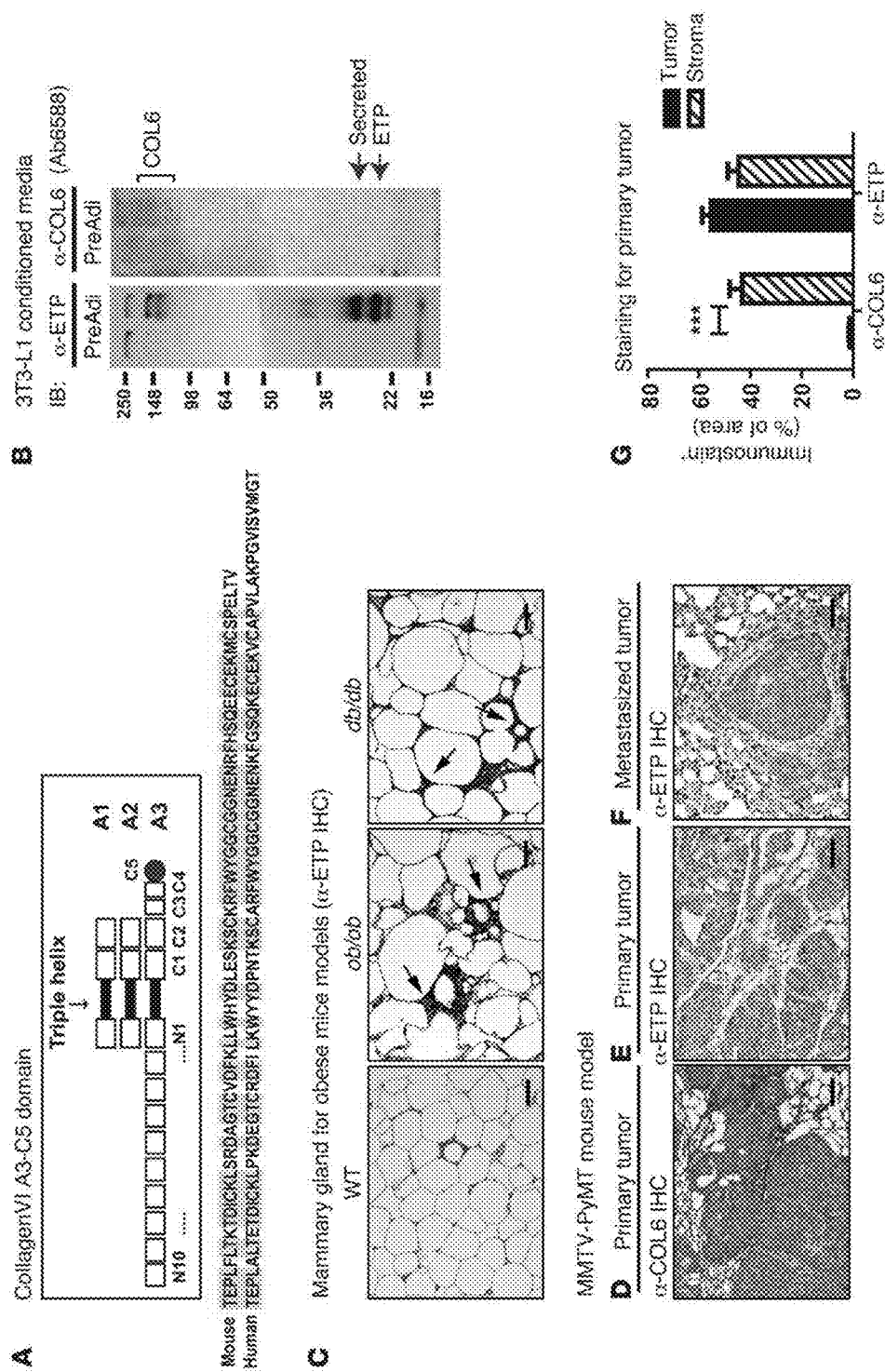
FIGS. 1A-1G: Expression profiles of ETP.
Figures 2A, 2B, 2C, 2D:
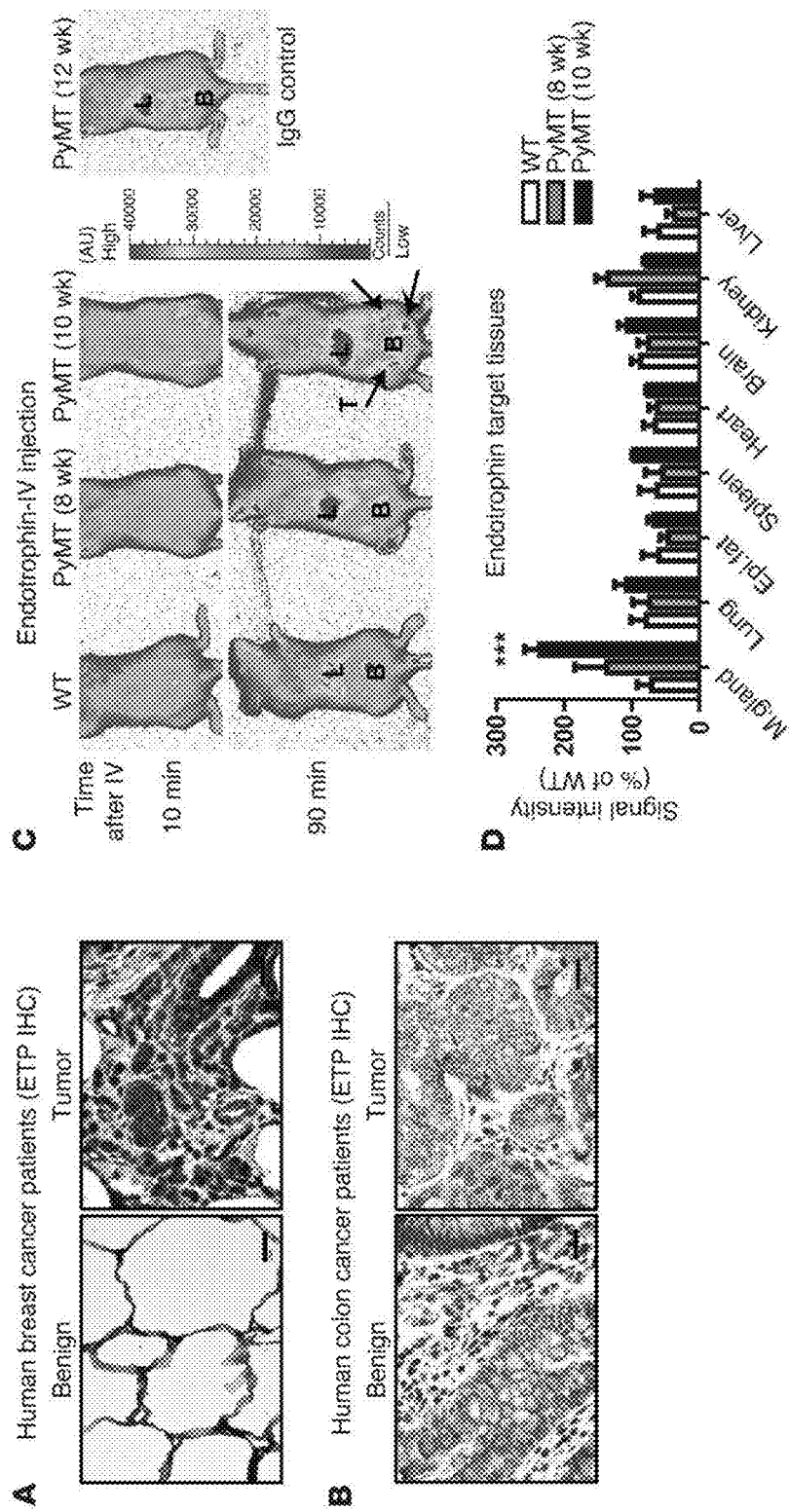
FIGS. 2A-2D: ETP levels in human cancer specimens and its target tissues.
Figures 9A, 9B, 9C:
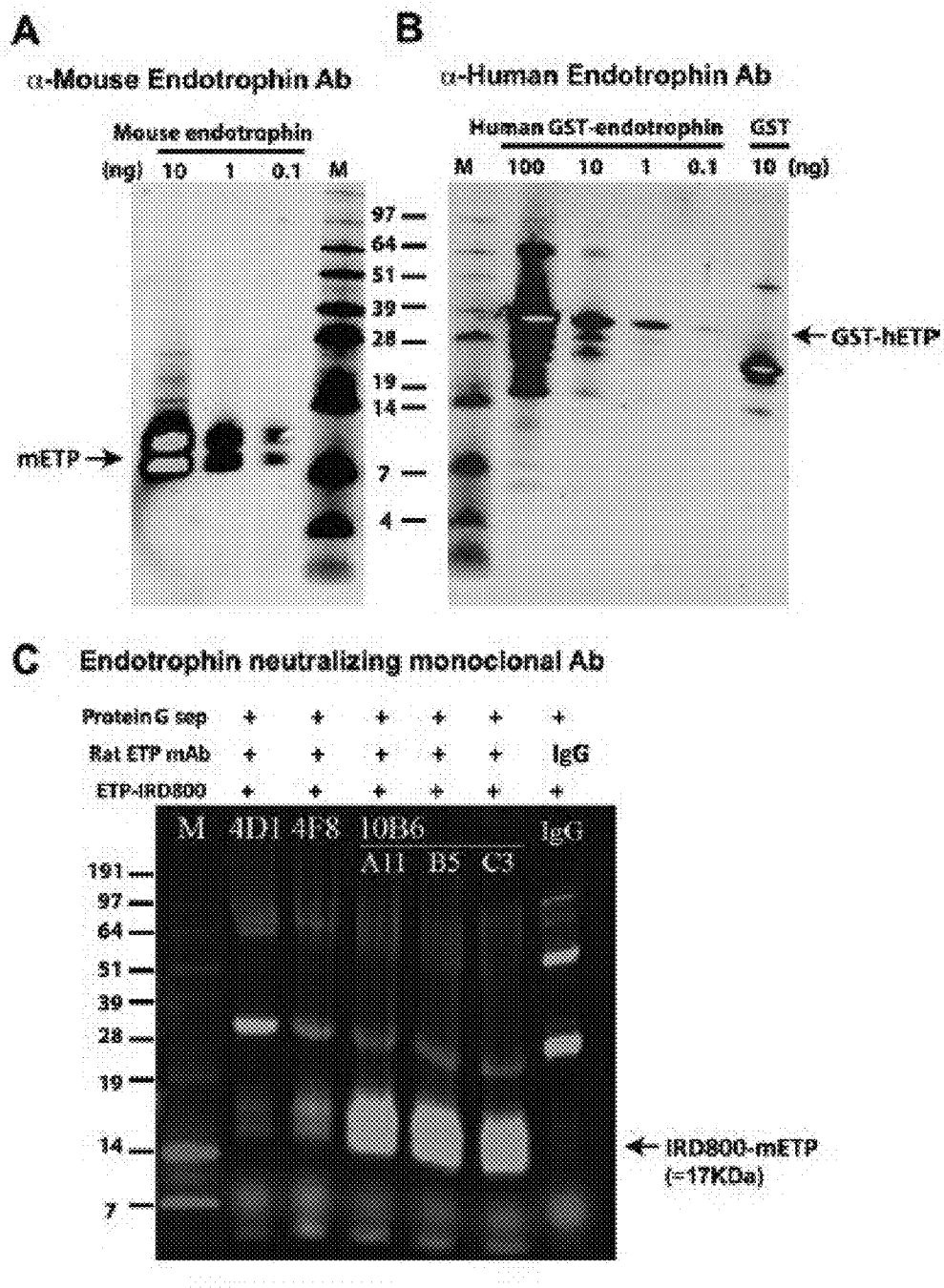
FIGS. 9A-9C. Generation of endotrophin-specific antibodies.
Figures 10A, 10B:
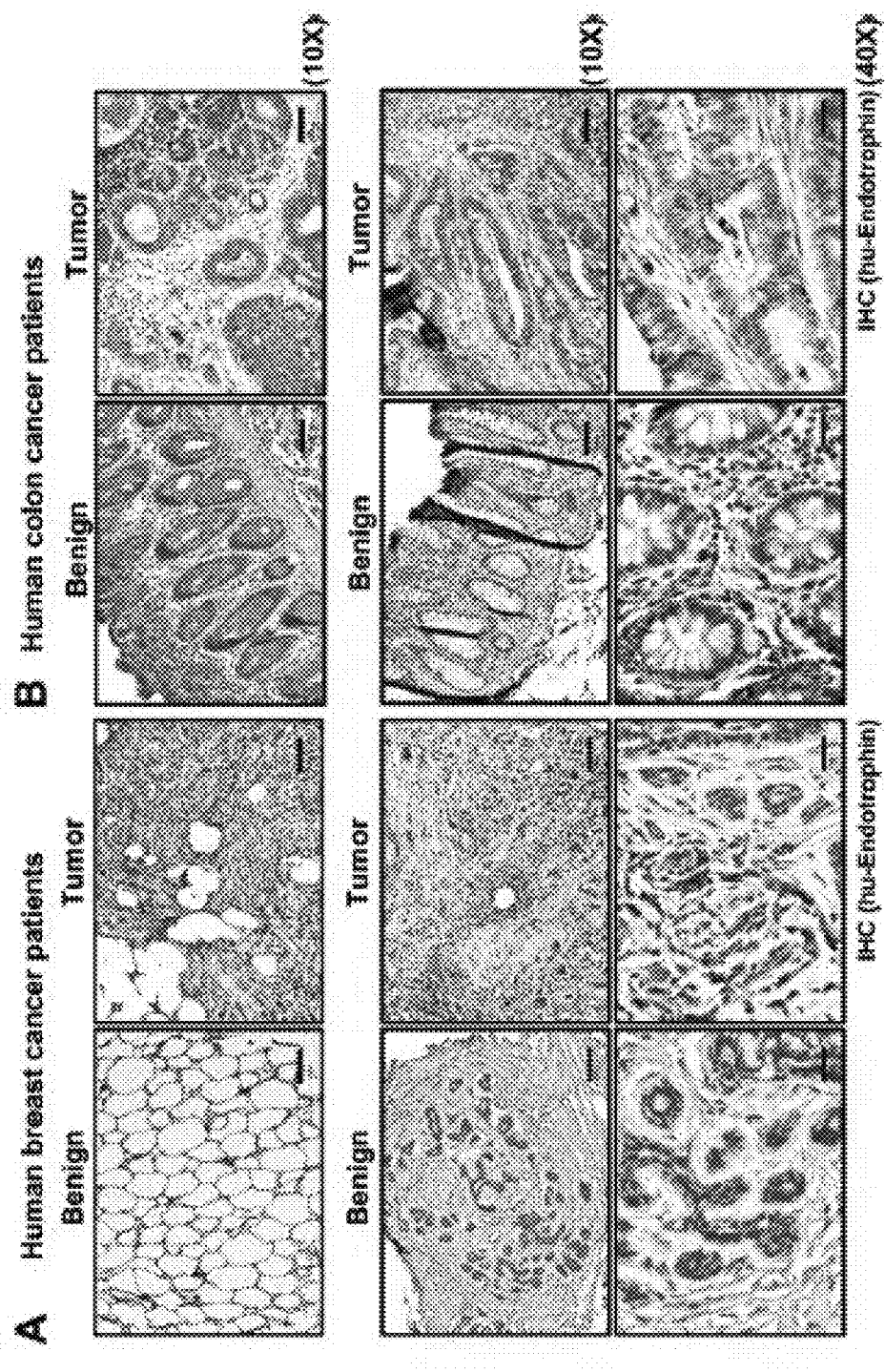
FIGS. 10A-10F. Endotrophin expression levels in various tissues.
Figures 10C, 10D, 10E, 10F:
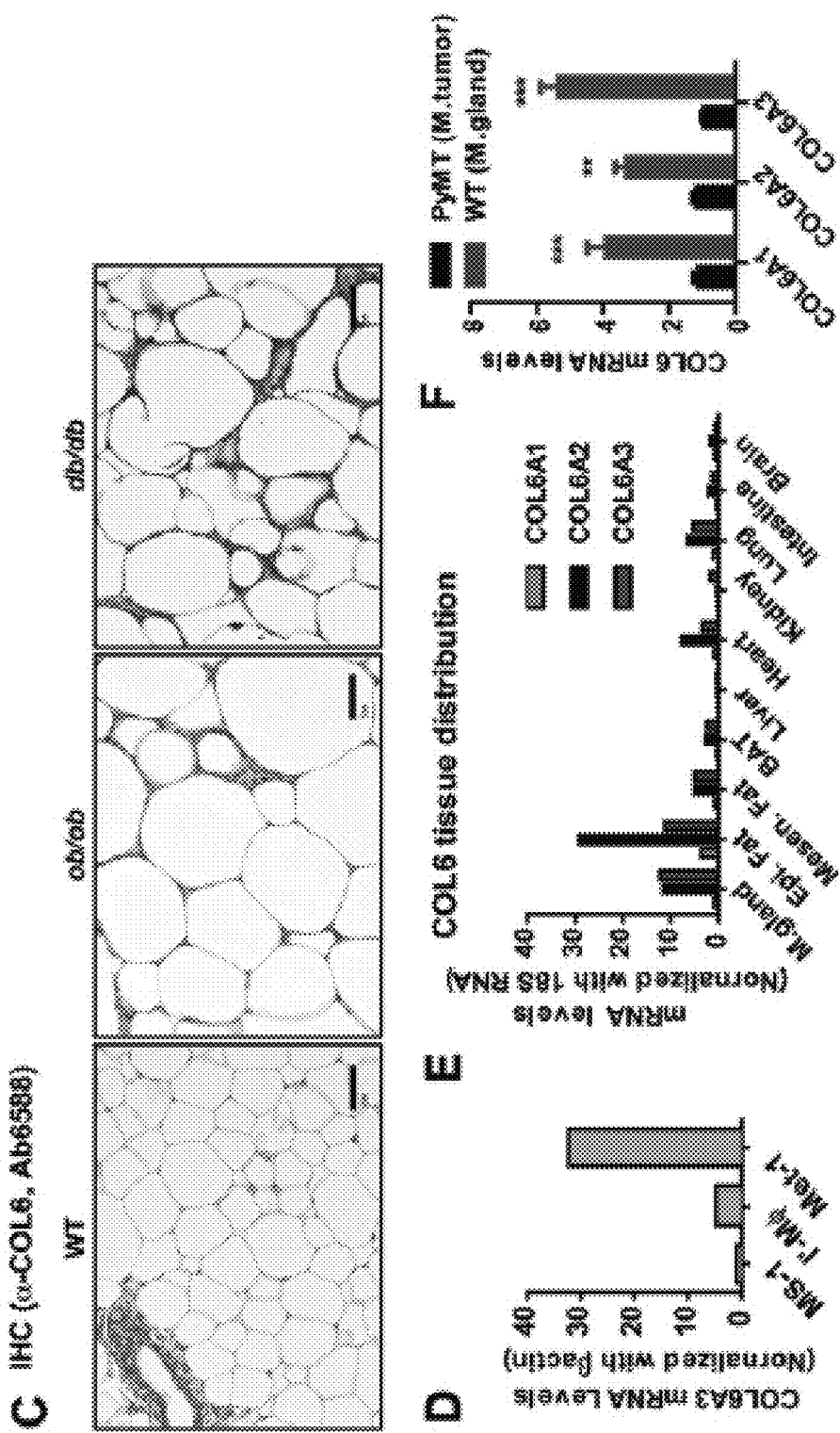

To further investigate a role of COL6 in tumor progression, particularly in the context of ETP, polyclonal antibodies specific for either mouse or human ETP domains were generated (FIGS. 9A and 9B); a substantial degree of conservation was preserved between the species (FIG. 1A). Similar to holo-COL6 levels, secreted ETP was readily identified in conditioned media of 3T3-L1 adipocytes, but not 3T3-L1 fibroblasts (FIG. 1B). Consistent with this observation, high ETP levels in the AT of obese animals were observed, such as ob/ob and db/db mice, compared with lean controls (FIG. 1C). Interestingly, ETP prominently accumulated in obesity-associated crown-like structures of AT (FIG. 1C, arrows), prominent structures in dysfunctional adipocytes in which infiltrating macrophages mediate chronic inflammatory responses. In contrast, a holo-COL6-specific antibody primarily highlighted a signal at the periphery of adipocytes (FIG. 10C). Immunostaining of tumor tissues from PyMT mice with anti-holo-COL6 showed that entire tumor lesions were surrounded by COL6 fibrils, with weaker staining observed in AT (FIGS. 1D and 1G). Interestingly, cleaved soluble ETP freely diffused in the microenvironment and accumulated on primary tumor lesions of PyMT mice in a paracrine manner (FIGS. 1E and 1G). Of note, ETP was less prominent on metastasized tumors in the lung (FIG. 1F), which suggests that ETP levels on tumor cells may critically depend on the presence of local adipocytes to supply ETP. Histological analysis of human breast tumor tissues indicated that ETP was highly abundant on both epithelial cancer cells and various stromal cells within the tumor microenvironment, with a much lower signal seen in benign tissues (FIG. 2A and FIG. 10A). In the mouse, ETP was highly expressed in the mammary epithelial cancer cell Met-1, relative to other cell types, such as the endothelial cell line MS-1 or primary macrophages (FIG. 10D). This suggests that cancer cells can express ETP, even though AT was the major source for COL6 among various WT tissues and PyMT tumor tissue (FIGS. 10E and 10F). ETP overexpression was not restricted to mammary cancer cells. Similar increases in ETP in other tumor sections was observed, such as in human colon cancers, which showed significantly higher ETP levels than those in benign tissues (FIG. 2B and FIG. 10B). ETP may therefore be a player in several other tumor settings and may play a crucial role in cancer cell behavior through both paracrine and autocrine signaling.

To identify the tissues that are critical targets for ETP in circulation, infrared fluorescent dye-labeled (IRD-800) recombinant ETP protein was injected into PyMT mice through tail vein injection. The signal distribution in these tumor-bearing mice was compared with that of WT mice. The in vivo fate of the labeled ETP was monitored by fluorescence scanning. A high fluorescence signal was observed in liver and bladder of all mice due to clearance. However, ETP was predominantly observed in tumor lesions compared with control-labeled IgGs (FIG. 2C). As determined by quantification, ETP was highly enriched in mammary tumor tissues relative to mammary glands of WT mice (FIG. 2D).

Elevated Local ETP Levels Convey Higher Antiapoptotic and Promitotic Indices in Normal Mammary Epithelial Cells.

Figures 3A, 3B, 3C, 3D, 3E:
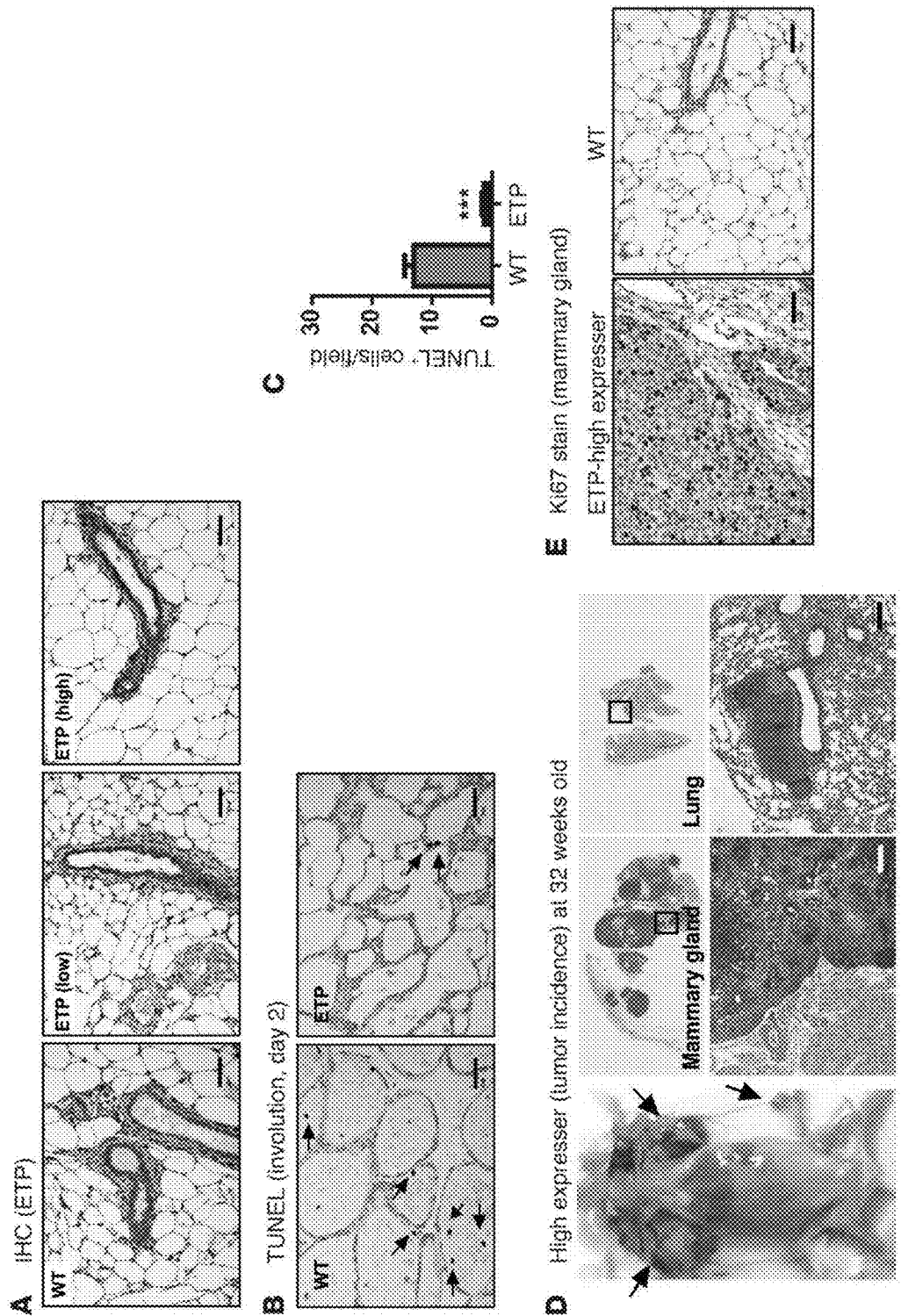
FIGS. 3A-3E: Transgenic mice expressing ETP under the MMTV promoter.
Figures 11A, 11B, 11C, 11D, 11E:
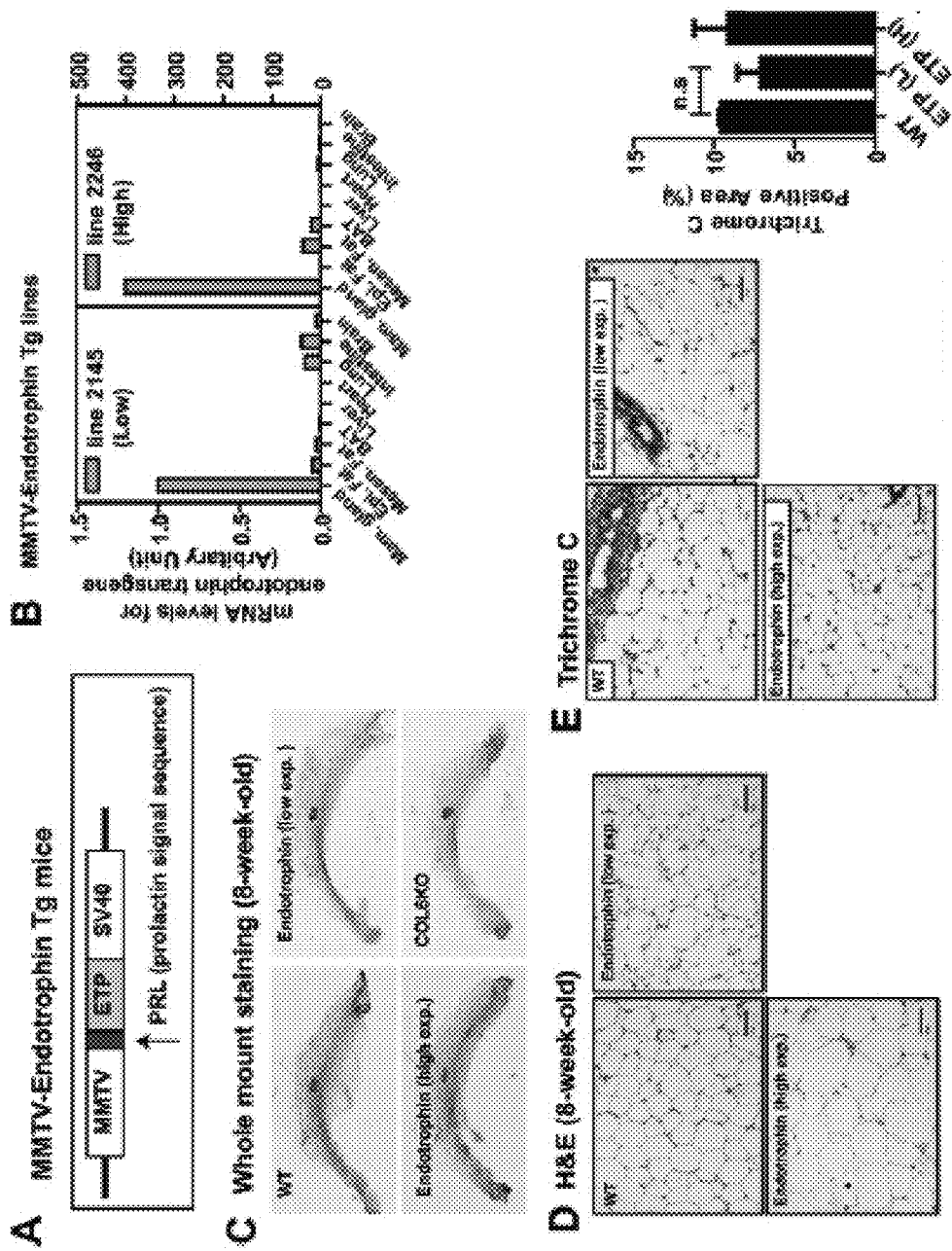
FIGS. 11A-11G. Generation of the MMTV-endotrophin transgenic mice.

To directly examine the role of ETP in mammary tumor growth, a gain-of-function approach was used with a transgenic mouse model expressing ETP under the control of MMTV promoter to elevate local ETP levels within the mammary gland. To achieve efficient ETP secretion, a prolactin signal sequence was inserted in-frame 5' to the region encoding the mouse ETP sequence (FIG. 11A). ETP transgene levels were highly upregulated in a high-expressing line compared with the more modest overproduction of other low-expressing lines (FIG. 11B). Immunostaining with antibodies against ETP indicated that ETP was enriched in mammary ductal epithelium in both transgenic mouse lines relative to WT (FIG. 3A).

Figures 11F, 11G:
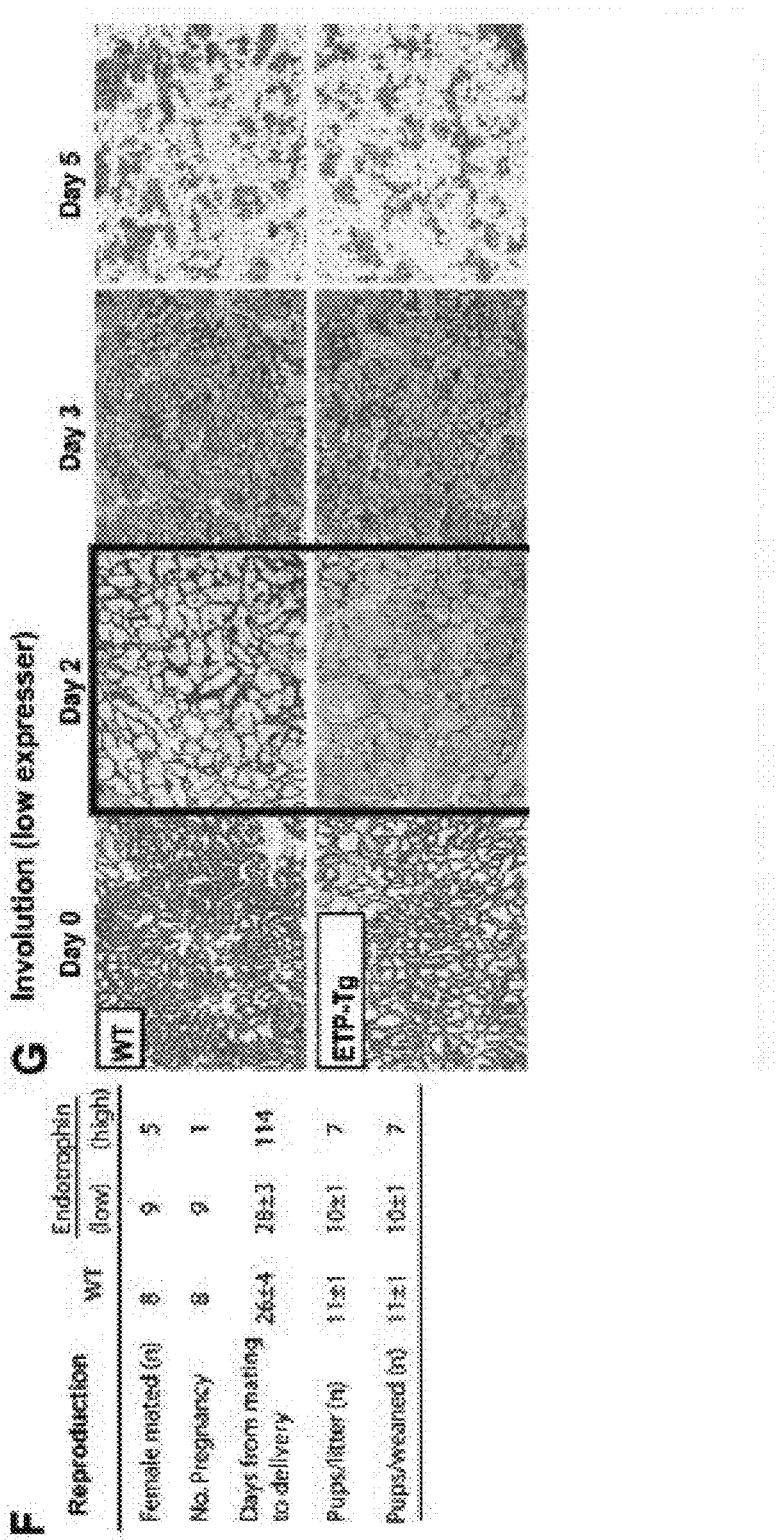

Assessment of mammary gland development in ETP mice is critical to evaluate the roles of ETP in mammary tumor progression, as most primary mammary tumors originate from mammary ductal or intraductal epithelial cells. Histological analysis—including whole-mount, H&E, and Masson's Trichrome C staining—of mammary glands showed that ductal epithelial growth and the degree of fibrosis in both ETP transgenic lines was comparable to those in WT mice (FIGS. 11C-11E). The final stages of mammary gland development are completed upon pregnancy, lactation, and involution. The high-expressing ETP line displayed a deficiency in fertility (FIG. 11F) and reduced locomotion (data not shown); these secondary effects of elevated ETP levels may make the interpretation of local findings within the mammary gland more challenging. The focus was therefore placed on the low-expressing line and examined the process of involution. In this process, the secretory epithelial cells undergo apoptosis with concomitant redifferentiation of adipocytes, thereby reconstituting prepregnancy status after weaning Involution was delayed at an early stage of the process in ETP mice (FIG. 11G), along with a reduction in apoptosis in secretory epithelial cells (FIGS. 3B and 3C). This suggests that ETP acts as a potent antiapoptotic factor in this setting. Delays in the process of involution frequently resemble the prolonged survival of epithelial cells in a cancer setting. Nevertheless, ETP mice did eventually revert back to prepregnancy status, albeit with delayed kinetics (FIG. 11G).

Abnormal developmental cues can induce and promote a cancerous transformation of mammary epithelial cells. Indeed, several mice with high ETP expression spontaneously developed tumors (FIG. 3D). Spontaneous tumor formation in low ETP expressers or WT mice up to 18 months of age was not observed (data not shown). Immunostaining with Ki67 showed that cell proliferation was increased in hyperplastic lesions of mammary tissue in the high-expressing mice (FIG. 3E), which suggests that high levels of ETP alone are sufficient to augment promitogenic activity. No lesions were observed in WT mice, and hence no detectable mitogenic activity or Ki67 signal was evident (FIG. 3E). Further efforts were directed toward the physiologically more relevant lower-expressing ETP line, since these mice develop the mammary ductal epithelium completely normally and overexpress ETP only locally.

ETP Augments Tumor Growth and Metastasis in PyMT Mice.

Figures 4A, 4B, 4C, 4D, 4E:
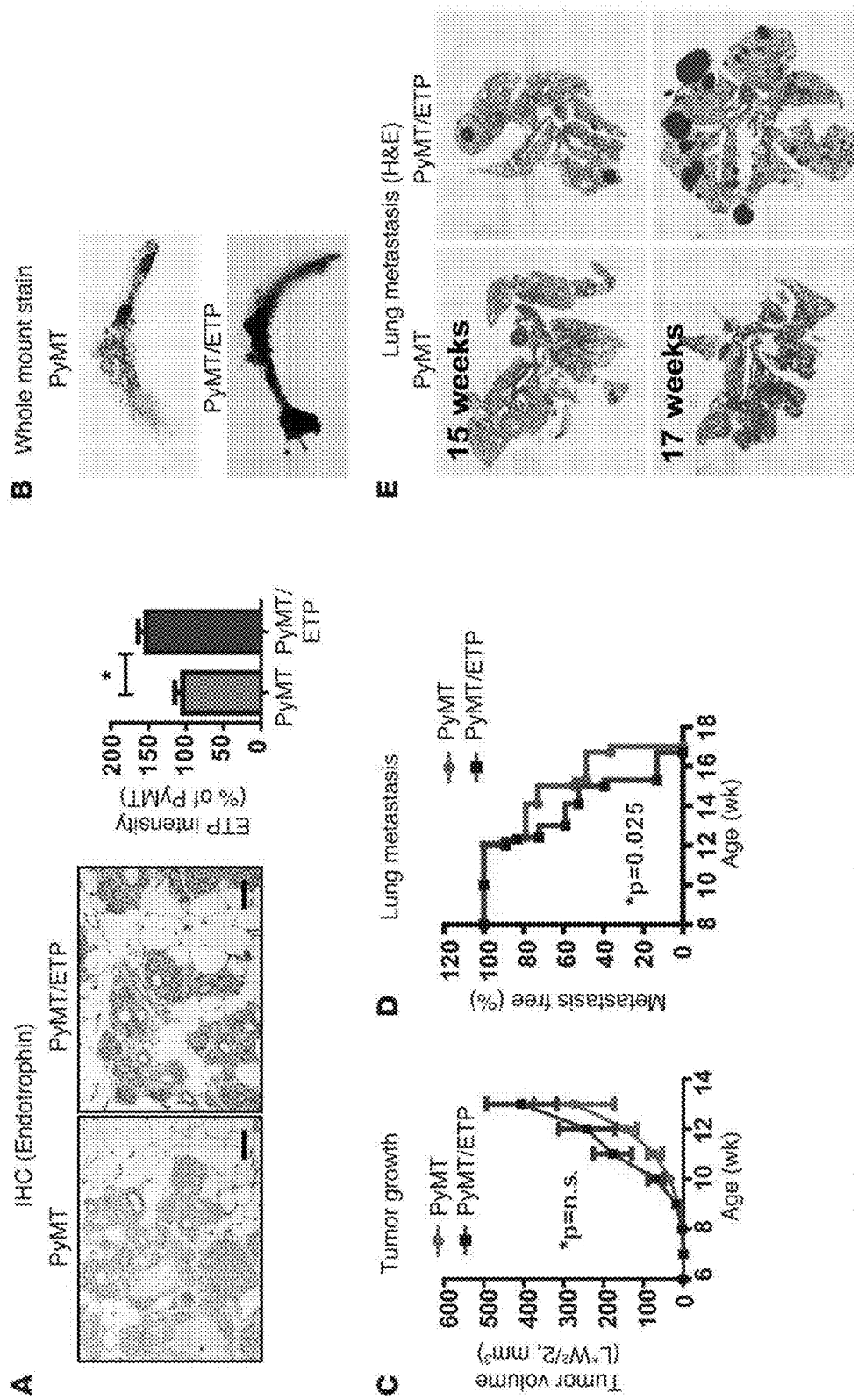
FIGS. 4A-4F: ETP augments primary tumor growth and pulmonary metastasis in the background of PyMT mice.

To assess ETP function, the aim was to expose ETP mice to an additional tumorigenic trigger. For this purpose, the PyMT mouse was used, an aggressive mammary adenocarcinoma model that develops late-stage carcinoma and pulmonary metastasis within 15 weeks. Accumulated ETP levels in tumor tissues of PyMT/ETP mice were about 1.5-fold those of endogenous ETP in PyMT mice (FIG. 4A), and the rate of early tumor growth was augmented in PyMT/ETP versus PyMT mice (FIG. 4B). In light of high endogenous ETP levels accumulating locally as well, differences in late-stage tumors were not significant between the 2 groups when assayed by caliper measurements (FIG.

Figure 4F:
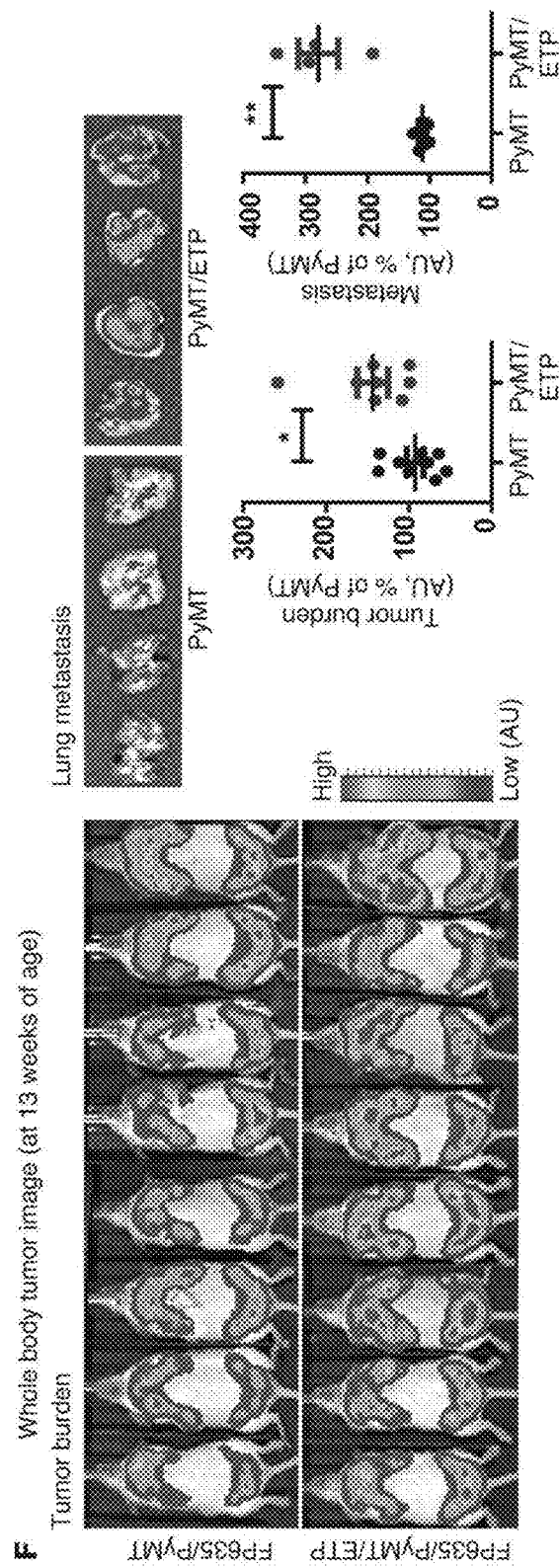
Figures 5A, 5B, 5C, 5D, 5E, 5F, 5G, 5H:
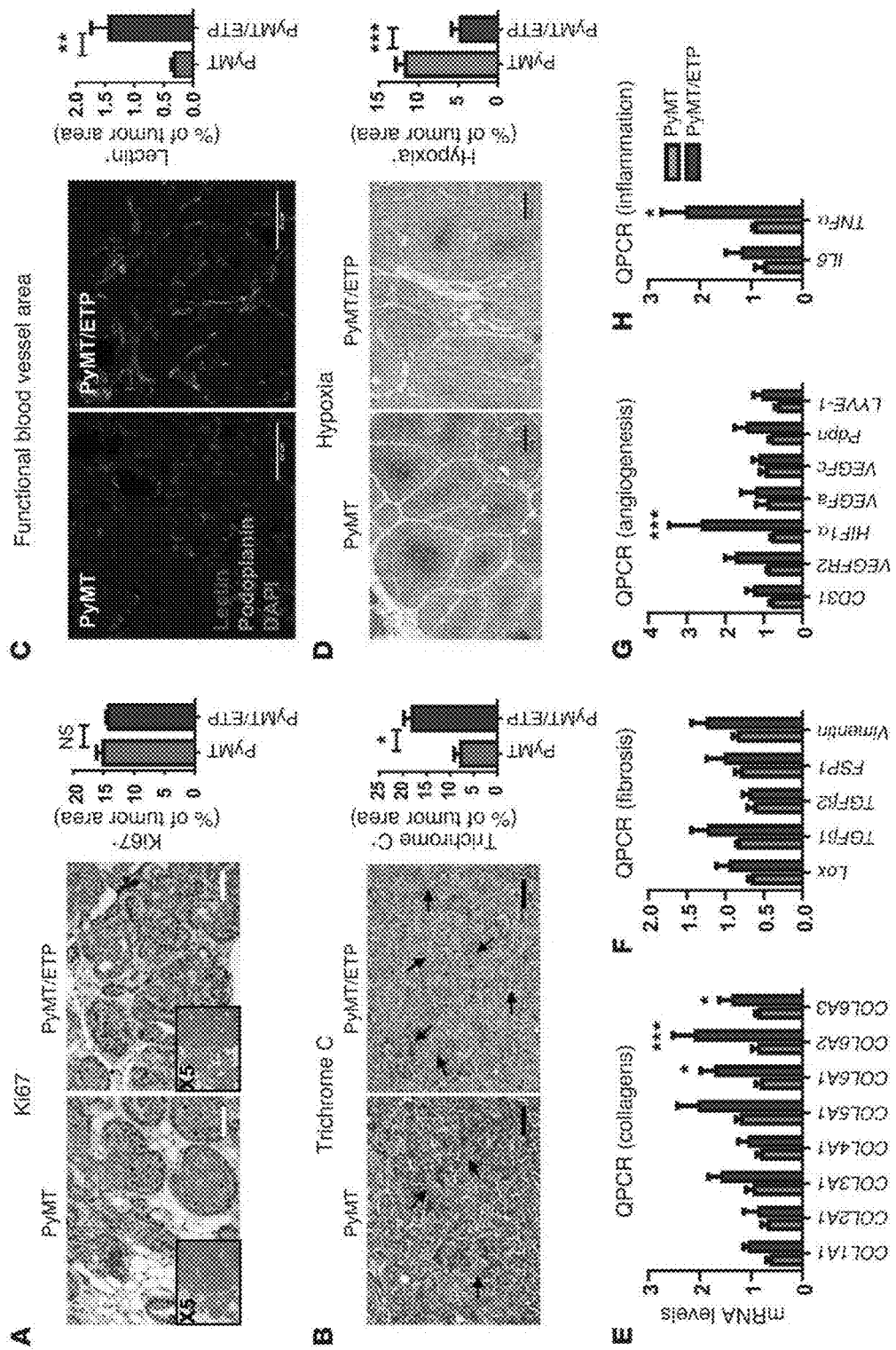
FIGS. 5A-5H: Histological analysis for tumor tissues of PyMT/ETP versus PyMT mice.
Figure 12A:
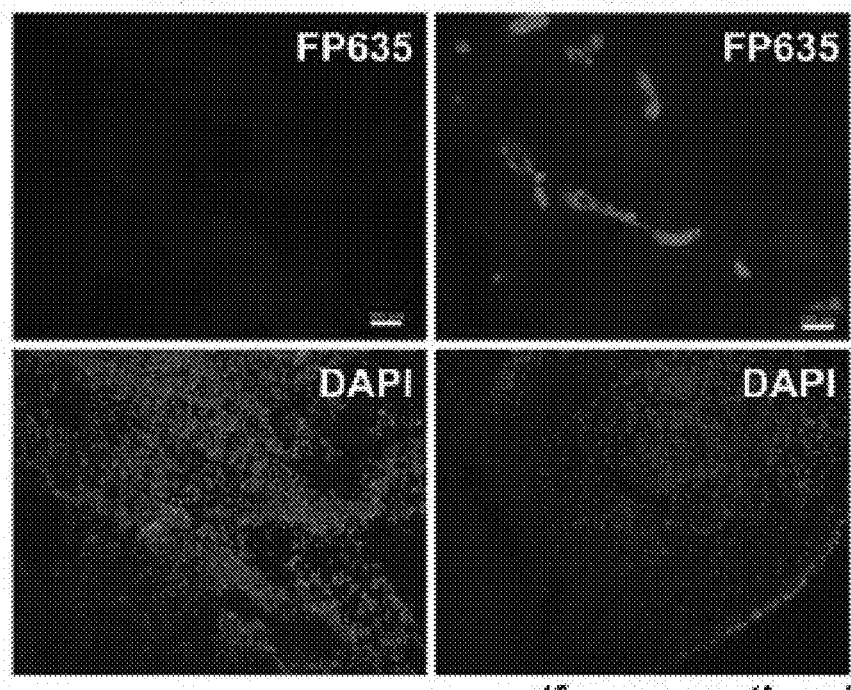
FIGS. 12A-12B. Quantification of tumor progression with the infrared-fluorescence protein (FP635) transgenic mice driven by MMTV promoter.
Figure 12B:
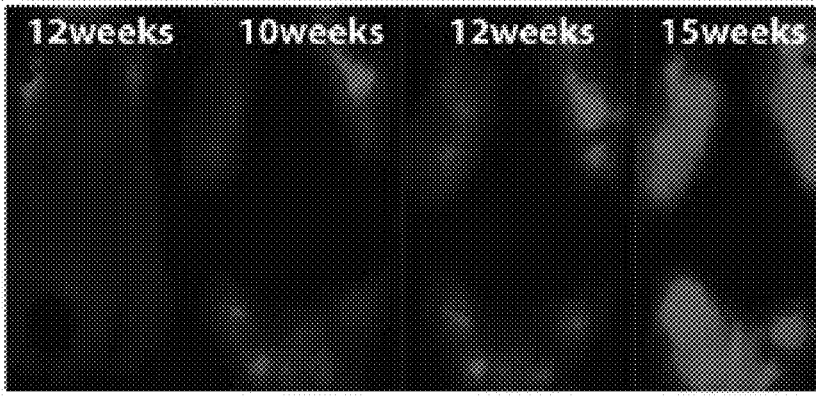

4C). More striking differences were obtained at the level of metastasis (FIGS. 4D and 4E). To more sensitively assess tumor growth, a mouse model was generated harboring the infrared fluorescence transgene FP635 under the control of the MMTV promoter, which allowed monitoring of the tumor growth longitudinally through in vivo imaging (FIG. 12A). Breeding this transgene into PyMT animals (referred to herein as FP635/PyMT mice) allowed readily assessing of the tumor growth by whole-body fluorescence signal intensity, given that the infrared range allows deeper tissue penetration with reduced autofluorescence from surrounding AT (FIG. 12B). By assessing in vivo images, the differences of tumor burden between the FP635/PyMT/ETP and FP635/PyMT groups became apparent and significant (FIG. 4F), which indicates that ETP not only promotes pulmonary metastasis, but also further enhances primary tumor growth. Ki67 staining at late stages did not show an increased frequency of proliferating cells in tumor tissues in PyMT/ETP versus PyMT animals (FIG. 5A). Nevertheless, tumor tissue fibrosis at that age was doubled in PyMT/ETP versus PyMT mice (FIG. 5B). Indeed, a subset of genes associated with tissue fibrosis, including several types of collagens, lysyl oxidase (Lox), and TGFβ, as well as genes for epithelial-mesenchymal transition (EMT), such as fibroblast stimulating protein (FSP1) and vimentin, showed trends toward an increase in tumor tissues (FIGS. 5E and 5F). More dramatic alterations were obtained in the area of tumor angiogenesis: ETP tumor tissues harbored a 3-fold increase in functional blood vessel area compared with controls (FIG. 5C), with a concomitant reduction in hypoxia (FIG. 5D). Markers for angiogenesis, such as CD31, VEGFR2, and HIF1a, were significantly upregulated in tumor tissues from PyMT/ETP mice. Moderate increases were observed in lymphangiogenesis markers, such as VEGFc, podoplanin (Pdpn), and the lymphatic vessel endothelial hyaluronan receptor (LYVE-1) (FIG. 5G). These gene expression changes were consistent with the immunostains of tumor tissues for lymphangiogenesis, such as podoplanin (FIG. 5C). Levels of inflammatory cytokines, such as IL6 and TNFα, were moderately increased (FIG. 5H). Taken together, these findings indicate that ETP enhances fibrosis, angiogenesis, and inflammation, all of which can promote primary tumor growth and metastasis.

ETP Enhances the EMT Process.

Figures 13A, 13B:
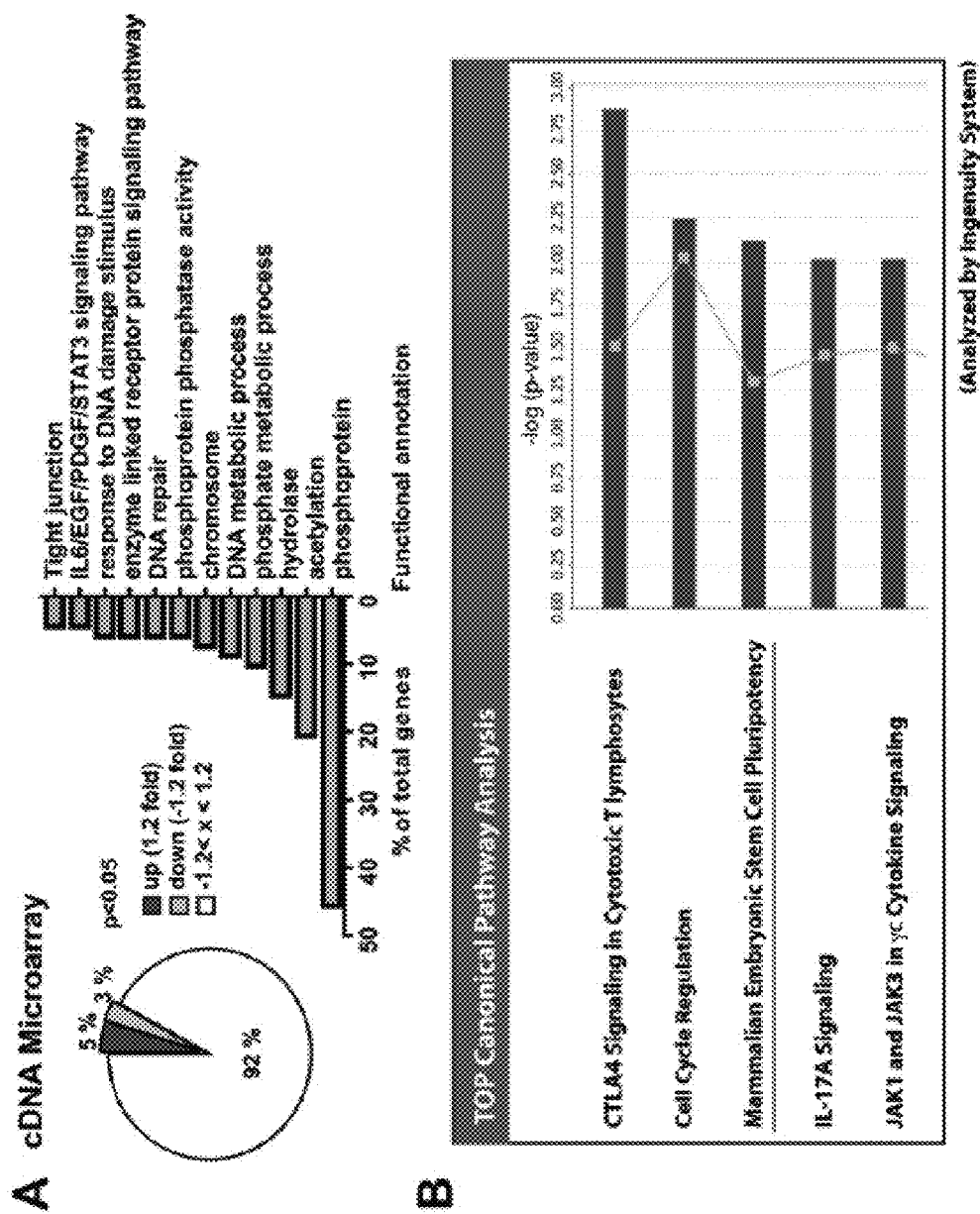
FIGS. 13A-13B. Gene expression profiling for tumor tissues from PyMT/endotrophin compared to PyMT.

To investigate gene expression alterations induced by ETP, cDNA microarrays were compared from size-adjusted tumor tissues from PyMT/ETP and PyMT mice. ETP-modulated genes fell primarily into categories of targets involved in key phosphorylation events, such as phosphatases, kinases, and other phosphoproteins (FIG. 13A). Furthermore, the most significantly altered canonical pathways modulated by ETP were associated with immune responses, cell cycle regulation, and stem cell pluripotency (FIG. 13B). Notably, stem cell-like pluripotency is a hallmark of cancer cells for survival and invasion, which is tightly linked to the process of EMT. Levels of the epithelial cell marker E-cadherin—the loss of which is a characteristic feature of EMT—were significantly decreased in tumor tissues from PyMT/ETP relative to PyMT mice (FIG. 6A), which suggests that ETP induces EMT. This enhanced EMT was consistent with the in vivo phenotype: the metastatic burden was prominently increased in PyMT/ETP versus PyMT mice (FIGS. 4D-4F).

Effects of ETP Synergize with the Canonical TGF-β Pathway to Promote Lung Metastasis.

Figures 14A, 14B:
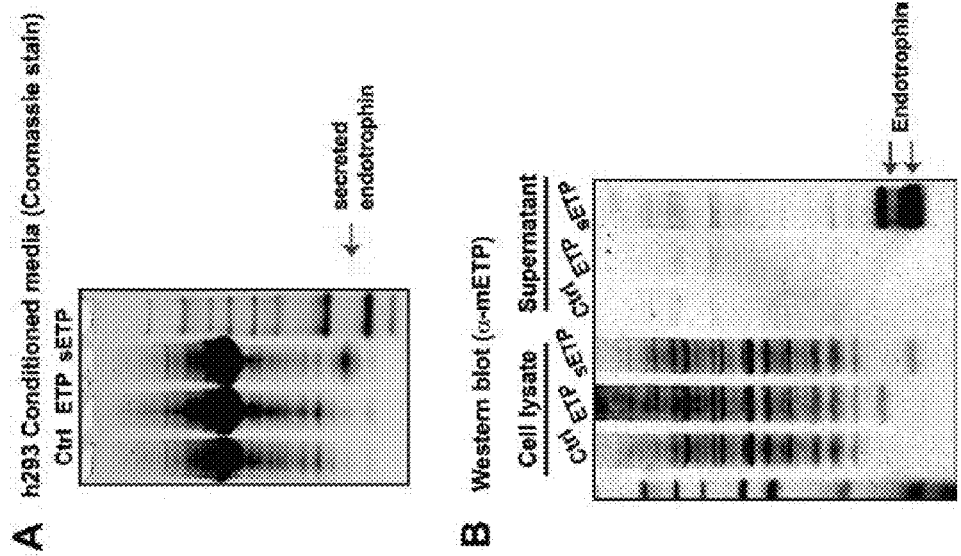
FIGS. 14A-14B. Generation of mammalian cell-produced endotrophin. Mouse endotrophin cDNA in the presence of either a 5' in-frame prolactin signal sequence (sETP) or an adiponectin signal sequence (ETP) was cloned into the mammalian expression vector pRA-GFP. Each construct was transiently transfected into HEK293 cells and supernatants were collected 2 days post transfection.

To delineate the mechanism underlying the increase in EMT processes in PyMT/ETP mice, the effects of ETP on the TGF-β pathway were investigated. TGF-β signaling has previously been implicated in EMT-associated tumor growth and metastasis, which are associated with the acquisition of metastatic traits. To examine whether ETP signaling converges with the canonical TGF-β pathway, 2 ETP constructs were generated: a form that was secretion incompetent, and thus retained within the secretory pathway, as well as a secreted form (FIG. 14A). These constructs were used for a reporter assay with TGF-β-dependent Smad protein-binding elements (SBEs). Interestingly, only the secreted form of ETP enhanced SBE reporter activity; furthermore, this was critically dependent on TGF-β stimulation (FIG. 6B), which indicates that ETP synergizes with the TGF-β pathway through cell-surface interactions. This is based on the fact that the enhanced TGF-β signaling synergistically activated through ETP was completely abolished by treatment with the monoclonal TGF-β neutralizing antibody 1D11 (FIG. 6C), which strongly suggests that ETP-dependent SBE reporter activation and consequent signaling events fully rely on the presence of TGF-β.

Figures 6A, 6B, 6C, 6D, 6E, 6F:
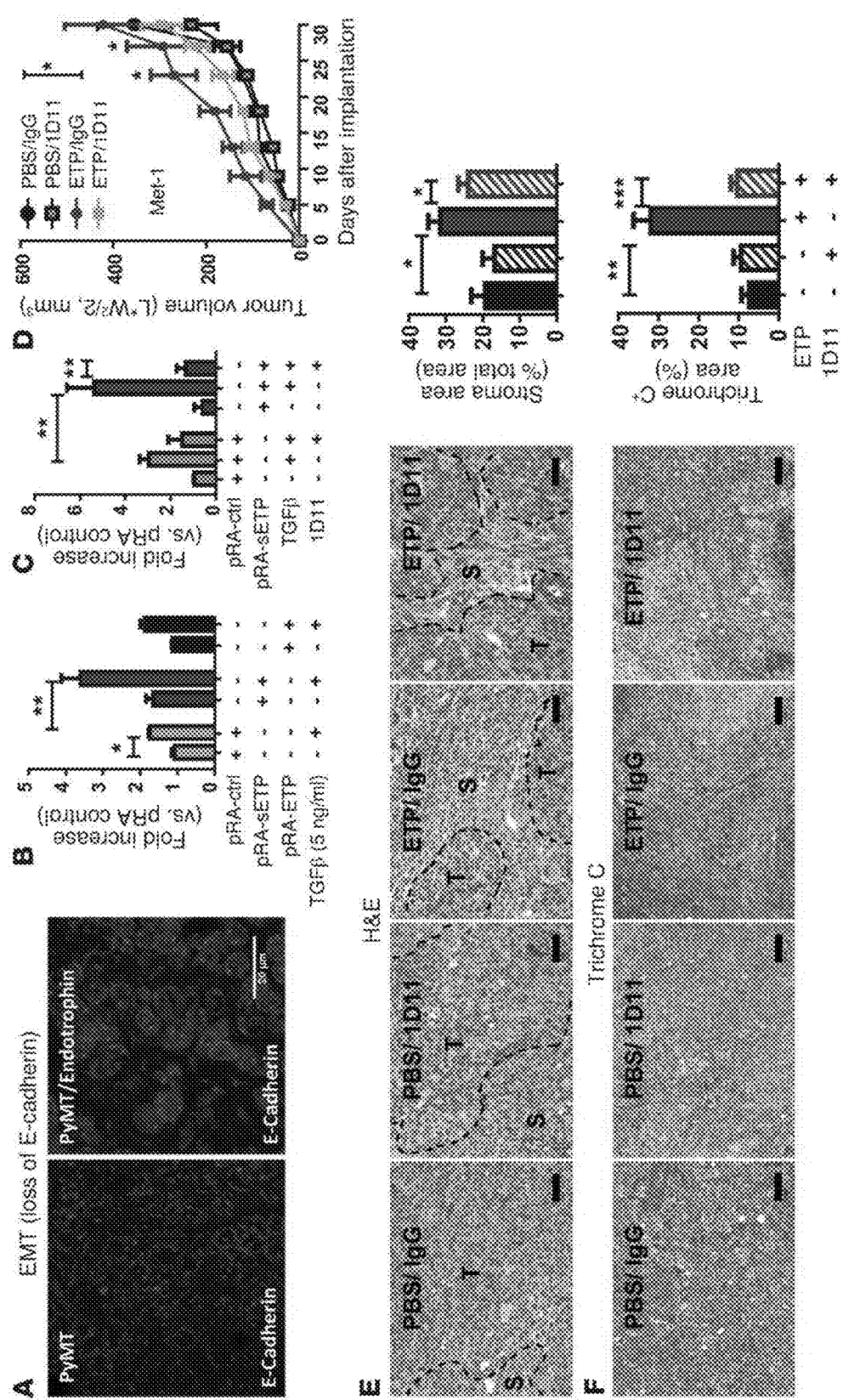
FIGS. 6A-6H: ETP augments metastasis through enforcing TGF-β-dependent EMT.
Figures 6G, 6H:
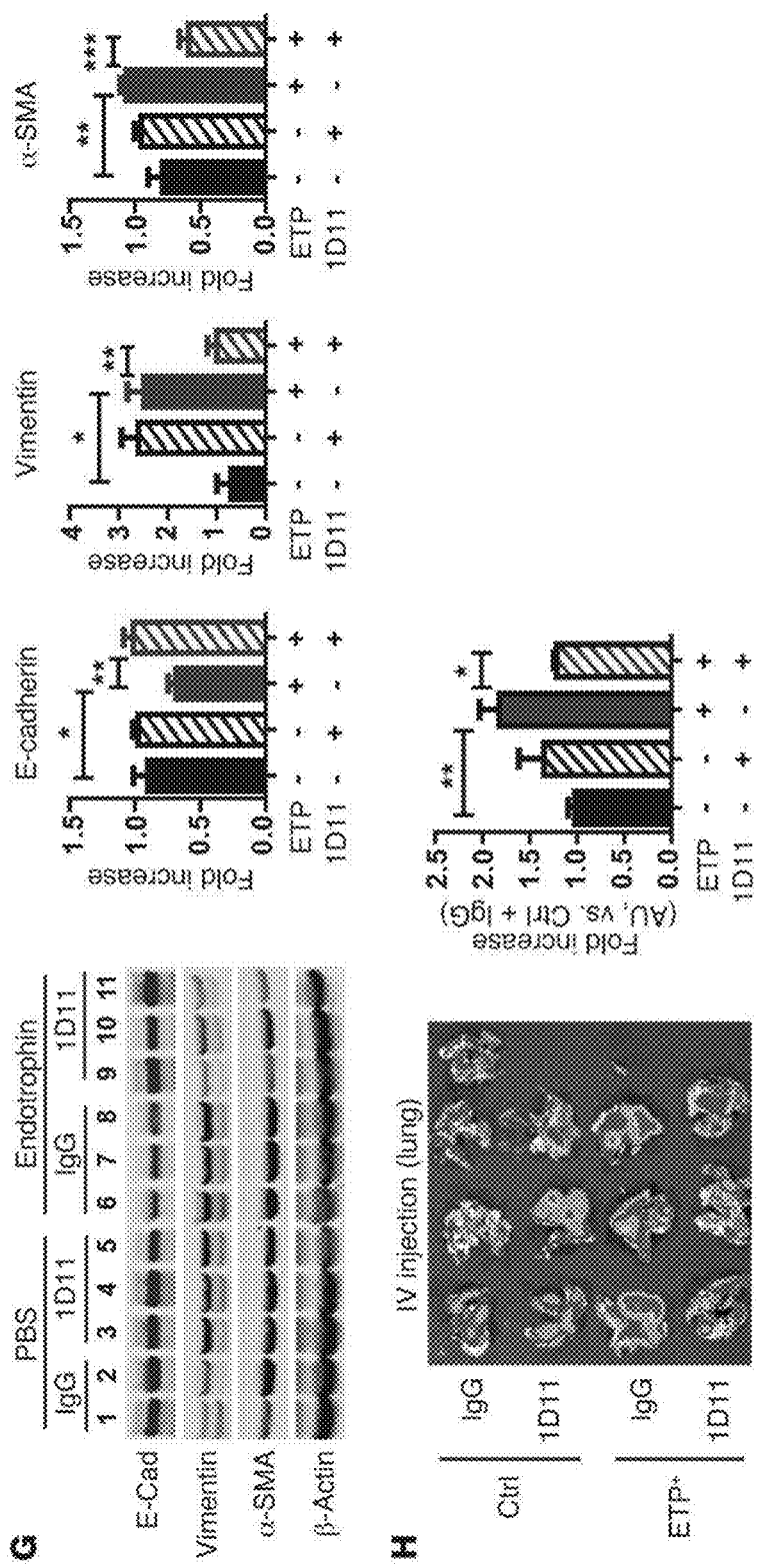

To further elucidate the TGF-β-dependent role of ETP as a tumor enhancer, in a less aggressive experimental setting of tumor progression, an allograft model was used in which TGF-β signaling was inhibited with TGF-β neutralizing antibodies in the context of ETP overexpression. Although tumor growth for Met-1 cells was significantly enhanced by ETP, TGF-β inhibition did not efficiently reduce ETP-induced tumor growth (FIG. 6D), which suggests that TGF-β-mediated signaling is less relevant for the growth of primary tumors in the ETP-expressing tumor stroma. Histological analysis of tumor tissues revealed an increase in mesenchymal-like stromal cells in the ETP-expressing tumor stroma, a phenomenon that was reversed by TGF-β inhibition (FIG. 6E). This further suggests that the TGF-β pathway participates in ETP-induced EMT. Additionally, the ETP-mediated increase in tissue fibrosis was attenuated by TGF-β inhibition (FIG. 6F). These results were subsequently confirmed by examining EMT markers in tumor tissues (FIG. 6G), namely E-cadherin, vimentin, and α-SMA, which is an activated myofibroblast marker widely used for EMT assessment. Of note, manipulation of TGF-β signals in tumor tissues using genetic mouse models for TGF-β, TGF-βR1, and TGF-βRII have highlighted that TGF-β signaling augments cancer cell invasiveness, primarily through stimulation of EMT processes, enhancing metastatic rather than primary tumor growth. The efficacy of TGF-β neutralizing antibodies on the metastatic potential of cancer cells from PyMT/ETP and PyMT mice (referred to herein as ETP$^+$- and Ctrl-cancer cells, respectively) was subsequently investigated. ETP$^+$-cancer cells metastasized at a higher rate than Ctrl-cancer cells (FIG. 6H). Moreover, this increased rate of metastasis was attenuated by TGF-β inhibition (FIG. 6H). Collectively, these results suggest that the TGF-β-dependent aspects of ETP action relate only to the acquisition of cancer cell invasive and metastatic traits, not to primary tumor growth.

ETP, as a Potent Chemokine, Augments Primary Tumor Growth Through Tumor-Stromal Interactions.

Figures 7A, 7B, 7C:
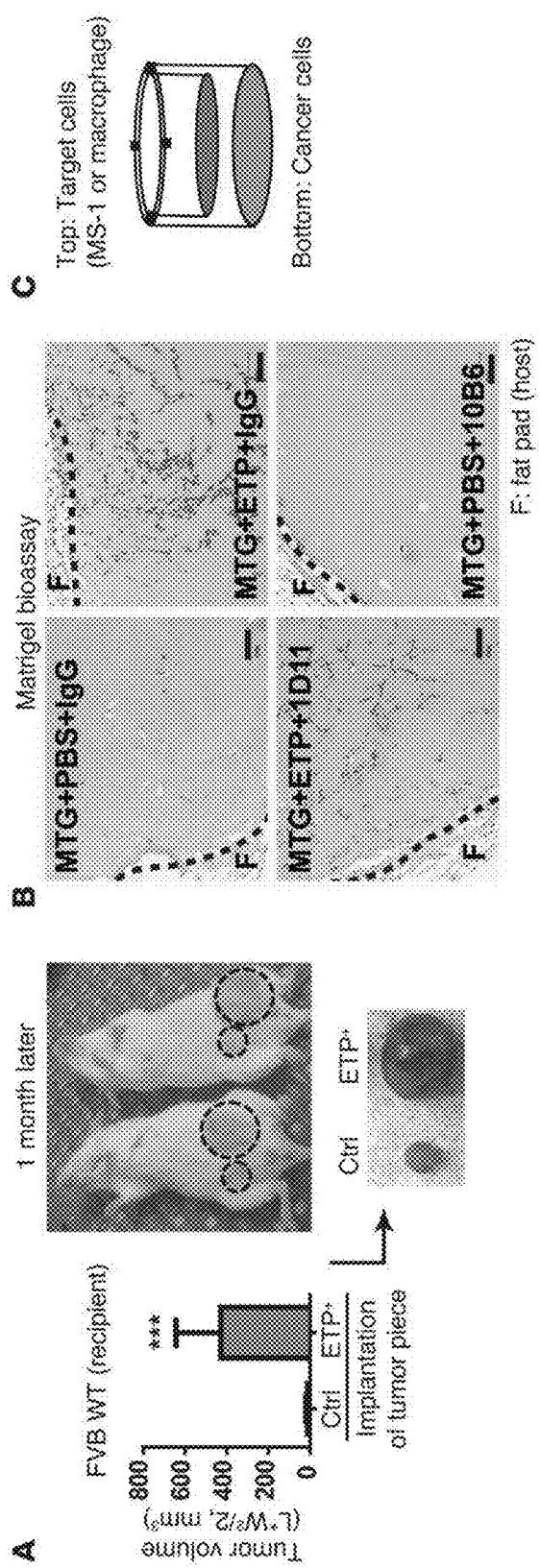
FIGS. 7A-7I: ETP acts as a chemokine augmenting tumor growth.
Figures 15A, 15B, 15C, 15D:
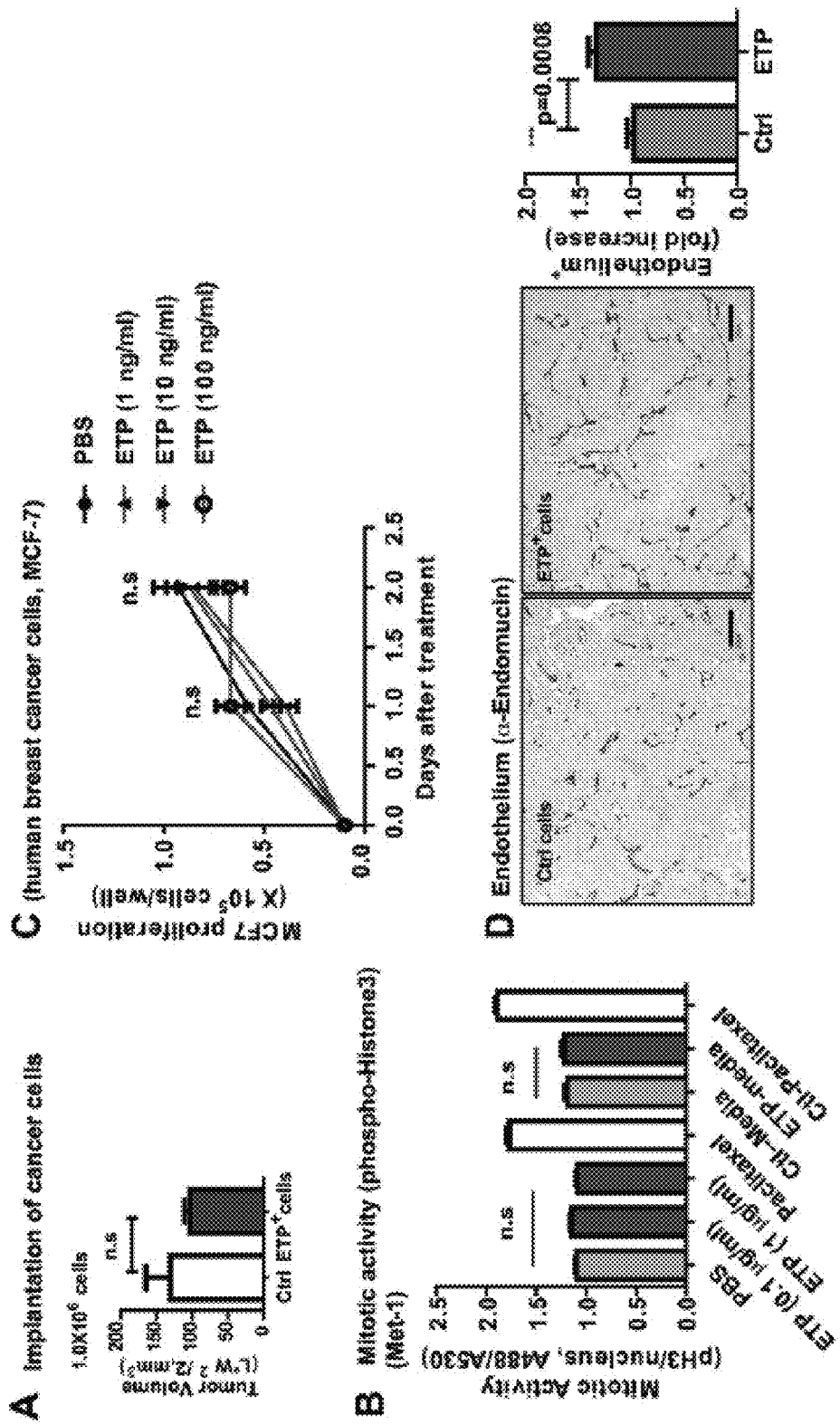
FIGS. 15A-15D. Endotrophin has a limited effect on tumor cell proliferation.
Figures 16A, 16B, 16C:
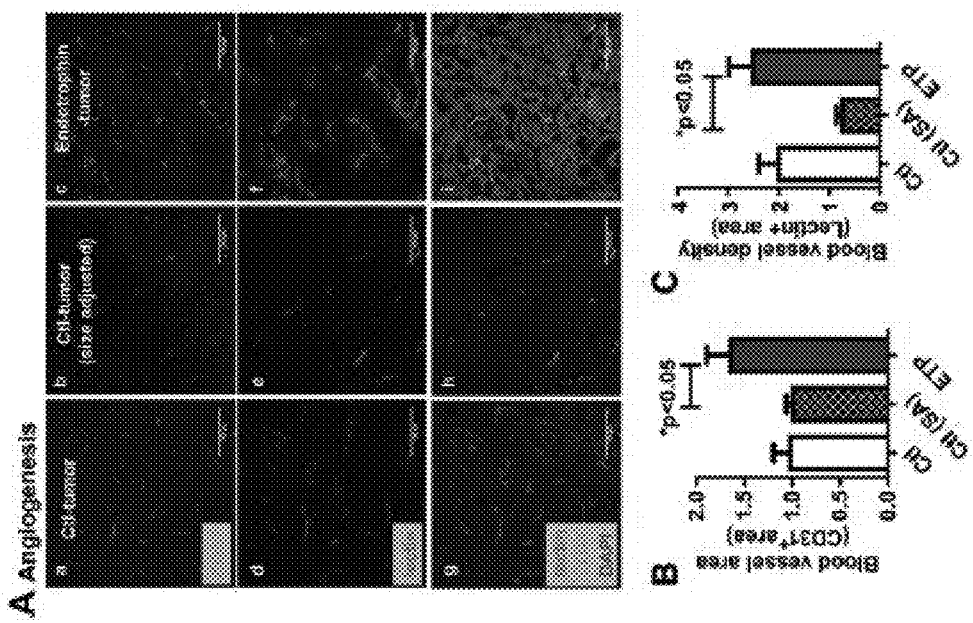
FIGS. 16A-16J. Endotrophin augments tumor angiogenesis, fibrosis and inflammation through mediating tumor-stromal interactions. Small pieces of tumor tissues derived from 12-week-old PyMT (Ctrl-tumor) and PyMT/endotrophin (ETP$^+$-tumor) were implanted into the left or right side of a fat pad of a WT recipient, respectively.
Figures 16D, 16E, 16F, 16G, 16H:
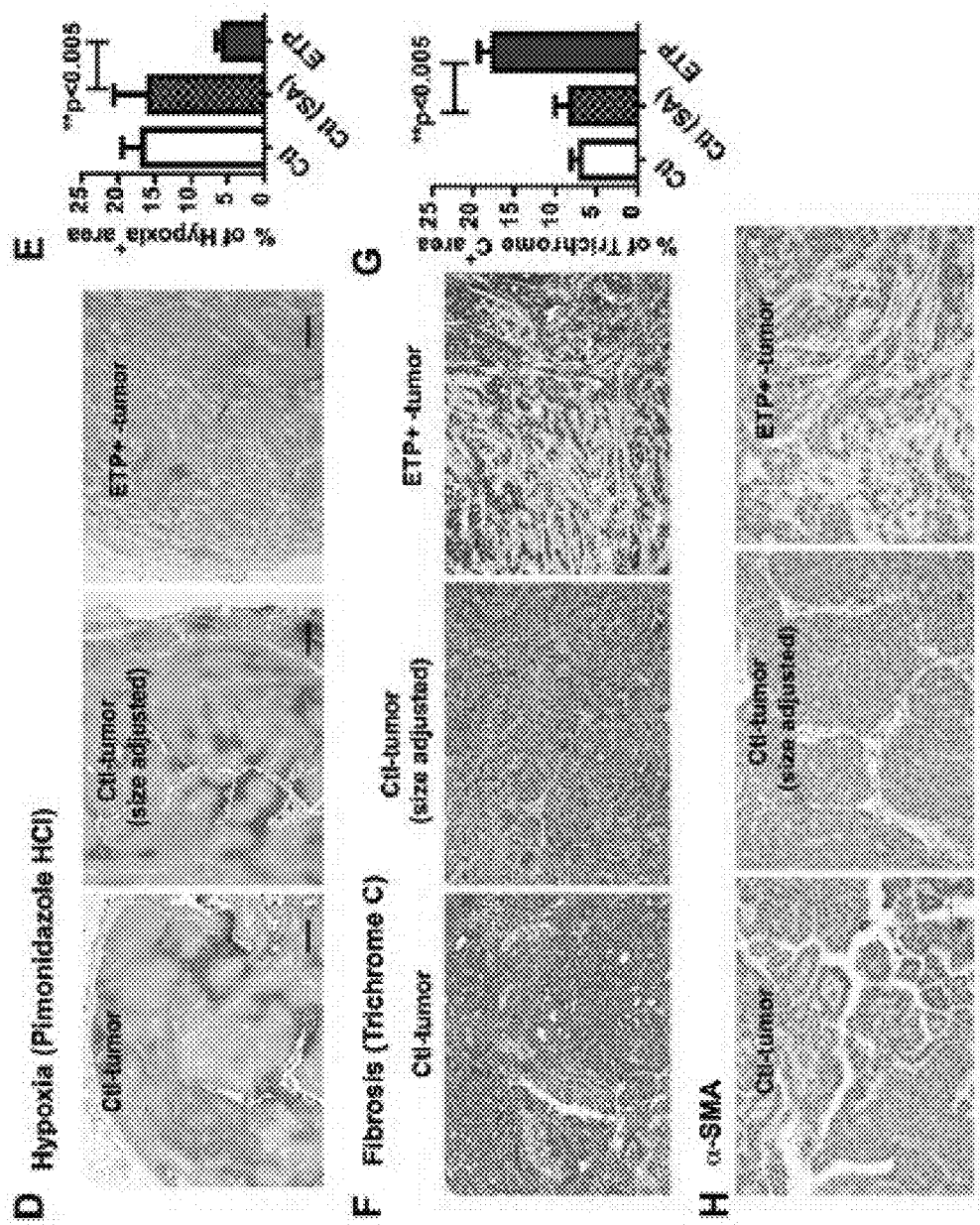
Figures 16I, 16J:
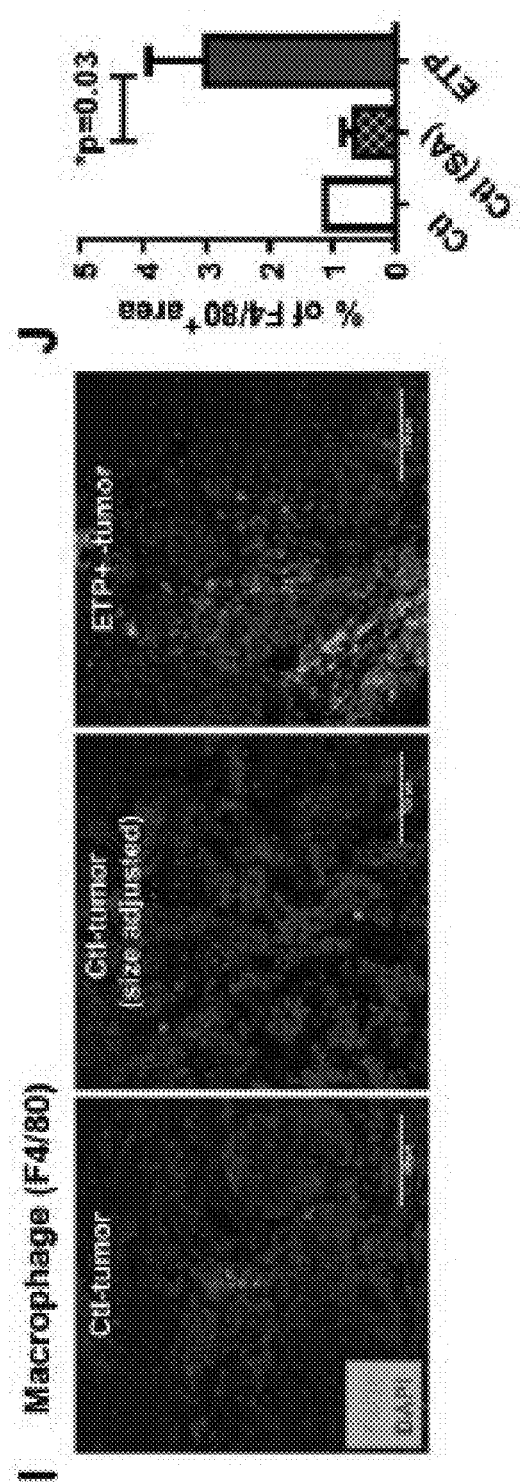

To examine cancer cell-autonomous effects, allografts were performed without Matrigel plugs. Tumor growth of ETP$^+$-cancer cells was comparable to Ctrl-cancer cells (FIG. 15A). Indeed, in vitro examination of mammary cancer cells, including Met-1 and MCF-7 cells, revealed that cell proliferation was not affected by addition of purified ETP (FIGS. 15B and 15C). However, the vascularization of allografts of ETP$^+$-cancer cells was significantly increased (FIG. 15D). This suggests that cancer cells per se are not responsive to ETP with respect to growth, but that ETP augments endothelium formation; therefore, tumor stromal, rather than cancer cell-autonomous, interactions account for the increase in tumor growth observed in vivo. To test this, ETP$^+$- and Ctrl-tumors were implanted into isogenic WT mice. ETP$^+$-tumors grew dramatically faster than did Ctrl-tumors (FIG. 7A). From these allograft studies, the potent proangiogenic, profibrotic, and proinflammatory effects of ETP, initially observed in the PyMT setting (FIG. 5), became evident (FIG. 16). In light of this, stromal effects on primary tumor growth were the focus. These stromal effects were mediated by the tumor-associated vasculature, as well as fibrotic and inflammatory pathways. Major stromal target cell types involved in tumor interactions were endothelial cells, fibroblasts, and macrophages, all of which have established roles in tumor growth and metastasis.

Figures 7D, 7E, 7F, 7G, 7H, 7I:
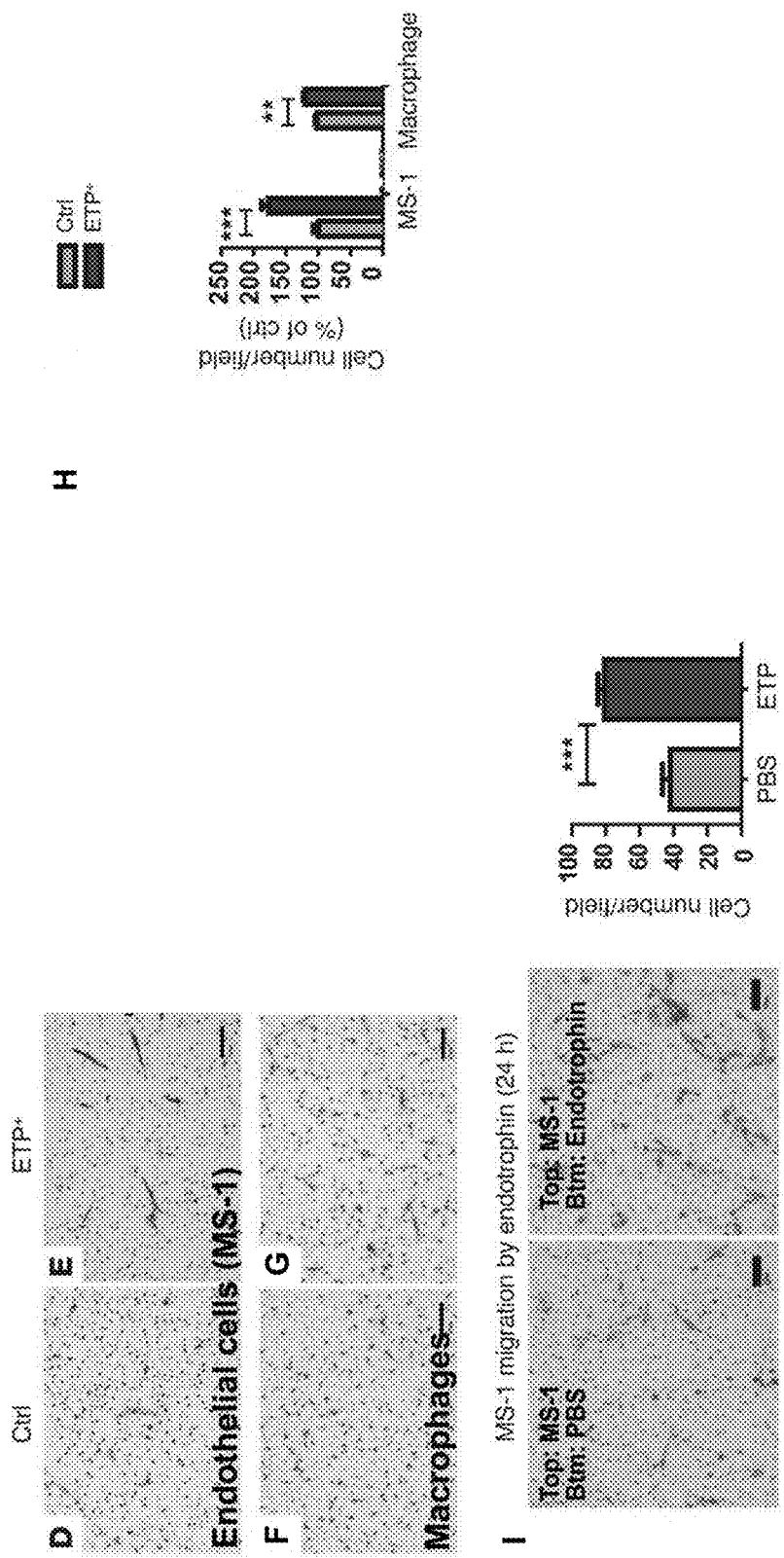
Figure 17A:
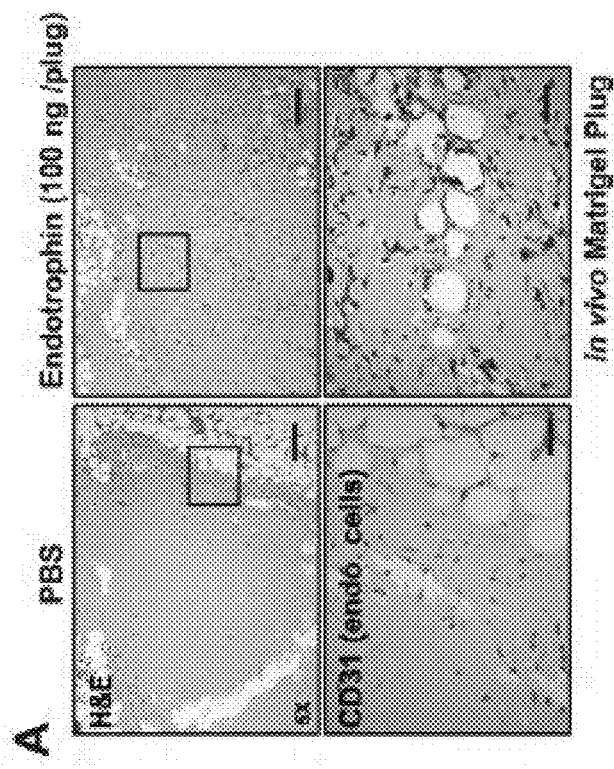
FIGS. 17A-17B. Endotrophin effects on endothelial cell migration.

In light of the findings above, it follows that ETP may function as a chemokine during tumor stroma expansion, recruiting or possibly activating stromal cells to support tumor growth. In vivo targeted cell recruitment studies revealed that Matrigel plugs combined with recombinant ETP and injected into mammary fat pads of WT mice recruited significantly more stromal cells than did PBS (FIG. 7B). Monoclonal anti-ETP antibodies were subsequently generated to effectively neutralize ETP, thereby generating an ETP-based therapeutic approach (FIG. 9C). Chemokine activity of ETP was completely blocked by 10B6, but not by 1D11 (FIG. 7B), which suggests that ETP-inherent chemokine activity was independent of TGF-β signaling. Furthermore, the majority of cells recruited into the Matrigel plugs by ETP were CD31$^+$ endothelial cells (FIG. 17A). More specifically, mammary epithelial cancer cells were cocultured with either mouse endothelial cells (MS-1; FIGS. 7D-7E) or primary macrophages (FIGS. 7F-7G) in a Transwell plate (FIG. 7C), and the migration of the MS-1 cells and macrophages were subsequently quantified (FIG. 7H). ETP$^+$-cancer cells recruited substantially more endothelial cells and macrophages (FIGS. 7E, 7G, and 7H). This suggests that the majority of chemoattractant properties exerted by COL6 are exerted by ETP.

Figure 17B:
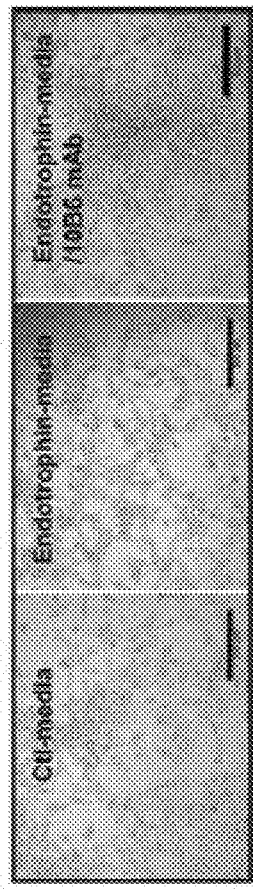

In vitro cell migration assays revealed that ETP recruited twice as many MS-1 cells than did controls (FIG. 7I). Furthermore, in vitro angiogenesis assays using MS-1 cells demonstrated that endothelial cells incubated with conditioned media from ETP-overexpressing HEK-293T cells mobilized and organized vasculature structures much more actively than conditioned medium harvested from control HEK-293T cells (FIG. 17B). 10B6 completely blocked these effects (FIG. 17B). Thus, ETP plays a crucial role in endothelial cell recruitment, migration, and vessel formation during the process of angiogenesis. Based on these observations, it is concluded that ETP is critical for the recruitment of stromal cells into the tumor microenvironment through its action as a chemokine.

A Neutralizing Anti-ETP Monoclonal Antibody Attenuates Tumor Growth by Inhibiting ETP-Mediated Expansion of the Tumor Stroma.

Figures 8A, 8B, 8C:
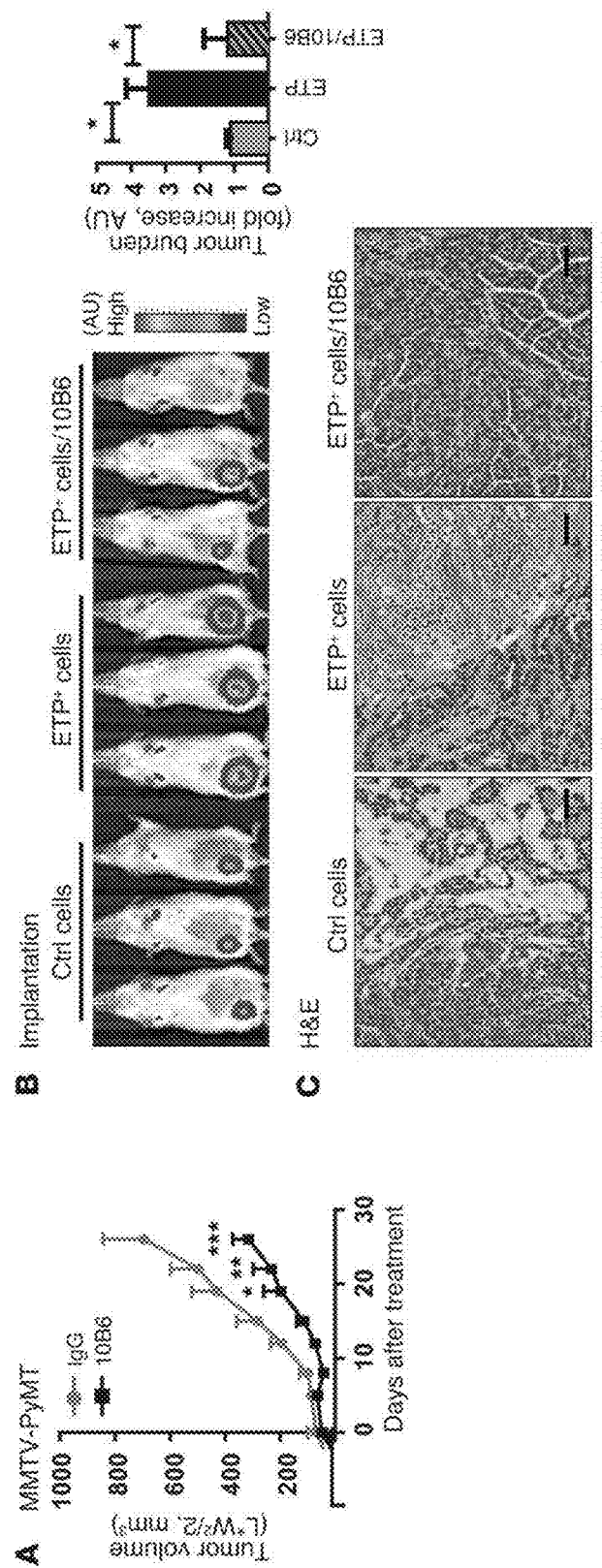
FIGS. 8A-8I: 10B6 blocks ETP-mediated stromal expansion in vivo.
Figures 8D, 8E, 8F, 8G, 8H, 8I:
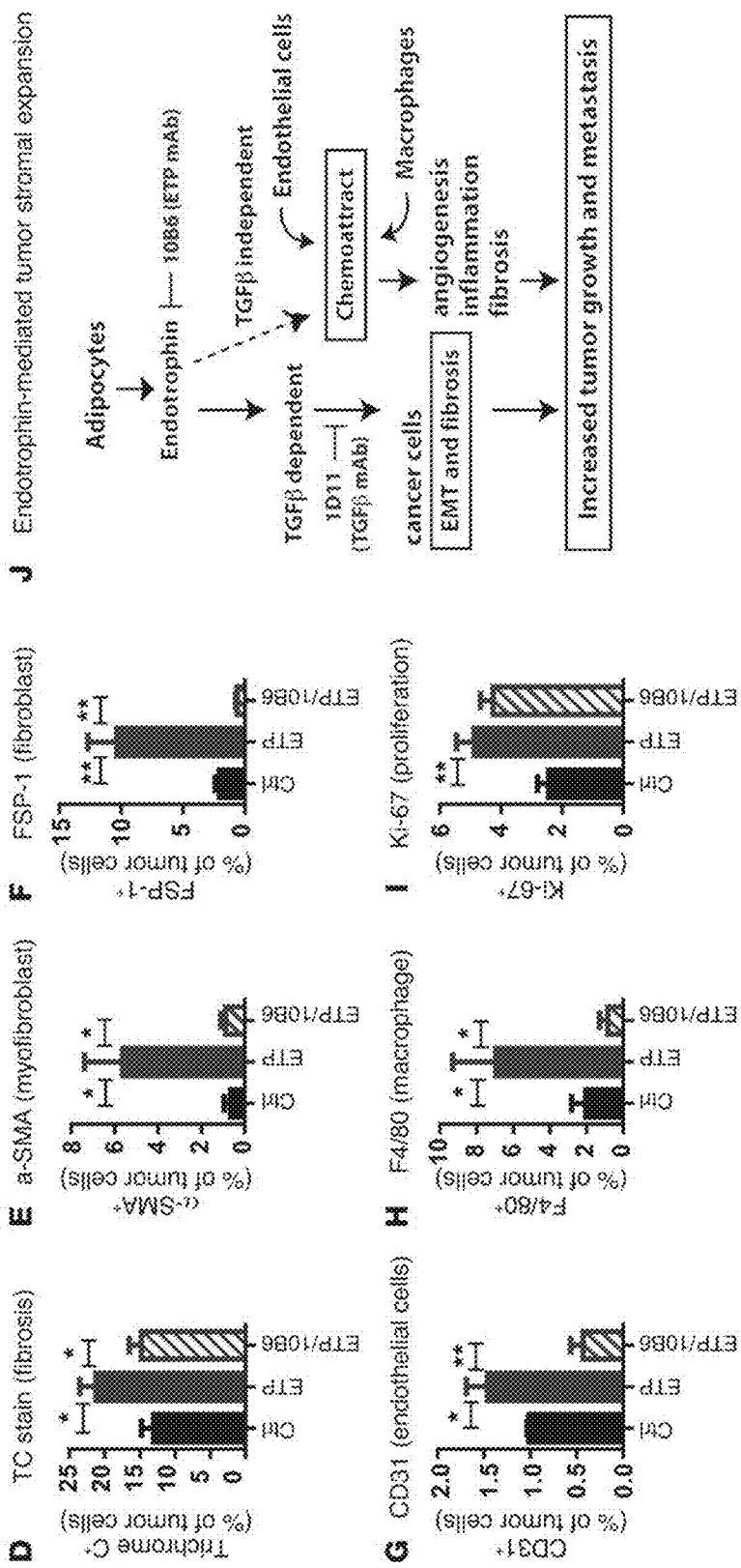

It was next examined whether ETP neutralization can attenuate tumor progression. Of note, PyMT mice expressed high levels of endogenous ETP in the tumor-infiltrated stromal compartment (FIG. 1E). Tumor growth was significantly attenuated by 10B6 treatment compared with isotype control IgG treatment (FIG. 8A). Similarly, FP635/ETP$^+$-cancer cells were implanted into WT mice, with or without 10B6 added to the Matrigel plug; tumor growth was then monitored using fluorescence imaging. The rate of ETP$^+$-cancer cell growth was significantly higher relative to Ctrl-cancer cells; however, their growth was effectively attenuated by 10B6 (FIG. 8B). Histological analysis of tumor tissues indicated that various stromal cells had the capacity to infiltrate into the Matrigel plugs containing ETP$^+$-cancer cells. Again, 10B6 inhibited ETP-mediated tumor stromal expansion and eventually triggered tumor regression (FIG. 8C). ETP$^+$-cancer cell allografts consistently displayed higher levels of fibrosis (FIG. 8D) and a high degree of stromal cell infiltration, including by α-SMA$^+$ cells, FSP-1$^+$ fibroblasts, and CD31$^+$ endothelial cells in addition to F4/80$^+$ macrophages (FIGS. 8E-8H). These cells were highly proliferative, as demonstrated by Ki67$^+$ staining (FIG. 8I). As expected, the ETP-mediated increase in fibrosis and stromal expansion was completely blocked by 10B6 (FIG. 8D-8H). Collectively, the results indicated that stromal adipocytes play a crucial role in mammary tumor progression; that ETP is a powerful stromal factor that exerts a major influence on primary tumors through its chemokine activities; and that ETP can affect metastatic growth via TGF-β-mediated EMT. Thus, ETP-directed approaches may serve as novel therapeutic regimens in the treatment of breast cancer (FIG. 8J).

DISCUSSION

Figure 18:
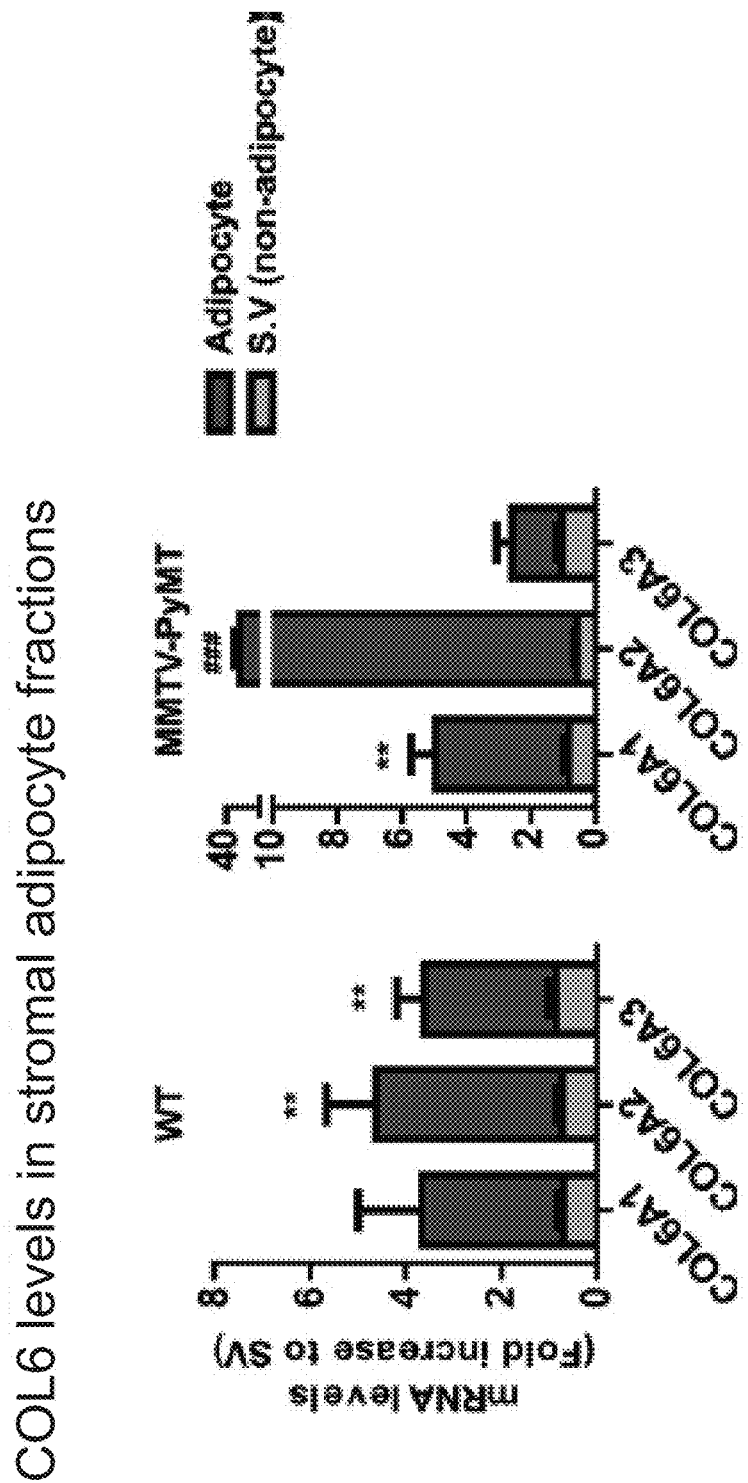
FIG. 18. Contributions of stromal adipocytes to COL6 mRNA expressions. COL6A1-, A2 and -A3 mRNA levels in adipocytes (Adi) and stromal-vascular (S.V.) fractions in mammary glands for WT and PyMT mice. mRNA levels were determined by RT-qPCR. Results were normalized to β-actin and represented as mean±SEM. Bar graph is represented as -fold increase over the S.V fraction. **p<0.01, ###p<0.001 vs. S.V by unpaired student t-test. (n=4/group, tissues from 3 mice were pooled in one sample; i.e., total 12 mice/group).

A prominent environmental stimulus of tumor dissemination is hypoxia, triggered by a high demand for cell proliferation and insufficient angiogenesis. Comparable to this process, hypertrophic AT expansion during obesity can also trigger local hypoxia that can further progress to AT fibrosis. These obesity-related pathophysiological changes can lead to an environment that is conducive to cancer growth, such as chronic inflammation, inadequate angiogenesis, and enhanced fibrosis. In this setting, obesity may contribute to an ETP-rich tumor microenvironment through a positive feed-forward mechanism. Indeed, COL6α3 message levels are upregulated in obese AT. COL6 upregulation has been reported in various aspects of tumor progression. Malignant cancer cells can also express COL6; this has been reported for the mammary gland, the colon, pancreatic ductal adenocarcinomas, and hepatocarcinomas. Thus, the source of ETP in the tumor microenvironment may be heterogeneous, with signals cooperatively influencing cancer cell behavior through paracrine and autocrine pathways. Nevertheless, stromal adipocytes represent a prominent source for COL6 in the mammary tumor microenvironment (FIG. 18A). However, the detailed mechanisms underlying the specific effects of COL6 on tumor behavior have not previously been elucidated. Here, the above results show that ETP, a cleaved product of COL6, can be a critical mediator of several tumor-associated phenomena and is of particular importance in tumor progression in the context of obesity.

Within the tumor milieu, EMT is initiated by extracellular stimuli. This can be exerted by ECM components (collagens, fibronectin, hyaluronic acids, and MMPs) as well as by certain growth factors (TGF-β, EGF, and HGF), all of which are provided by both paracrine and autocrine signals within the tumor microenvironment. One of the prominent ECM molecules released from stromal adipocytes is COL6. As a COL6 processing product, ETP plays an important role in the local microenvironment, stimulating TGF-β-dependent EMT in the context of mammary tumors to potentiate prometastatic effects (FIG. 6). Gene expression profiling and immunostaining of tumor tissues from PyMT/ETP mice confirmed enhanced ETP-mediated acquisition of EMT characteristics, whereas in vitro data indicated that ETP alone did not induce EMT (data not shown). This suggests that ETP may function as an important costimulator of existing pathways for the EMT, such as TGF-β signaling and possibly activation of integrins and Wnt signals.

Increased tissue fibrosis, combined with high tissue rigidity (due to ECM remodeling and crosslinking), is positively associated with tumor growth. The results above revealed an ETP-induced fibrotic environment, with high levels of myofibroblast accumulation within tumor tissues, as a key characteristic of ETP action. These activated myofibroblasts in ETP$^+$-tumors were derived, at least in part, by EMT. In addition, ETP may facilitate additional processes, such as microfibril assembly of preexisting collagen fibers or stimulation of myofibroblast differentiation. Moreover, promoting transformed mesenchymal cell proliferation can enhance the appearance of additional stromal cells; ETP may also effectively promote this process. Indeed, blocking the EMT by using a TGF-β neutralizing antibody did not completely eliminate fibrosis in ETP$^+$-tumors (FIG. 6F). These data indicate that the ETP-induced EMT and subsequent fibrotic traits in tumors contribute to an increase in tumor growth and metastasis, which highlights a central role for ETP in tumor progression.

Evidence was also provided herein for the potent ETP-mediated chemoattractant properties. These ETP effects can even be mimicked in a tumor-free environment. A number of reports highlight significant correlations between COL6α3 and chronic inflammation, based on increased macrophage infiltration into AT depots of obese subjects. The ETP-mediated chemoattractant properties described herein may offer a mechanistic basis for these clinical correlations. Neutralizing these ETP-mediated effects in normal, tumor-free AT may yield beneficial outcomes as well. The current efforts are directed toward adipocyte-derived overexpression of ETP, to examiner whether a local excess of ETP will exert beneficial effects (due to its proangiogenic properties) or negative effects (due to its proinflammatory and profibrotic properties) on a fat pad not challenged with an invading tumor.

Fibrosis in obese AT is associated with an increase of various MMPs or TIMPs resulting in collagen degradation. MMP-11, MMP-2, and MMP-9 have been suggested as peptidase for COLE, although there is no further evidence whether these MMPs cleave ETP. Based on the fact that most cancer cells express high levels of MMPs associated with tumor growth and metastasis, it is likely that there are abundant sources for ETP cleavage activity within the tumor microenvironment. The identification of the critical protease involved in ETP processing may offer a new approach to curbing growth by pharmacologically inhibiting this step. The findings herein unveiled an important role of the adipocyte as an active component of the tumor stroma that actively interacts with cancer cells and a number of other relevant local cell types. The data herein also highlights that an adipocyte-derived ECM cleavage product actively contributed toward the remodeling of the tumor microenvironment by enabling the progression of tumor growth and metastasis through enhancement of the EMT process and subsequent chemotaxis of endothelial cells and macrophages. In many aspects, the deposition of ECM components, such as ETP in the tumor stroma, resembles a wound-healing process, as this involves the recruitment and stimulation of immune cells, endothelial cells, and fibroblasts during the wound repair process. However, unlike during the wound-healing process, ETP prompts cancer cells to sustain mesenchymal cell-like traits and activates fibroblasts in the tumor stroma, drastically increasing local fibrosis and eventually enhancing metastatic growth. The findings herein have further implications for several tissues that have an associated pathological fibrotic component, such as the liver, cartilage, lung, and heart; COLE expression has been documented in all these tissues. Further efforts targeted toward ETP neutralization in various pathological settings can establish this approach is a viable antifibrotic strategy that is generally beneficial, not only in the setting of tumor progression and metastasis, but also during normal AT expansion.

Methods

Mice.

See Supplemental Methods for detailed information on the mice used herein. All experiments were conducted using littermate-controlled female mice. All animals used in this study were in a pure FVB background.

Tumor Imaging.

FP635/PyMT mice or cancer cells isolated from tumors from FP635/PyMT mice were imaged with an IVIS scanner (Caliper Lifesciences), and the signal intensity was analyzed with Living Image version 3.2 (Caliper Lifesciences). See Supplemental Methods for conventional analyses of tumor growth and metastasis.

ETP-Specific Polyclonal and Monoclonal Antibodies.

ETP-GST fusion proteins for both mouse and human ETPs were purified from bacteria and used as antigens for polyclonal antibodies (Covance). For monoclonal antibody generation, native ETP was purified by gel filtration chromatography (GE Healthcare) from conditioned media of a mouse ETP-overexpressing HEK-293 stable cell line. See FIG. 1A for ETP amino acid sequences.

Quantitative RT-PCR.

Total RNA was isolated using the RNeasy kit (Qiagen) following tissue homogenization in TRIzol (Invitrogen). Total RNA (1 μg) was reverse transcribed with SuperScript III reverse transcriptase (Invitrogen). Quantitative real-time PCR (qRT-PCR) was performed using Roche Lightcycler 480. Primer sequences used in this study have been described previously.

Analysis of ETP Homing.

The homing of ETP in circulation was determined by injecting fluorescently labeled ETP into tail veins. ETP and IgGs were labeled with IRDye800 CW NHS Ester (Licor Bioscience) at a 1:1 molar ratio (dye/protein), according to the manufacturer's instructions. Whole-body fluorescence images were collected on the Odyssey scanner (Licor Bioscience). All scans were performed under anesthesia (Aerrane) using an EZ-2000 Microflex small-animal anesthesia system (EZ Systems). At the end of experiments, each organ was collected and imaged for signal intensity with the Odyssey scanner. Quantified values were normalized to the total area of each organ.

Histological Analysis.

Formalin-fixed paraffin-embedded tissue sections were used for immunohistochemistry. Deparaffinized tissue slides were stained with the primary antibodies shown in Supplemental Methods. Staining for functional blood vessels and hypoxic lesions as well as whole-mount staining of mammary glands were followed as described previously. TUNEL assays were performed according to the manufacturer's protocol (Trevigen Inc.). Masson's Trichrome C and H&E staining were performed by J. Shelton (University of Texas Southwestern Medical Center, Dallas, Tex., USA). Deidentified human tumor samples were obtained from the University of Texas Southwestern Tissue Resource.

Primary Culture of Mammary Cancer Cells and Implantation.

Isolation of mammary epithelial cancer cells and implantation procedures were as previously described. Tumor growth was monitored once weekly beginning 2 weeks after implantation.

In Vitro Cell Migration Assay.

Thioglycollate-elicited macrophages or MS-1 in serum-free media were loaded into the upper chamber of a Transwell plate (8 μm pore size; Costar). As chemoattractants, ETP or the indicated cancer cells were added to the bottom chamber with DMEM containing 2% FBS. 18 hours later, cells on the underside of the membrane were fixed with 10% formalin, stained with hematoxylin, and counted. Images were acquired using the Nikon Cool Scope (Nikon).

Statistics.

Data are presented as mean±SEM. Data were analyzed by 2-way ANOVA followed by Newman-Keuls multiple comparison test or by 2-tailed Student's t test, as appropriate, with GraphPad Prism version 5 software. A P value less than 0.05 was considered statistically significant.

Study Approval.

This study was carried out in strict accordance with the recommendations of the NIH *Guide for the Care and Use of Laboratory Animals*. All animal experiments were approved by the Institutional Animal Care and Research Advisory Committee at the University of Texas Southwestern Medical Center (protocol no. 2010-0006). All efforts were made to minimize animal suffering.

Supplemental Methods

Mice.

—Endotrophin transgenic mice were generated by fusing cDNA encoding the mouse COL6A3-05 domain (amino acids 2590-2657, NP 034056) to the prolactin signal sequence at the amino-terminus (ATGGACAGCAAAGGT-TCGTCGCAGAAAGGGTCCCGCCTGCTCCTGCT-GCTGGTGGTGTCAAATCTACT CTTGTGCCAGGGT-GTGGTCTCC; SEQ ID NO: 14), which allows endotrophin to be secreted from the cells, into a plasmid containing the 3.2-kb MMTV (mouse mammary tumor virus) promoter and 3'-SV40 region. Transgene-positive offspring were genotyped using PCR with the following primer set: 5'-ACGA-GAACAGATTCCACTCC-3' (SEQ ID NO: 15) and 5'-TCAGCAGTAGCCTCATCATCAC-3' (SEQ ID NO: 16). Infrared fluorescent protein FP635 transgenic mice were generated by subcloning the FP635 domain originated from plasmid pTurboFP635 (Evrogen) into a plasmid containing the 3.2-Kb MMTV promoter and a conventional 3'-UTR region. Genotyping was performed using PCR with following primer set: 5'-AGAGACCTACGTCGAGCAGC-3' (SEQ ID NO: 17) and 5'-GGGTCCATGGTGATACAAGG-3' Reagents. Primary antibodies used in histological analysis: rabbit polyclonal against holo-COL6 (Abcam, Ab6588), CD31 (Abcam, ab38364), α-smooth muscle actin (Abcam, ab5694), FSP1 (Abcam, ab27957), Vimentin (Cell Signaling, #5741) and E-cadherin (Cell Signaling, #3195); mouse monoclonal F4/80 (invitrogen, MF48000) and cytokeratin (Cell Signaling, #4545); rat monoclonal Ki67 (Dako Cytomation) and endomucin (Santa Cruz, sc-65495). TGFβ neutralizing antibody, 1D11 was generously providing by Dr. Rolf Brekken (UTSW Medical Center, Dallas).

Analysis of Tumor Progression and Lung Metastasis.

Tumor onset was monitored twice weekly by palpation. Tumor sizes were measured with a digital caliper twice weekly and the volumes were calculated as (length×width)/2. Inguinal tumors were weighted to determine tumor burden. Animals were sacrificed when the tumor burden visibly affected the host or when the tumors reached the IACUC predetermined limit of 20 mm along one axis. Metastatic tumor growth was determined by histological analysis with H&E stained lung tissues.

Immunoblotting.

Cell lysates were harvested using NP-40 lysis buffer, supplemented with phenylmethylsulfonyl fluoride (PMSF, 1 mM), protease inhibitor (Roche) and phosphatase inhibitor (Roche). Protein samples were immunoblotted using standard methods. For the culture media, differentiated 3T3-L1 adipocytes and preadipocytes were serum starved in DMEM media. Following overnight incubation, media was harvested and filtered (Millipore, 0.45 mm). The conditioned media was concentrated using centrifugal filters (Amicon Ultra, 3K) at 14,000 g for 40 min. Secreted ETP was detected using α-mouse ETP polyclonal antibody compared to COL6 (Abcam, Ab6588). The primary antibodies were detected with secondary IgG-labeled with infrared dyes emitting at 700 and 800 nm and visualized on the Licor Odessey Infrared Scanner. The scanned results were analyzed using the Odessey v2.1 software (Licor Bioscience). The complete unedited blots for all Western blotting images in the main are shown in the Supplementary images.

Involution.

8-week-old females were housed individually upon pregnancy. Immediately after birth of their littermates, litter sizes were standardized to 6 pups per mother in order to prevent inter-mouse mammary gland variation. Involution was initiated by the removal of pups after 10 days of suckling. Mammary glands were collected for fixation at 0, 2, 3, 5 days after forced weaning and stained with H&E.

Assessment of Reproduction.

8-week-old female mice (5-9 mice/group) were mated with wild type males. Each female was monitored for resulting pregnancies. Litters were monitored for survival to weaning age.

Microarrays.

Total RNA was extracted from tumor tissue from 12-week-old PyMT and PyMT/endotrophin (n=12/group). Microarray experiments were performed by the UTSW microarray core facility. The Mouse Illumina Bead Array platform (47K array) (Illumina, Inc.) was used in this study. Gene lists and cluster analyses of the data sets were performed using Ingenuity Pathway Software (Ingenuity systems) and David Bioinformatics Resource (http://david.abcc.ncifcrf.gov/). Gene profiling data are available from GEO (http://www.ncbi.nlm.nih.gov/geo) under accession no. GSE39622.

In Vitro Angiogenesis.

A total 300 μl/well of growth factor reduced matrigel (BD biosciences) was plated into 12 well plates. MS-1 cells ($5 \times 10^4$) were seeded and images were acquired 3-4 hours after incubation with the conditioned media indicated.

Luciferase Reporter Assay.

Cell lysates were harvested and analyzed for luciferase reporter assays following the manufacturer's protocol (Applied Biosystems, The Dual-Light luminescent reporter gene assay). The pGL3-SBE reporter, pGL3-βGal and indicated ETP constructs; pRA-ctrl (empty vector), pRA-sETP (secretion form of ETP) and pRA-ETP (intracellular form of ETP) were transiently transfected into Met-1 cells. 1 day after transfection, TGFβ (5 ng/ml) with either 1D11 (5 μg/ml) or IgG (5 μg/ml) was added overnight. Total cell lysates were analyzed for luciferase activity.

Example 2

Inhibition of Endotrophin, a Cleavage Product of Collagen VI, Confers Cisplatin Sensitivity to Tumors The therapeutic benefit of cisplatin in human cancer treatments is often limited due to resistance. Thiazolidinediones (TZDs) (peroxisome proliferator activated receptor γ agonists) show beneficial effects in the context of cisplatin-based chemotherapy. Previous work indicates that collagen-Vla3 (COL6A3) plays an important role in cisplatin resistance. However, the detailed molecular mechanisms underlying the correlations between COL6A3 and cisplatin resistance remained elusive prior to this study. The goal of this study was to elucidate the roles of endotrophin, a cleavage product of COL6A3, in cisplatin resistance and elaborate further to see if endotrophin modulates the beneficial effects of TZDs in cisplatin therapeutics in breast cancer.

Endotrophin, which is mainly secreted from stromal adipocytes in the tumor microenvironment, was demonstrated herein to confer a high degree of cisplatin resistance by enhancing epithelial-mesenchymal transition, fibrosis and angiogenesis. Furthermore, the powerful beneficial effects of TZDs on cisplatin sensitivity are mainly due to a marked inhibition of endotrophin-mediated activities. This suggests that TZDs directly mediate enhanced cisplatin chemosensitivity through a downregulation of endotrophin. Treatment with an endotrophin neutralizing monoclonal antibody in combination with cisplatin very effectively inhibits tumor growth of allografts of MMTV-PyMT tumors.

It is well appreciated that chemo-responsiveness is changed over the course of tumor progression, and it varies greatly between different tumor types; identifying the critical players mediating this chemo-resistance is important to devise better therapeutic strategies. The results herein have important clinical implications, as endotrophin is increased in tumors upon chemotherapy, and the associated EMT is a predictor of chemo-resistance. Therefore, endotrophin levels can be a strong prognostic marker with respect to the tumor response to combination therapy of TZDs with cisplatin, and the neutralization of endotrophin can further improve the therapeutic response to combination therapy.

Cisplatin Augments COL6A3 Levels, Whereas TZDs Cause a Reduction.

Figures 19A, 19B:
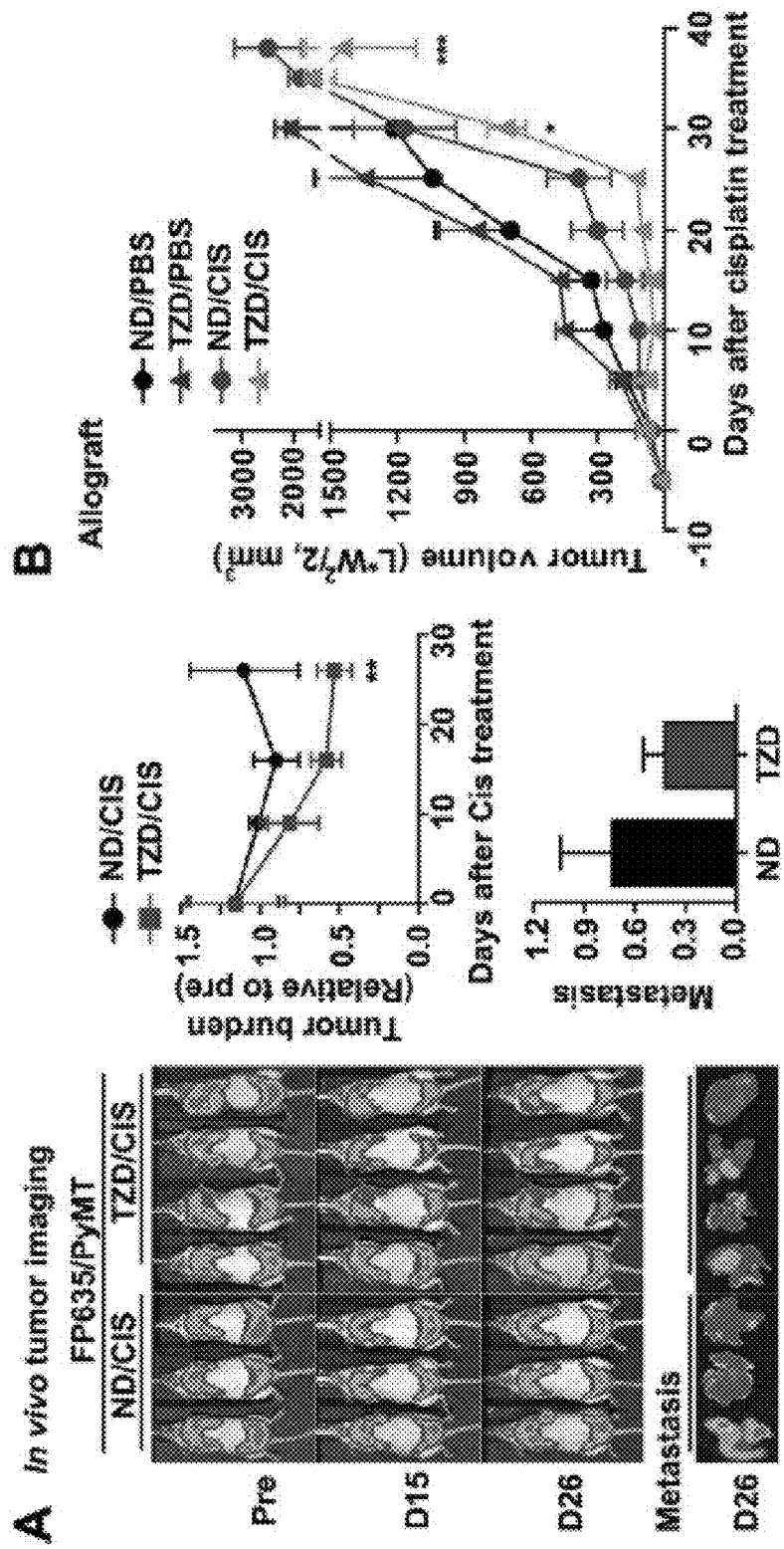
FIGS. 19A-19F. TZD augments cisplatin sensitivity and correlates with the COL6A3 levels.
Figures 23A, 23B:
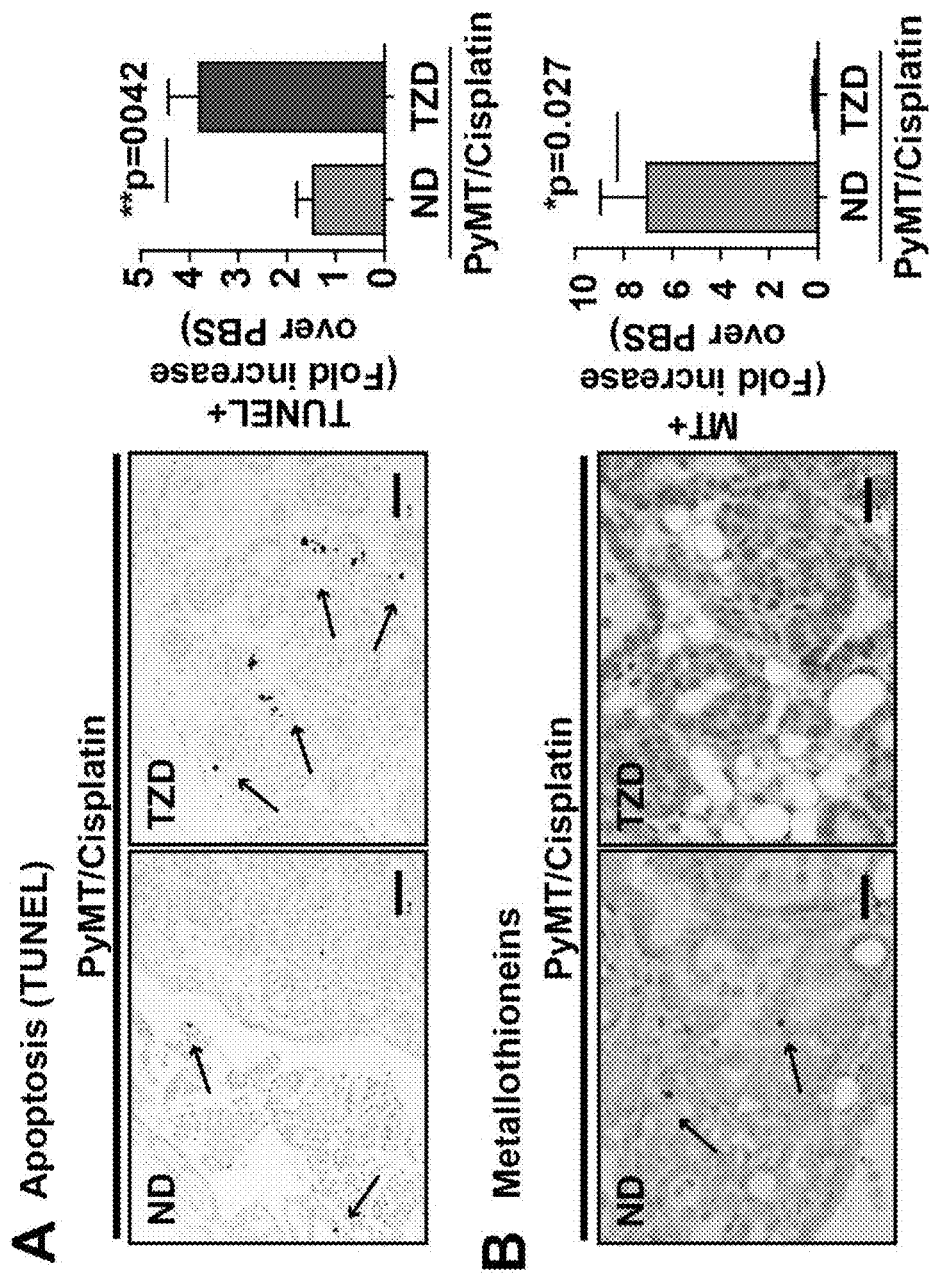
FIGS. 23A-23B: TZD confers beneficial effects on cisplatin treatment in mammary tumors. Met-1 cancer cells ($0.5 \times 10^6$ cells/mouse) were implanted into wild-type mice and TZD (20 mg/kg) was given by diet and cisplatin (1 mg/kg) was intraperitoneally (ip.) injected every 5 days from 30 days post implantation (n=8/group). *p<0.001 vs. ND by 2-way ANOVA. Tumor tissues from PyMT mice given TZD or normal diet (ND) diet were histologically assessed. Representative images and quantification for TUNEL staining (FIG. 23A), showing increased cancer cell apoptosis by TZD combination in cisplatin. Data represent mean±SD (n=5/group). p=0.0042 ND vs. TZD by unpaired student t-test. Scales: 50 μm. Representative metallothioneins staining and quantification (FIG. 23B), showing a higher signal in tumor tissues following cisplatin, which is efficiently suppressed by TZD combination. Data represent mean±SD (n=5/group). *p=0.002 ND vs. TZD by unpaired student t-test. Arrows indicate staining positive cells. Scales: 25 μm.

To assess the beneficial effects of TZD (using mostly the TZD rosiglitazone) on platinum-based chemotherapies in mammary tumor models in vivo, either a MMTV-PyMT ("PyMT") mouse model or an allograft of Met-1 cancer cells (originating from MMTV-PyMT mammary tumors) that was transplanted into isogenic wild-type mice were used. To visualize system-wide tumor burden in vivo, an infrared-fluorescent protein (FP635) overexpressing transgene driven by the MMTV promoter (MMTV-FP635) was introduced into PyMT mice (Park & Scherer, 2012b). Tumor regression was monitored by utilizing fluorescence scanning over the course of cisplatin treatment (FIG. 19A). Tumor growth was efficiently reduced and pulmonary metastasis were also slightly attenuated in PyMT mice exposed to TZDs (20 mg/kg) in combination with cisplatin (1 mg/kg) compared to those mice given only cisplatin (FIG. 19A). Met-1 allografts showed a better response to the combination of TZD with cisplatin than the response seen in PyMT mice (FIG. 19B). This may be due to PPARγ-dependent activation of intrinsic oncogenic pathways, such as wnt, or contributions of the tumor stroma responding to a prolonged treatment of TZDs, which may counteract their beneficial effects on cisplatin in the PyMT mice (Saez et al, 2004). In addition, it was previously shown that TZDs are potent inducers of the adipokine adiponectin that were implicated in enhanced angiogenesis and improved cellular survival (Landskroner-Eiger et al, 2009). Subsequent histological analysis of tumor tissues indicated that cancer cell death was increased about 2-fold with the TZD combination (FIG. 23A). The fact that the metallothionein (MT) levels, a molecular marker for drug resistance (Theocharis et al, 2003), are suppressed by the TZD combination with cisplatin, is well appreciated (Girnun et al, 2007). Consistently, immunostaining for MT in tumor tissues of PyMT mice showed that cisplatin treatment significantly increased the MT levels, and this was suppressed in the presence of TZD (FIG. 23B). As such, the PyMT mice serve as a useful model to assess the beneficial effects of TZDs in platinum-based therapeutics in vivo.

Figures 19C, 19D:
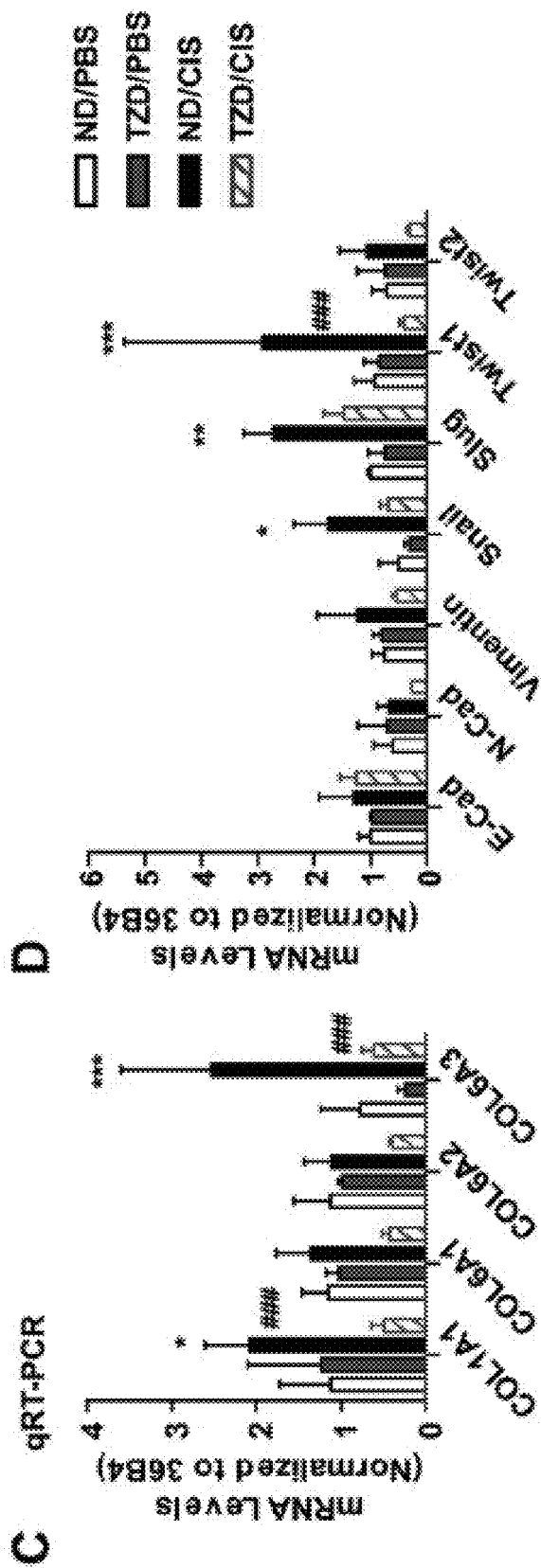

To see whether COL6 is involved in the beneficial effects of TZDs on platinum-based therapy, the expression levels were determined for COL6 in response to chemotherapy. The mRNA levels of COL6A3 in tumor tissues of PyMT mice were significantly increased in response to cisplatin treatment; this increase was dramatically suppressed by combination with TZDs (FIG. 19C). These results indicate that COL6A3 levels may have an impact on the degree of chemo-sensitivity between TZDs and platinum in vivo.

Cisplatin Augments Epithelial-Mesenchymal Transition, Whereas TZD Attenuates it.

Figures 19E, 19F:
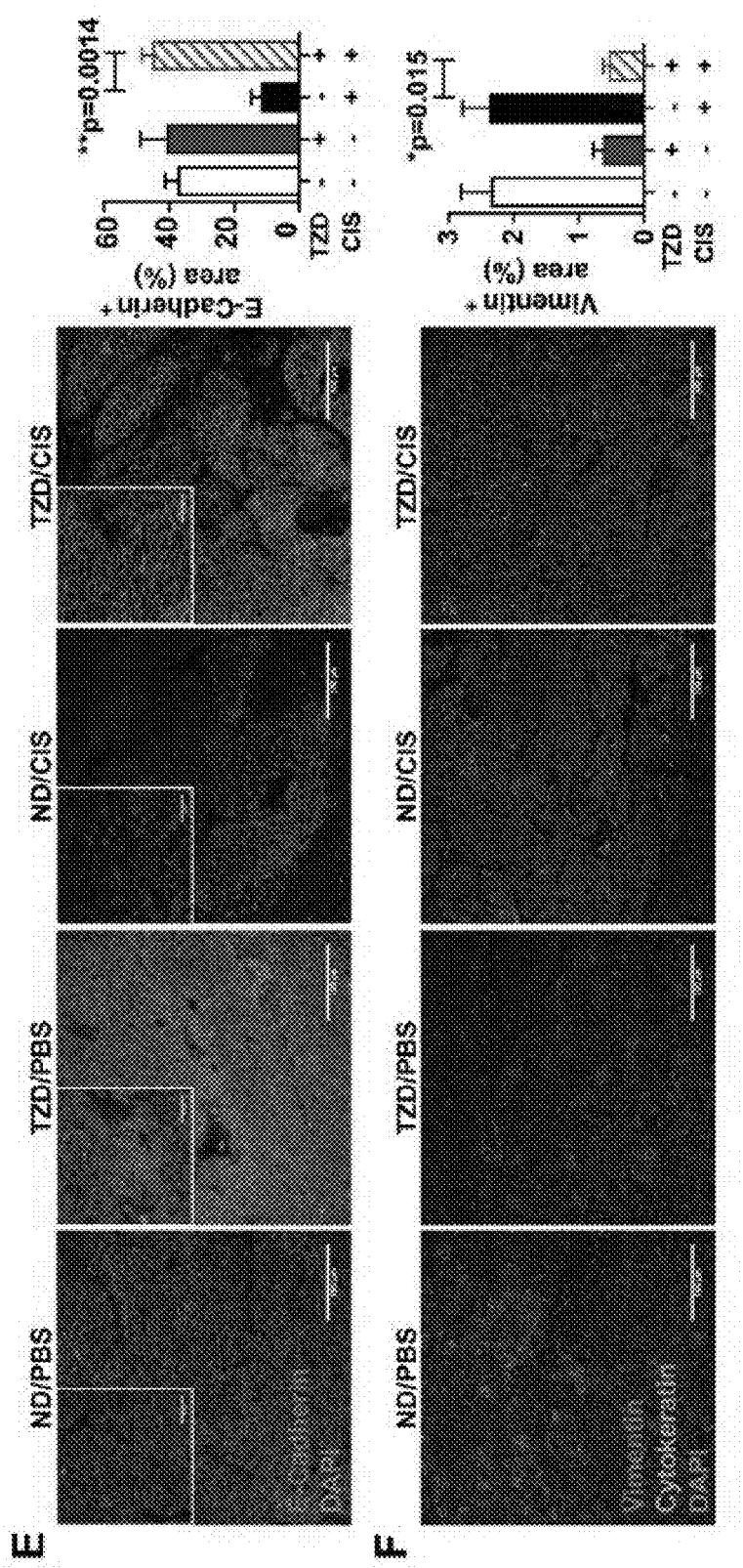

The EMT process in tumor tissues is well known to contribute to an acquired drug resistance (Arumugam et al, 2009; Latifi et al, 2011). This suggests a fundamentally reduced sensitivity of mesenchymal-like cells to chemo-therapeutic approaches. Targeting the critical factors that contribute to the EMT process, such as Snail, Slug and Twist1, has beneficial effects for cisplatin-based therapies (Haslehurst et al, 2012; Zhu et al, 2012), further generalizing a model that correlates the degree of cisplatin sensitivity with the EMT status of tumor tissues. Moreover, TZDs have been suggested to suppress EMT, resulting in a reduced level of tumor metastasis (Reka et al, 2010). In the mouse models, the mRNA levels for transcription factors associated with EMT, such as Snail, Slug and Twist1, were significantly increased in response to cisplatin exposure. The increases in critical mediators of EMT, especially the increased levels of Twist1, were significantly attenuated by combination treatment with TZD (FIG. 19D). This supports the idea that cisplatin induces EMT in cancer cells, and that the beneficial effects of TZDs in the context of cisplatin exposure are partly mediated by suppression of EMT. This is substantiated by immunohistochemistry with critical EMT markers. Immunostaining with antibodies against EMT markers that include either the loss of E-cadherin or an increase in vimentin expression, showed a significant increase of EMT following cisplatin treatment in tumor tissues, whereas levels of E-Cadherin were sustained in TZD and cisplatin treated group (TZD/CIS) comparable to control tissues (ND/PBS) (FIG. 19E). In parallel, cisplatin-induced increases in vimentin levels were also significantly reduced by combination with TZD (FIG. 19F). These observations led to studies to test whether endotrophin plays a critical role in the cisplatin-driven increase of EMT, as endotrophin plays a generalized role in EMT in tumor tissues (Park & Scherer, 2012b). It was examined whether the TZD-mediated decrease in COL6A3 levels (FIG. 19C) can be connected to the TZD-mediated enhanced cisplatin sensitivity through suppression of the endotrophin-induced EMT.

Endotrophin, a Cleavage Product of COL6A3, Confers Cisplatin Resistance in Tumor Tissues.

Figures 20A, 20B, 20C:
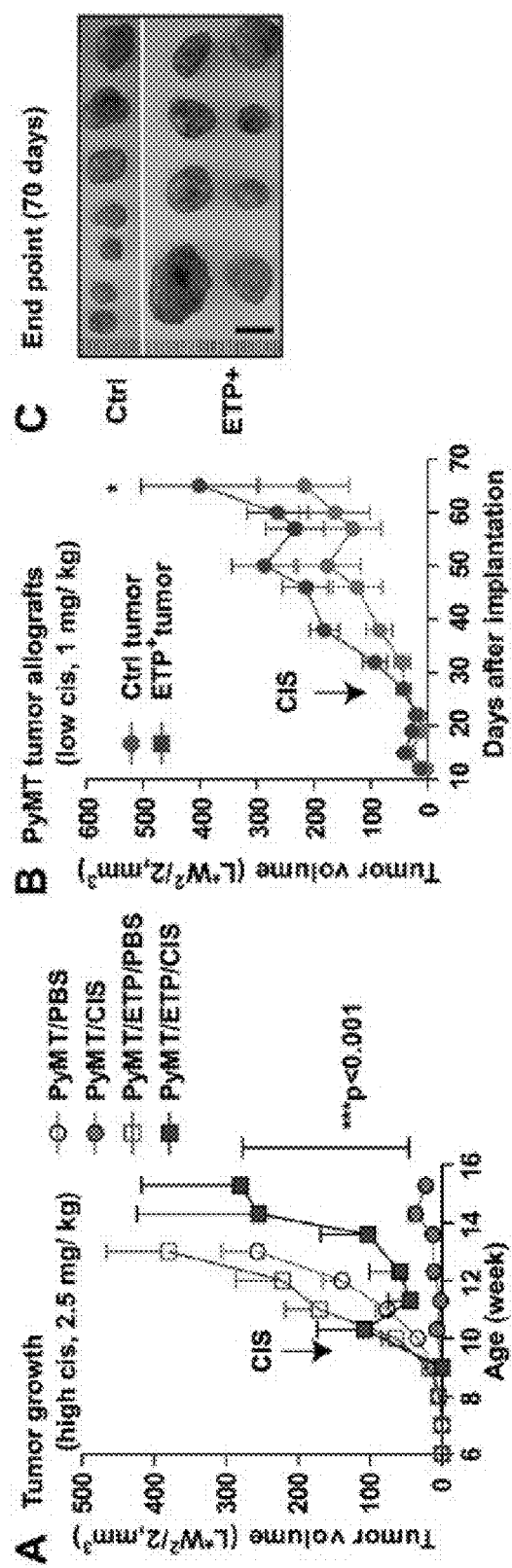
FIGS. 20A-20C. Endotrophin overexpression confers cisplatin resistance in PyMT mice.

It has been previously shown that MMTV-Endotrophin mice bred to the PyMT mice (PyMT/endotrophin) develop more aggressive tumors compared to PyMT mice (Park & Scherer, 2012b). Here, these mice were further examined to see whether endotrophin induces cisplatin resistance. PyMT/endotrophin transgenic mice were treated with either PBS or cisplatin and compared to PyMT control littermates. Primary tumor growth of PyMT mice was effectively curbed with a high dosage of cisplatin treatment (2.5 mg/kg, ip. twice a week), whereas PyMT/endotrophin mice were resistant to the effects of cisplatin treatment (FIG. 20A). Similarly, allografts of tumor pieces taken from PyMT and PyMT/endotrophin mice transplanted into isogenic wild-type mice showed that endotrophin$^+$-tumors were more resistant to a lower dosage of cisplatin treatment (1 mg/kg, ip. twice a week) compared to control (Ctrl)-tumors (FIG. 20B-20C). These results further corroborate a direct connection of cisplatin-induced high levels of endotrophin expression and chemo-resistance.

Figures 21A, 21B, 21C:
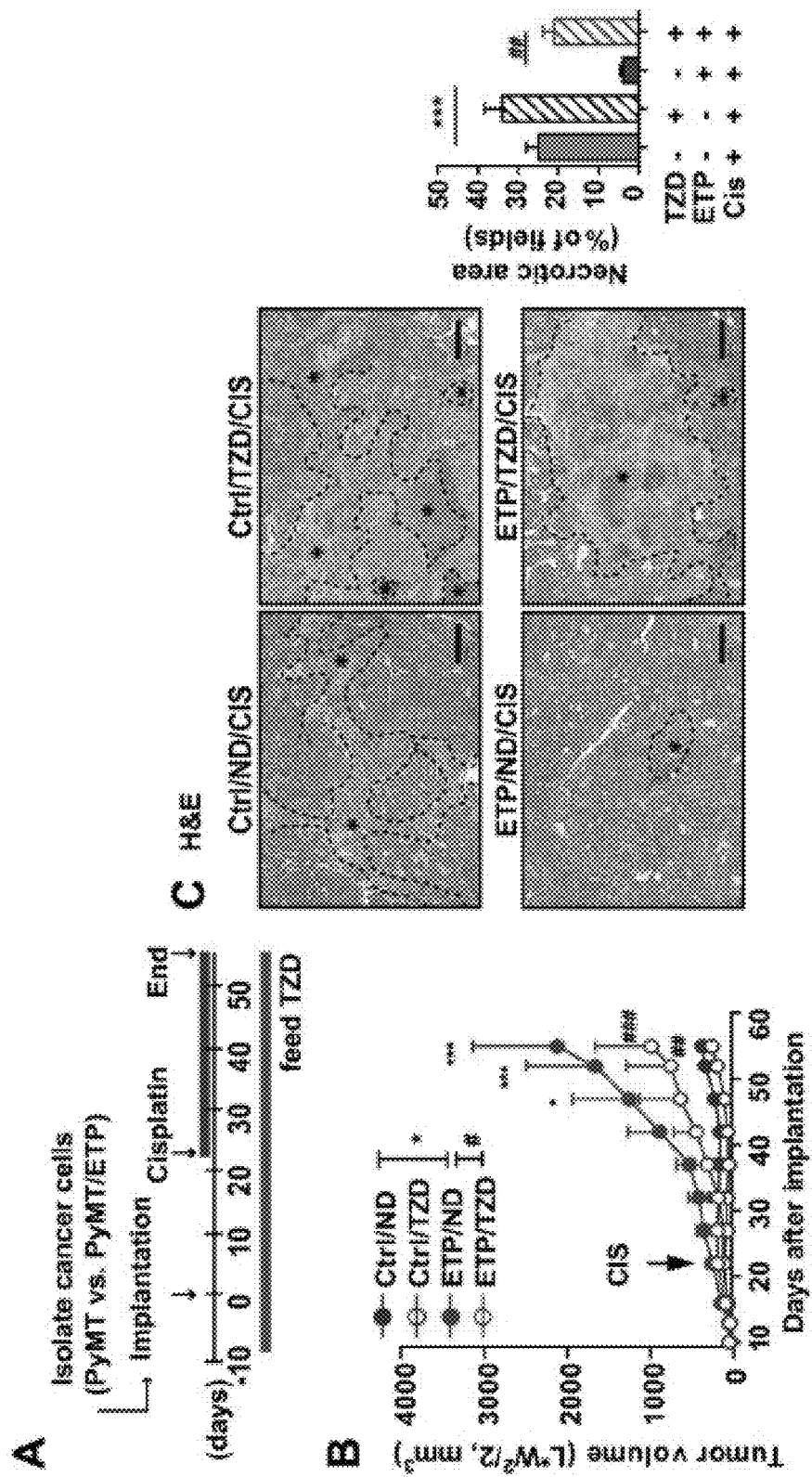
FIGS. 21A-21F. TZD synergizes cisplatin sensitivity through suppression of endotrophin-mediated EMT, fibrosis and vasculature.
Figures 21D, 21E, 21F:
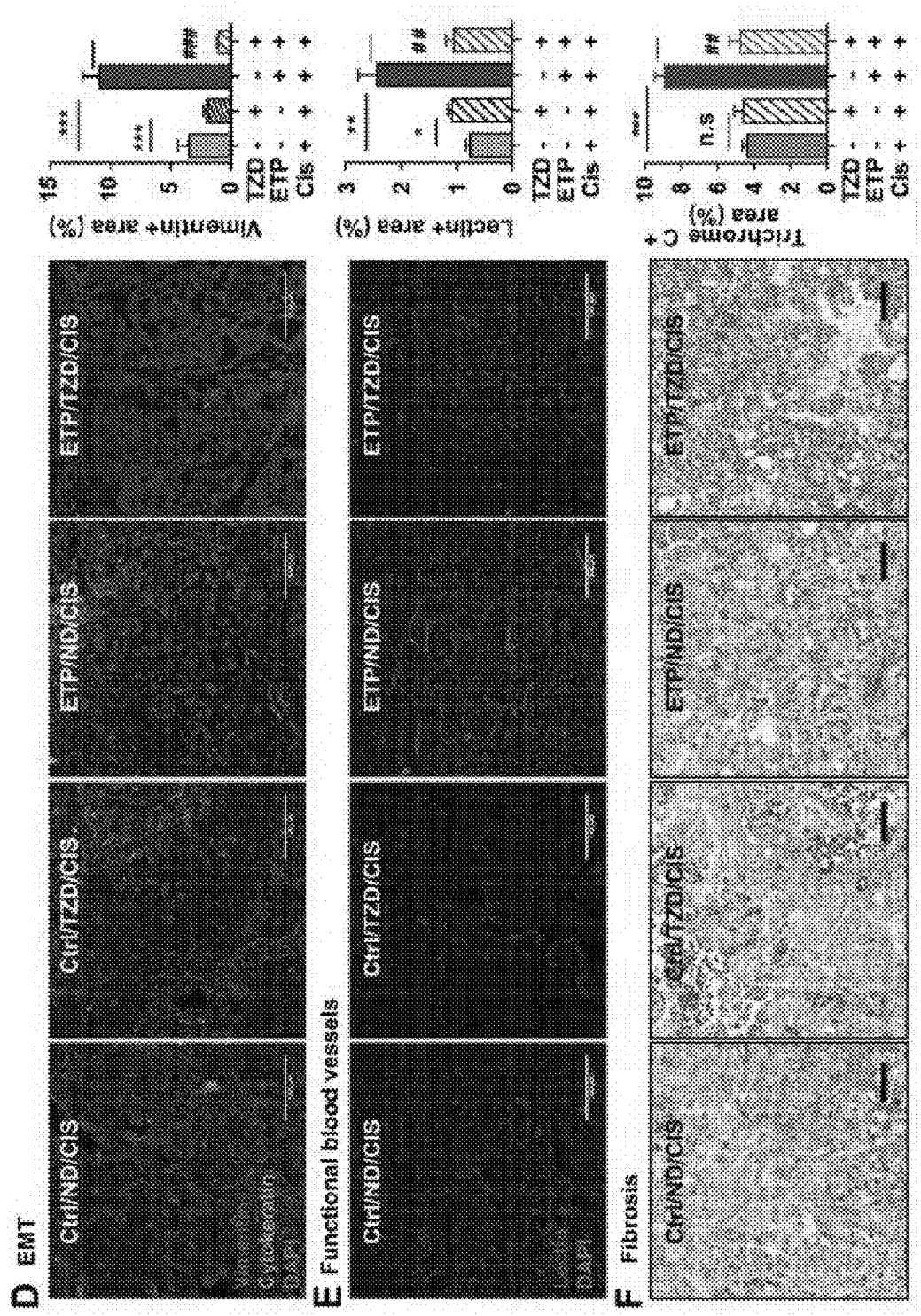

Acquisition of the Beneficial Effects of TZDs to Cisplatin Critically Depends on the Endotrophin Levels It has been shown above that the beneficial effects of TZDs on the cisplatin therapeutic efficiency are linked to endotrophin down-regulation. Do the TZD effects converge on to the endotrophin-mediated signaling pathways? Both mRNA and protein levels for endotrophin were dramatically reduced with the TZD and cisplatin combination treatment. Therefore, it was assessed whether endotrophin overexpression could abolish the beneficial effects of TZD on cisplatin efficacy. Endotrophin$^+$-cancer cells originating from PyMT/endotrophin mice were compared to Ctrl-cancer cells from PyMT mice, and were implanted into wild-type mice. TZD was given to wild-type hosts 10 days prior to implantation and cisplatin was injected intraperitoneally every 5 days, starting 3-weeks post implantation when the tumor volume reached 100 mm$^3$ (FIG. 21A). Endotrophin$^+$-tumors were more resistant to cisplatin treatment compared to Ctrl-tumors (FIG. 21B, Ctrl/ND vs. ETP/ND), and this increase was markedly attenuated by the combination with TZD (FIG. 21B, ETP/ND vs. ETP/TZD). This suggests that TZD influences not only the endotrophin expression per se, but it may also impact the downstream pathways of endotrophin. Endotrophin-independent pathways may be also contributing, or TZD may act on host endotrophin levels in this transplantation paradigm. Defined necrotic lesion areas, as assessed by H&E stains, were significantly decreased in endotrophin$^+$-tumors. This phenomenon was however reversed by combined treatment of cisplatin with TZD (FIG. 21C). This suggests that a combination of TZD with cisplatin confers sensitivity to endotrophin$^+$-tumors. Accordingly, the significant endotrophin-mediated increase on EMT, angiogenesis and fibrosis seen in endotrophin$^+$-tumors was suppressed by the combination of cisplatin with TZD, as judged by immunostaining for vimentin (EMT), lectin perfusion (angiogenesis) and Masson's trichrome C stain (fibrosis), respectively (FIGS. 21D-21F). This suggests that TZD attenuates the downstream signaling pathways induced by endotrophin.

The Suppression of Endotrophin Activity can be Achieved by Either Using TZD or Anti-Endotrophin Monoclonal Antibodies, Both of which Sensitize Tumors to Cisplatin Therapeutics.

Figures 22A, 22B:
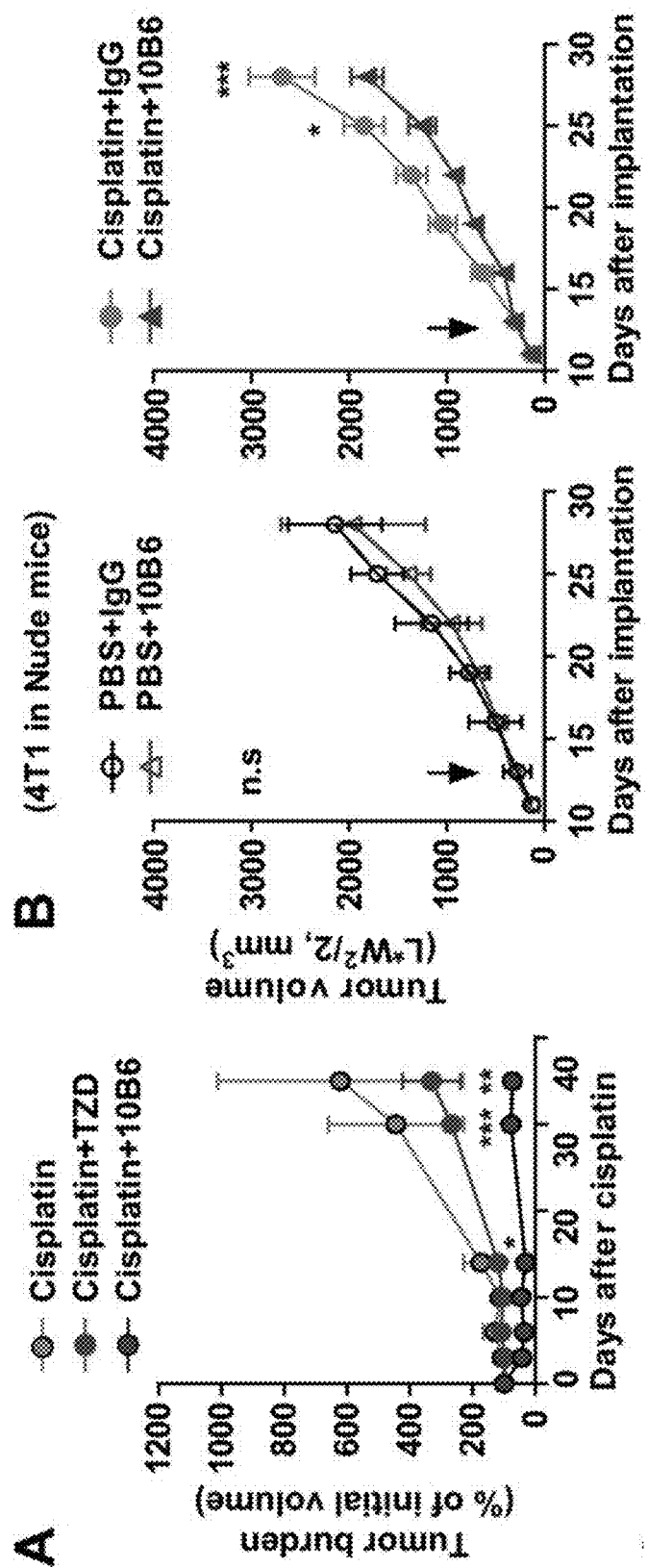

As a last step, therapeutic potential of a previously described endotrophin neutralizing antibody (clone 10B6) on cisplatin sensitivity was determined. Tumor pieces taken from PyMT mice were implanted into wild-type mice and treated with cisplatin alone or in combination with either TZD or 10B6 once the tumor volume reached 100 mm$^3$. Tumor regression was monitored for 2-months post implantation. Both TZD and 10B6 treatment are demonstrated to efficiently sensitize the tumors to cisplatin treatment (FIG. 22A). Xenograft models were utilized with the mammary carcinoma cell line 4T1, which is highly invasive and rapidly metastasizes throughout the body, resembling human stage IV breast cancer (Pulaski & Ostrand-Rosenberg, 1998). Nude mice were injected with 4T1 cells in mammary adipose tissues. Treatment with cisplatin was initiated when the tumor volume reached at 100 mm$^3$. Treated was combined with either control IgGs or 10B6. Treatment of either 10B6 or cisplatin alone for 28-days barely inhibited primary tumor growth of 4T1, while treatment with cisplatin combined with 10B6 induced a moderate, but significant inhibition in comparison to cisplatin or 10B6 alone (FIG. 22B). However, most prominent effects of combination treatment (cisplatin and 10B6) were observed on metastatic growth. The metastatic burden on the lung, as determined by assessing the metastatic lesion areas, was significantly attenuated by combination treatment relative to individual treatments (FIG. 22C). Notably, the combination of cisplatin and endotrophin neutralization showed a particularly higher efficacy on metastatic growth than either treatment alone for late stages of 4T1 carcinomas. Furthermore, a subset of genes related to EMT that includes Vimentin, Twist1 and S100A4 levels were also significantly decreased by the combination treatment (FIG. 22D). This indicates that inhibitory effects of combination treatment of cisplatin with endotrophin neutralization mediate a suppression of EMT, lack of which results in loss of crucial traits for metastatic growth.

DISCUSSION

The cellular responses were tested to endotrophin on chemo-responsiveness in mammary tumors treated with cisplatin. It was demonstrated that a robust response of cancer cells to cisplatin is highly dependent on the presence of the endotrophin-driven EMT process. Endotrophin overexpression, leading to enhanced EMT, causes cisplatin resistance. The data presented here suggests that determining endotrophin levels in association with the EMT status is critical for predicting cisplatin response. Higher levels of endotrophin occur in advanced metastatic breast cancers (Iyengar et al, 2005) and contribute to the poor chemo-response. It also suggests that this subset of tumors is likely to undergo EMT, which plays a major role in tumor progression, metastasis and multi-drug resistance in various epithelial cancer cells (Haslehurst et al, 2012; Latifi et al, 2011; Rosano et al, 2011). Furthermore, it is proposed that obesity is one of the major risk factors to provide an endotrophin-enriched tumor microenvironment, because it is mainly secreted from adipose tissue and elevated in dysfunctional adipose tissue. Therefore, the endotrophin-mediated EMT described here may also be predictive of a poor chemotherapeutic response in other types of cancers.

It has been appreciated that there is an enormous degree of ECM remodeling going on in response to chemotherapy, and this in turn has an impact on drug penetration, which critically affects chemo-sensitivity. In addition, increased tissue stiffness seems to confer survival signals to cancer cells through enhanced anchoring of cancers to ECMs. Beyond these purely mechanical roles of ECM remodeling, here endotrophin was found to act as a signaling molecule leading to an enhanced EMT process, resulting in cisplatin resistance.

The beneficial effects of the combination of TZDs with platinum-based chemotherapy are appreciated. Based on the data herein, TZD monotherapy fails to have an impact on tumor progression in PyMT mice, and in fact further enhances growth. This is consistent with clinical reports that failed to see an impact on the malignancies of epithelial cancer cells (Burstein et al, 2003; Kulke et al, 2002; Smith et al, 2004). However, TZDs in combination with cisplatin is highly beneficial. How do TZDs enhance cisplatin effectiveness? Here, it is shown that the beneficial effects of TZDs on cisplatin therapies are due to marked reduction of the endotrophin levels. This attenuates the downstream consequences of endotrophin signaling, including a suppression of EMT, fibrosis and angiogenesis, thereby leading to an increase of chemo-sensitivity (FIG. 22E). Therefore, a treatment criterion for a TZD/cisplatin combination therapy would be high levels of endotrophin in association with EMT, due to the fact that the beneficial effects of TZDs are acquired through a direct suppression of endotrophin-induced EMT. Along those lines, it is shown that neutralizing endotrophin activity through the use of neutralizing monoclonal antibodies during cisplatin treatment effectively inhibits the tumor growth and metastasis.

In summary, a rodent model was employed for a chemotherapeutic tumor response, and demonstrated that the endotrophin-mediated induction of the EMT results in chemo-resistance. Furthermore, the beneficial effects of TZDs on cisplatin-based therapies are shown to be mediated through the suppression of this pathway. These results provide a direct explanation for previous correlations reported in the context of poor responses to platinum-based chemotherapy in tumors expressing high levels of COLE. This also suggests that endotrophin levels as a promising predictive marker to decide if a TZD combination should be initiated along with a platinum-based therapeutic approach.

Materials and Methods

Animal Experiments.

All animal experiments were approved by the Institutional Animal Care and Research Advisory Committee at the University of Texas Southwestern Medical Center. MMTV-PyMT mice (Guy et al, 1992) were used as a mouse mammary tumor model. MMTV-Endotrophin transgenic mice and MMTV-FP635 (Infrared fluorescent protein FP635) transgenic mice were generated as previously described in the study (Park & Scherer, 2012a). All experiments were conducted using littermate-controlled female mice. All animals used in this study are in a pure FVB background.

Reagents.

Cisplatin (sigma, 479306) was diluted to 1 mg/ml in PBS and was sonicated briefly before injection. The peroxisome proliferator-activated receptor gamma (PPARγ) agonist rosiglitazone (Avandia, GlaxoSmithKline) was given by diet inclusion at a dose of 20 mg/kg/day BW. Anti-mouse endotrophin monoclonal antibodies (10B6, 100 μg/mouse) were administered by intraperitoneal injection.

Histological Analysis.

Formalin-fixed paraffin-embedded tissue sections were used for immunostaining Deparaffinized tissue slides were stained with rabbit anti-mouse endotrophin, metallothionein (Abcam, Ab12228), E-cadherin (Cell signaling, 24E10), Vimentin (Cell signaling, D21H3) and cytokeratin (Cell Signaling, #4545). For immunofluorescence, fluorescence labeled secondary antibodies were used and counterstained with DAPI. Images were acquired using the Leica confocal microscope and analyzed with ImageJ software. For immunohistochemistry, the reaction was visualized by the DAB Chromogen-A system (Dako Cytomation) and counterstained with hematoxylin. Images were acquired using the Nikon Cool Scope. TUNEL assay was according to the manufacturer's protocol (Trevigen, Inc). To assess functional blood vessels formation in tumor tissues, mice were injected with biotinylated tomato-lectin (100 μg, i.v) (Vector laboratories, CA) and perfused lectin was visualized by a Cy3-labeled streptoavidin. H&E staining and Masson's Trichrome C staining were performed by Dr. John Shelton at the University of Texas Southwestern Medical Center. Histological analysis was performed with pathologists in the UTSW pathology core facility.

Quantitative RT-PCR.

Total RNA was isolated following tissue homogenization in Trizol (Invitrogen, Carlsbad, Calif.) using a TissueLyser (Qiagen, Valencia, Calif.) and isolated using the RNeasy kit (Qiagen). Total RNA (1 μg) was reverse transcribed with SuperScript III reverse transcriptase (Invitrogen). Quantitative real-time PCR (qRT-PCR) was performed in the Roche Lightcycler 480. For all qRT-PCR experiments, the results were calculated using the AACt method using 36B4 to normalize. Primers for COL1A1, COL6A1, COL6A2, and COL6A3 were followed in previous report (Khan et al, 2009). Other primer sequences used in this study are listed in Table 1 below.

TABLE 1

| Gene | Sense | Antisense |
| --- | --- | --- |
| Snail (Snai1) | CCCTTCAGGCCACCTTCTTT GAGGT (SEQ ID NO: 19) | GTCCAGTAACCACCC TGCTG (SEQ ID NO: 20) |
| Slug (Snai2) | CTGTATGGACATCGTCGGCA G (SEQ ID NO: 21) | ACTTACACGCCCCAA GGATG (SEQ ID NO: 22) |
| Twist1 | CGGCCAGGTACATCGACTTC (SEQ ID NO: 23) | TGCAGCTTGCCATCTT GGAG (SEQ ID NO: 24) |
| Twist2 | TCAGCAAGATCCAGACGCT C (SEQ ID NO: 25) | CTGAGATGTGCAGGT GGGTC (SEQ ID NO: 26) |
| E-Cadherin (Cdh1) | CGATTACGAGGGCAGTGGT T (SEQ ID NO: 27) | AGTCCCCTAGTCGTCC TCAC (SEQ ID NO: 28) |
| N-Cadherin (Cdh2) | GGCAATCCCACTTATGGCCT (SEQ ID NO: 29) | TCCGTGACAGTTAGG TTGGC (SEQ ID NO: 30) |
| Vimentin | GCCAGCAGTATGAAAGCGT G (SEQ ID NO: 31) | ACCTGTCTCCGGTACT CGTT (SEQ ID NO: 32) |
| S100A4 | TTGTGTCCACCTTCCACAAA (SEQ ID NO: 33) | TGTTGCTGTCCAAGTT GCTC (SEQ ID NO: 34) |
| COL6A3-N | ACGCCCATCACCACTCTAAC (SEQ ID NO: 35) | CTAAACTGCACGACC CCAAT (SEQ ID NO: 36) |
| 36B4 | GGCATGCGGCCCGTCTCTC (SEQ ID NO: 37) | CTTCCCTGGGCATCAC GGCG (SEQ ID NO: 38) |

Primary Culture of Mammary Cancer Cells and Implantation.

Mammary epithelial cancer cells were isolated as described in previous report (Park et al, 2010). 1 day after cell culture, same amount of cancer cells were counted and implanted into inguinal fat-pad of 8- to 10-week-old indicated recipient mice by intraductal injection. Tumor growth was determined from 10 days after implantation and twice a week over the course of tumor progression.

Analysis of Tumor Progression.

Tumor onset was monitored twice weekly by palpation. Tumor sizes were measured with a digital caliper twice weekly and the volumes were calculated as (length×width)/2. Inguinal tumors were weighted to determine tumor burden. Animals were sacrificed when the tumor burden visibly affected the host or when the tumors reached the IACUC predetermined limit of 20 mm along one axis.

Tumor Imaging.

Infrared fluorescence expressing MMTV-PyMT mice (FP635/PyMT) were imaged by IVIS scanner (Caliper lifesciences) and signal intensity was analyzed with Living image v.3.2 (Caliper lifesciences).

Statistical Analyses.

All data represent mean±SD. Data were analyzed by 2-way ANOVA followed by Newman-Keuls multiple comparison test or by Student's t-test and Mann-Whitney t-test, as appropriate with GraphPad Prism v.5 software. P-value less than 0.05 was considered as statistical significance.

Example 3

Antibodies

Figure 28A:
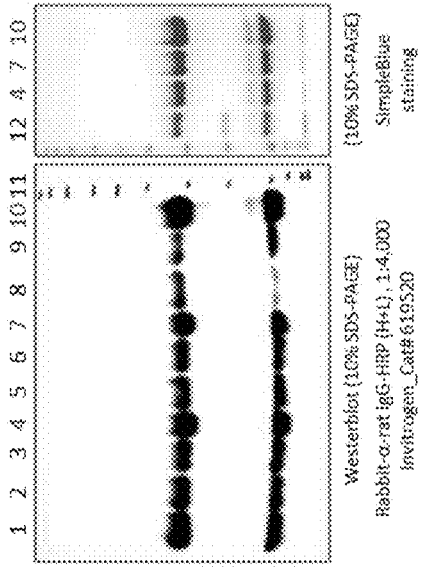
Figure 28A:
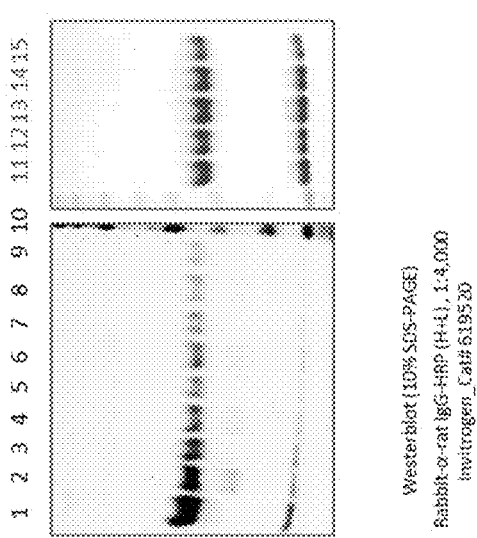
Figure 28A:
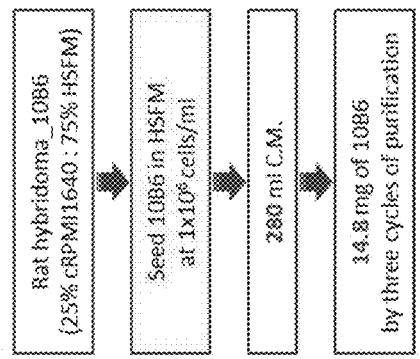
Figure 28A:
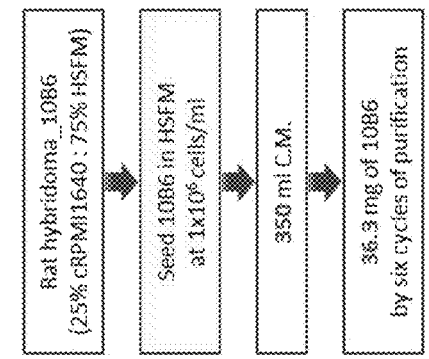
Figure 28B:
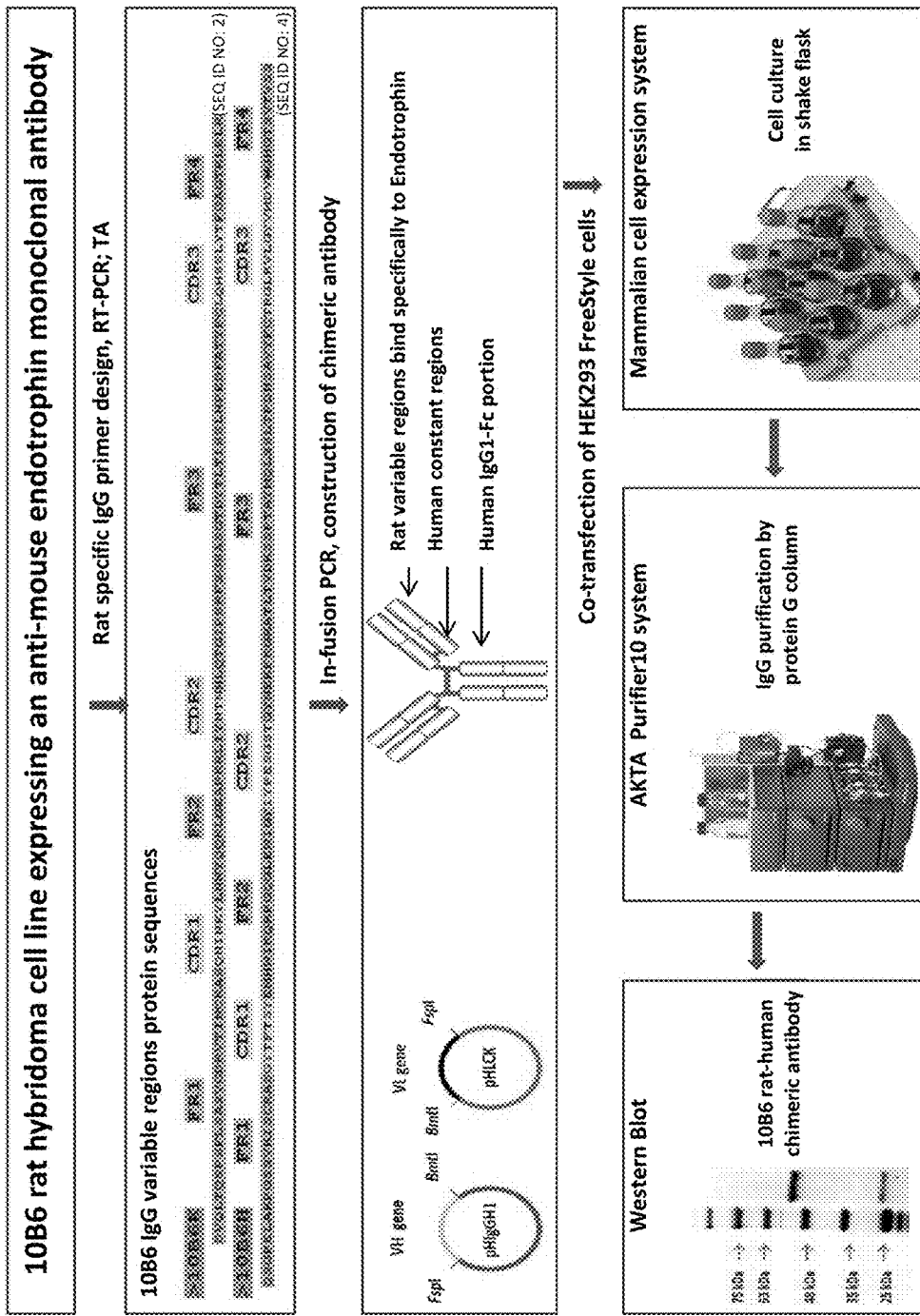

As shown in FIGS. 28A-28C, an anti-mouse endotrophin monoclonal antibody (10B6 mAb) was prepared using standard hybridoma technology. FIG. 28A illustrates the purified 10B6 antibody produced by a rat hybridoma cell line expressing an anti-mouse endotrophin monoclonal antibody. FIG. 28B illustrates the transient expression of cloned 10B6 antibody as a rat/human chimera in HEK293 cells. FIG. 28C shows the 10B6 Kappa chain sequence (coding DNA (SEQ ID NO: 1) and amino acid (SEQ ID NO: 2) sequences) and alignment with IGKV22S7*01. Based on the alignment, the 3 CDR's of the 10B6 Kappa chain are: QNINKY (CDR1; SEQ ID NO: 7), NTN (CDR2) and LQHSSLYT (CDR3; SEQ ID NO: 8). FIG. 28D shows the 10B6 heavy chain sequence (coding DNA (SEQ ID NO: 3) and amino acid (SEQ ID NO: 4) sequences) and alignment with IGHV1S12*01. Based on the alignment, the 3 CDR's of the 10B6 heavy chain are: GYTFTSYE (CDR1; SEQ ID NO: 9), IYPESGST (CDR2; SEQ ID NO: 10) and TRGLRVLGYVMDV (CDR3; SEQ ID NO: 11).

An anti-human endotrophin monoclonal antibody is also being prepared using standard hybridoma technology. Such an antibody can be further modified into, e.g., a chimeric antibody or a humanized antibody. The antibody can recognize the human endotrophin target, and provide therapeutic benefits in human cancer patients, such as increasing sensitivity to platinum-based chemotherapy in tumors (or overcoming platinum-resistance in chemotherapy, alone or together with TZD), and reducing angiogenesis and/or fibrosis in tumor progression. Further, such an antibody can be used as a predictive marker to decide if TZD combination should be initiated along with a platinum-based therapeutic approach.

Example 4

Metabolic Effects

A follow up study on the carboxy-terminal endotrophin cleavage product of Co16a3 revealed that abundant secretion of endotrophin from 3T3-L1 preadipocytes and fully differentiated adipocytes. Furthermore, it is demonstrated that endotrophin is up-regulated in the obese state. As an adipocyte-derived and an obesity-associated factor, the direct action of endotrophin on adipose tissue dysfunction is also important, even in the absence of a tumor. The local effects of adipocyte derived endotrophin were examined, and consequently also its impact on systemic metabolic dysregulation. Endotrophin induced by obesity may be associated with adipose tissue fibrosis, macrophage chemotaxis, inflammation and insulin resistance. This is indeed the case as confirmed by the following experiments.

Over-Expression of Endotrophin in Adipose Tissue Increases Body Weight Gain, Impairs Insulin Sensitivity and Causes Abnormal Adipokine Secretion in HFD-Challenged Mice.

To investigate the metabolic consequences of endotrophin overexpression in adipose tissue, transgenic mice and wild type littermate controls were challenged with HFD for 8 weeks. During the 8-week HFD exposure, endotrophin expressing mice gained more weight and exhibited reduced glucose tolerance and insulin sensitivity. Circulating adiponectin levels dramatically decreased while leptin levels in serum significantly increased in endotrophin transgenic mice. Collectively, over-expression of endotrophin specifically in adipose tissue impairs proper function of adipocytes and hence causes systemic metabolic dysfunction. To determine whether the endotrophin overexpression in AT also affects lipid metabolism, plasma triglycerides and non-esterified free fatty acid (NEFA) levels were measured. Both triglycerides and NEFA levels were significantly higher in endotrophin transgenic mice. Both triglyceride and cholesterol levels in the liver of endotrophin transgenic mice were dramatically increased. Liver histology also shows a clear-cut increase of lipid droplet number and size, indicating a severe liver steatosis in the transgenic animals. Over-expression of endotrophin therefore displays to a large extent abnormal in lipid metabolism and hence causes the steatosis in other tissues.

Neutralization of Endotrophin Activities in Diet Induced Obese Mice Improves Whole Body Insulin Sensitivity.

Figures 24A, 24B, 24C, 24D:
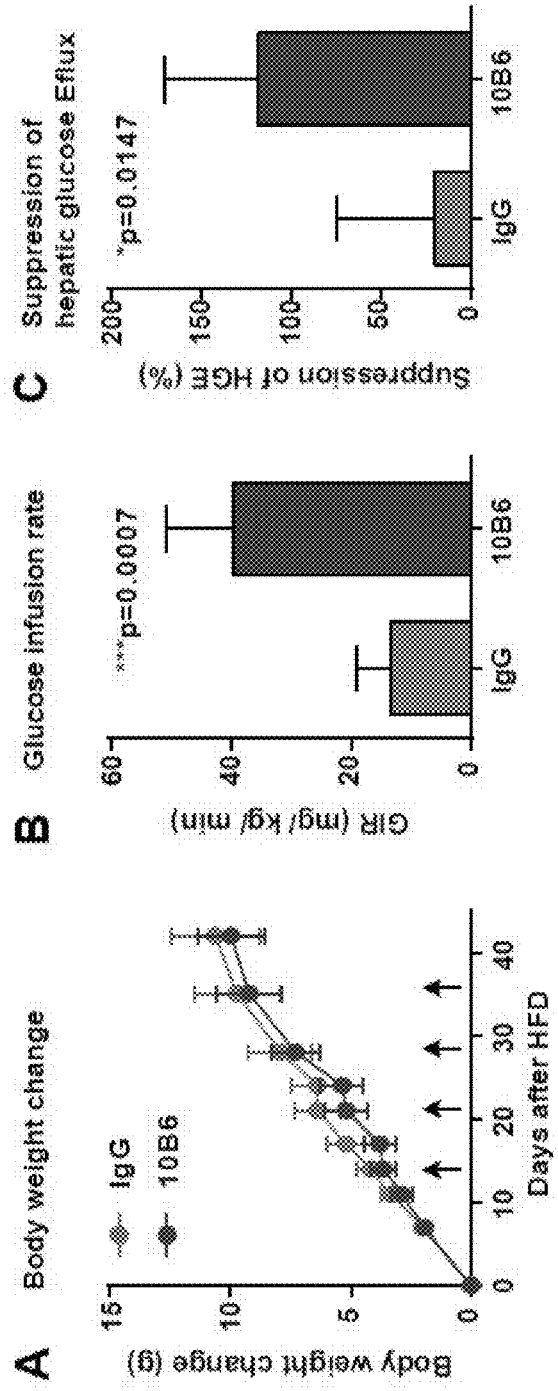
FIGS. 24A-24D: Endotrophin neutralization improves the metabolic phenotype.

To evaluate the therapeutic potential of endotrophin neutralizing monoclonal antibodies on metabolic perspectives, diet induced obese (DIO) mice were chronically treated with either IgG control or 10B6 (rat anti-mouse endotrophin monoclonal antibody) via intraperitoneal injection at 2 weeks after high-fat diet (HFD) challenge and maintained them on a HFD with antibody treatment for another 4 weeks. Body weight was comparable between two groups (IgG and 10B6) over the antibody treatment (FIG. 24A). To examine the effects of endotrophin neutralization on insulin sensitivity, hyperinsulinemic-euglycemic clamps were performed on DIO mice given either IgG or 10B6. Strikingly, 10B6 treated DIO mice improved whole-body insulin sensitivity, as determined by the amount of glucose required to maintain euglycemia (FIG. 24B) and by the amount of suppression of hepatic glucose efflux (FIGS. 24C and D).

The Levels of Endotrophin in Adipose Tissues are Negatively Correlated with Insulin Sensitivity in Obese Human Patients.

Figure 25:
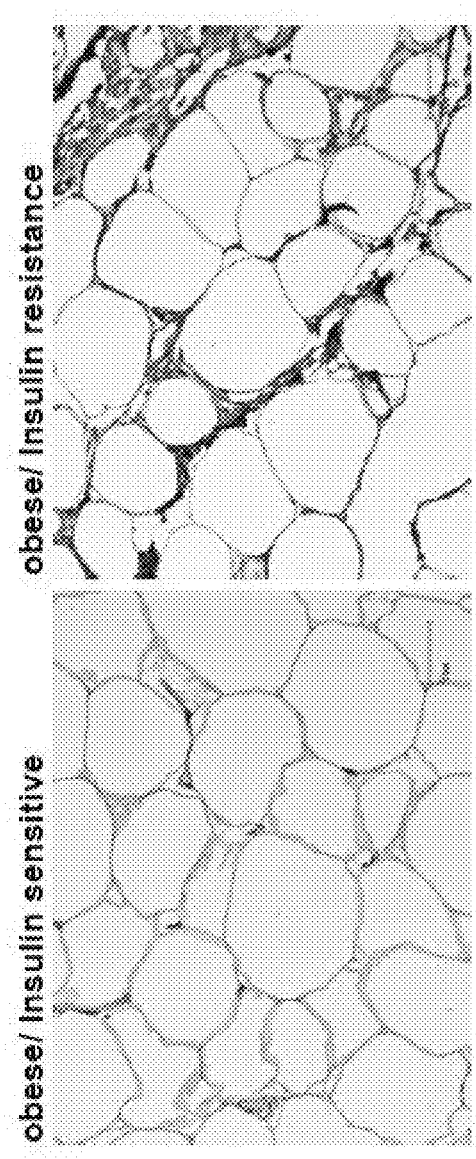
FIG. 25: Endotrophin is upregulated in obese, insulin resistant human fat tissue, but not in obese insulin sensitive fat tissue. Human mesenteric adipose tissue biopsies from healthy obese and insulin resistant obese patients were immune-decorated with an anti-human endotrophin antibody.

Endotrophin immunostaining for human mesenteric adipose tissues shows that endotrophin is upregulated mostly as a function of insulin sensitivity, not so much as a mere consequence of obesity (FIG. 25).

Neutralization of Endotrophin Activities in Diet Induced Obese Mice Improves Serum and Hepatic Lipid Parameters.

Figures 26A, 26B, 26C, 26D, 26E, 26F, 26G:
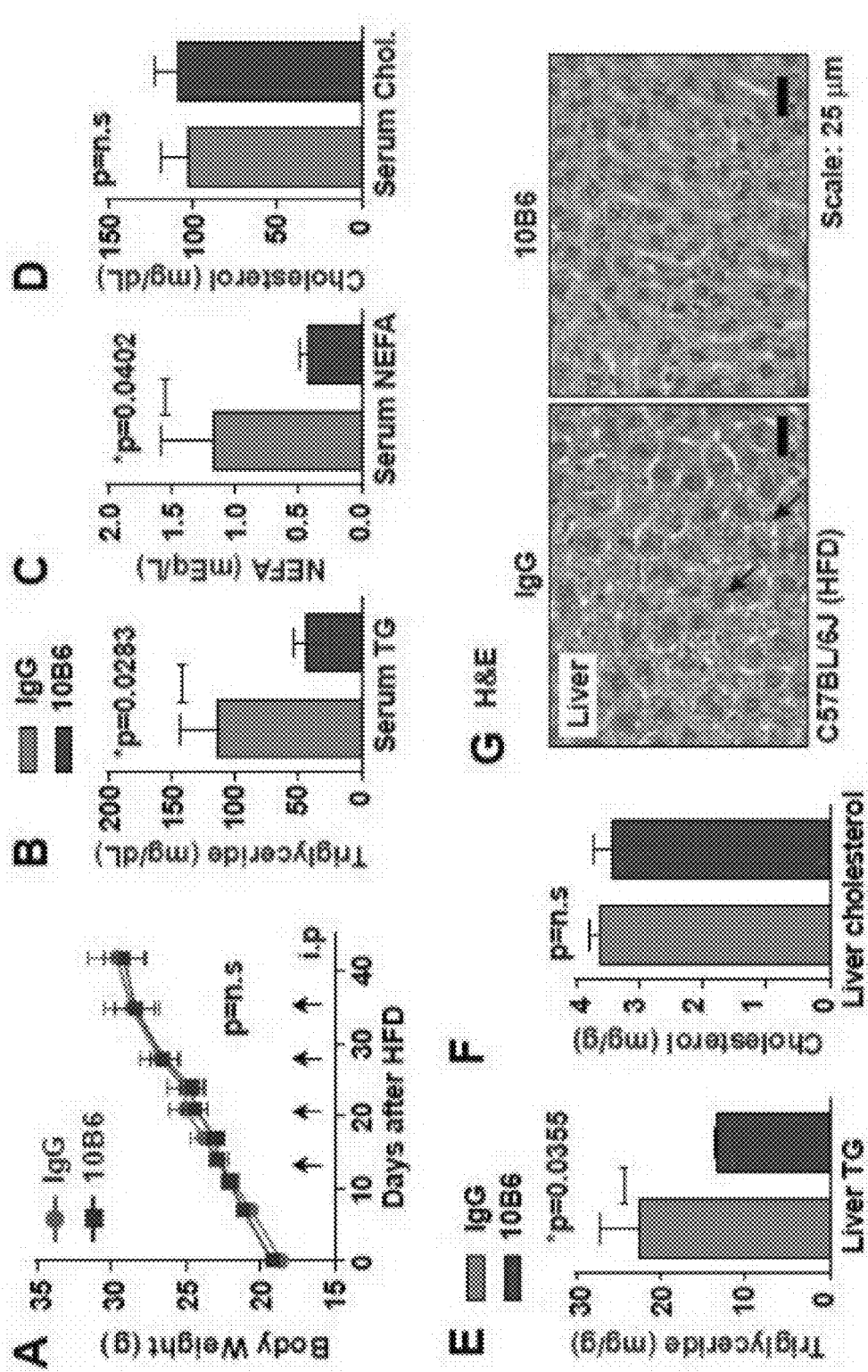
FIGS. 26A-26G: Endotrophin neutralization improves the metabolic phenotype.

To evaluate the therapeutic potential of endotrophin neutralizing monoclonal antibodies on lipid parameters, a separate cohort of diet induced obese (DIO) mice were chronically treated with either IgG control or 10B6 (rat anti-mouse endotrophin monoclonal antibody) via intraperitoneal injection at 2 weeks after high-fat diet (HFD) challenge and maintained them on a HFD with antibody treatment for another 4 weeks, similar to the experiment described in FIG. 24. Body weight was comparable between two groups (IgG and 10B6) over the antibody treatment (FIG. 26A). DIO mice given 10B6 display dramatically improved the levels of serum triglyceride (FIG. 26B) and free fatty acids (FIG. 26C) whereas the serum cholesterol levels were less affected by endotrophin neutralization (FIG. 26D). Additionally, the levels of hepatic triglycerides (FIG. 26E) were also improved whereas the cholesterol levels were comparable between two groups (FIG. 26F). Histological analysis with H&E stains indicates that hepatic lipid accumulation in DIO mice was significantly reduced in the presence of 10B6 compared to IgG control (FIG. 26G).

Collectively, these data on 10B6 treated DIO mice suggest that endotrophin neutralization improves metabolic profiles, such as the levels of circulating triglycerides and free fatty acids, reduces hepatic triglyceride levels and also improves systemic insulin sensitivity by reducing hepatic glucose output. Thus, anti-endotrophin agents (e.g., antibodies or fragments thereof as discussed above) can be used to treat various metabolic disorders-related diseases (e.g., diabetes and obesity).

EQUIVALENTS

The present invention provides among other things novel antibodies and methods for use in cancer therapeutics. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and sequence database entries mentioned herein are hereby incorporated by reference in their entirety as if each individual publication or patent was specifically and individually indicated to be incorporated by reference.

REFERENCES

U.S. Pat. Nos. 3,817,837; 3,850,752; 3,996,345; 4,277,437; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024

U.S. Patent Application Nos. 2004/0126828 and 2002/0172677

Arumugam T, Ramachandran V, Fournier K F, Wang H, Marquis L, Abbruzzese J L, Gallick G E, Logsdon C D, McConkey D J, Choi W (2009) Epithelial to mesenchymal transition contributes to drug resistance in pancreatic cancer. *Cancer Res* 69: 5820-5828

Blanquicett C, Roman J, Hart C M (2008) Thiazolidinediones as anti-cancer agents. *Cancer Ther* 6: 25-34

Bonaldo P, Braghetta P, Zanetti M, Piccolo S, Volpin D, Bressan G M (1998) Collagen V I deficiency induces early onset myopathy in the mouse: an animal model for Bethlem myopathy. *Hum Mol Genet* 7: 2135-2140

Burstein H J, Demetri G D, Mueller E, Sarraf P, Spiegelman B M, Winer E P (2003) Use of the peroxisome proliferator-*activated receptor* (PPAR) gamma ligand troglitazone as treatment for refractory breast cancer: a phase II study. *Breast Cancer Res Treat* 79: 391-397

Dangi-Garimella S, Krantz S B, Barron M R, Shields M A, Heiferman M J, Grippo P J, Bentrem D J, Munshi H G (2011) Three-dimensional collagen I promotes gemcitabine resistance in pancreatic cancer through MT1-MMP-mediated expression of HMGA2. *Cancer Res* 71: 1019-1028

Galluzzi L, Senovilla L, Vitale I, Michels J, Martins I, Kepp O, Castedo M, Kroemer G (2012) Molecular mechanisms of cisplatin resistance. *Oncogene* 31: 1869-1883

Girnun G D, Chen L, Silvaggi J, Drapkin R, Chirieac L R, Padera R F, Upadhyay R, Vafai S B, Weissleder R, Mahmood U, Naseri E, Buckley S, Li D, Force J, McNamara K, Demetri G, Spiegelman B M, Wong K K (2008) Regression of drug-resistant lung cancer by the combination of rosiglitazone and carboplatin. *Clin Cancer Res* 14: 6478-6486

Girnun G D, Naseri E, Vafai S B, Qu L, Szwaya J D, Bronson R, Alberta J A, Spiegelman B M (2007) Synergy between PPARgamma ligands and platinum-based drugs in cancer. *Cancer Cell* 11: 395-406

Guy C T, Cardiff R D, Muller W J (1992) Induction of mammary tumors by expression of polyomavirus middle T oncogene: a transgenic mouse model for metastatic disease. *Mol Cell Biol* 12: 954-961

Haslehurst A M, Koti M, Dharsee M, Nuin P, Evans K, Geraci J, Childs T, Chen J, Li J, Weberpals J, Davey S, Squire J, Park P C, Feilotter H (2012) EMT transcription factors snail and slug directly contribute to cisplatin resistance in ovarian cancer. *BMC Cancer* 12: 91

Helleman J, Jansen M P, Ruigrok-Ritstier K, van Staveren I L, Look M P, Meijer-van Gelder M E, Sieuwerts A M, Klijn J G, Sleijfer S, Foekens J A, Berns E M (2008) Association of an extracellular matrix gene cluster with breast cancer prognosis and endocrine therapy response. *Clin Cancer Res* 14: 5555-5564

Iyengar P, Espina V, Williams T W, Lin Y, Berry D, Jelicks L A, Lee H, Temple K, Graves R, Pollard J, Chopra N, Russell R G, Sasisekharan R, Trock B J, Lippman M, Calvert V S, Petricoin E F, 3rd, Liotta L, Dadachova E, Pestell R G, Lisanti M P, Bonaldo P, Scherer P E (2005) Adipocyte-derived collagen VI affects early mammary tumor progression in vivo, demonstrating a critical interaction in the tumor/stroma microenvironment. *J Clin Invest* 115: 1163-1176

Jean C, Gravelle P, Fournie J J, Laurent G (2011) Influence of stress on extracellular matrix and integrin biology. *Oncogene* 30: 2697-2706

Kelland L (2007) The resurgence of platinum-based cancer chemotherapy. *Nat Rev Cancer* 7: 573-584

Khan T, Muise E S, Iyengar P, Wang Z V, Chandalia M, Abate N, Zhang B B, Bonaldo P, Chua S, Scherer P E (2009) Metabolic dysregulation and adipose tissue fibrosis: role of collagen V I. *Mol Cell Biol* 29: 1575-1591

Kulke M H, Demetri G D, Sharpless N E, Ryan D P, Shivdasani R, Clark J S, Spiegelman B M, Kim H, Mayer R J, Fuchs C S (2002) A phase II study of troglitazone, an activator of the PPARgamma receptor, in patients with chemotherapy-resistant metastatic colorectal cancer. *Cancer J* 8: 395-399

Landskroner-Eiger S, Qian B, Muise E S, Nawrocki A R, Berger J P, Fine E J, Koba W, Deng Y, Pollard J W, Scherer P E (2009) Proangiogenic contribution of adiponectin toward mammary tumor growth in vivo. *Clin Cancer Res* 15: 3265-3276

Latifi A, Abubaker K, Castrechini N, Ward A C, Liongue C, Dobill F, Kumar J, Thompson E W, Quinn M A, Findlay J K, Ahmed N (2011) Cisplatin treatment of primary and metastatic epithelial ovarian carcinomas generates residual cells with mesenchymal stem cell-like profile. *J Cell Biochem* 112: 2850-2864

Lee Y J, Doliny P, Gomez-Fernandez C, Powell J, Reis I, Hurley J (2004) Docetaxel and cisplatin as primary chemotherapy for treatment of locally advanced breast cancers. *Clin Breast Cancer* 5: 371-376

Mueller E, Sarraf P, Tontonoz P, Evans R M, Martin K J, Zhang M, Fletcher C, Singer S, Spiegelman B M (1998) Terminal differentiation of human breast cancer through PPAR gamma. *Mol Cell* 1: 465-470

Netti P A, Berk D A, Swartz M A, Grodzinsky A J, Jain R K (2000) Role of extracellular matrix assembly in interstitial transport in solid tumors. *Cancer Res* 60: 2497-2503

Palakurthi S S, Aktas H, Grubissich L M, Mortensen R M, Halperin J A (2001) Anticancer effects of thiazolidinediones are independent of peroxisome proliferator-activated receptor gamma and mediated by inhibition of translation initiation. *Cancer Res* 61: 6213-6218

Park J, Kusminski C M, Chua S C, Scherer P E (2010) Leptin receptor signaling supports cancer cell metabolism through suppression of mitochondrial respiration in vivo. *Am J Pathol* 177: 3133-3144

Park J, Scherer P E (2012a) Adipocyte-derived endotrophin promotes malignant tumor progression. *J Clin Invest* 122: 4243-4256

Park J, Scherer P E (2012b) Endotrophin—a Novel Factor Linking Obesity with Aggressive Tumor Growth. *Oncotarget* 3: 1487-1488

Pulaski B A, Ostrand-Rosenberg S (1998) Reduction of established spontaneous mammary carcinoma metastases following immunotherapy with major histocompatibility complex class II and B7.1 cell-based tumor vaccines. *Cancer Res* 58: 1486-1493

Reka A K, Kurapati H, Narala V R, Bommer G, Chen J, Standiford T J, Keshamouni V G (2010) Peroxisome proliferator-activated receptor-gamma activation inhibits tumor metastasis by antagonizing Smad3-mediated epithelial-mesenchymal transition. *Mol Cancer Ther* 9: 3221-3232

Rintoul R C, Sethi T (2001) The role of extracellular matrix in small-cell lung cancer. *Lancet Oncol* 2: 437-442

Rosano L, Cianfrocca R, Spinella F, Di Castro V, Nicotra M R, Lucidi A, Ferrandina G, Natali P G, Bagnato A (2011) Acquisition of chemoresistance and EMT phenotype is linked with activation of the endothelin A receptor pathway in ovarian carcinoma cells. *Clin Cancer Res* 17: 2350-2360

Saez E, Rosenfeld J, Livolsi A, Olson P, Lombardo E, Nelson M, Banayo E, Cardiff R D, Izpisua-Belmonte J C, Evans R M (2004) PPAR gamma signaling exacerbates mammary gland tumor development. *Genes Dev* 18: 528-540

Satoh T, Toyoda M, Hoshino H, Monden T, Yamada M, Shimizu H, Miyamoto K, Mori M (2002) Activation of peroxisome proliferator-activated receptor-gamma stimulates the growth arrest and DNA-damage inducible 153 gene in non-small cell lung carcinoma cells. *Oncogene* 21: 2171-2180

Sethi T, Rintoul R C, Moore S M, MacKinnon A C, Salter D, Choo C, Chilvers E R, Dransfield I, Donnelly S C, Strider R, Haslett C (1999) Extracellular matrix proteins protect small cell lung cancer cells against apoptosis: a mechanism for small cell lung cancer growth and drug resistance in vivo. *Nat Med* 5: 662-668

Sherman-Baust C A, Weeraratna A T, Rangel L B, Pizer E S, Cho K R, Schwartz D R, Shock T, Morin P J (2003) Remodeling of the extracellular matrix through overexpression of collagen V I contributes to cisplatin resistance in ovarian cancer cells. *Cancer Cell* 3: 377-386

Shields M A, Dangi-Garimella S, Redig A J, Munshi H G (2012) Biochemical role of the collagen-rich tumour microenvironment in pancreatic cancer progression. *Biochem J* 441: 541-552

Sirohi B, Arnedos M, Popat S, Ashley S, Nerurkar A, Walsh G, Johnston S, Smith I E (2008) Platinum-based chemotherapy in triple-negative breast cancer. *Ann Oncol* 19: 1847-1852

Smith M R, Manola J, Kaufman D S, George D, Oh W K, Mueller E, Slovin S, Spiegelman B, Small E, Kantoff P W (2004) Rosiglitazone versus placebo for men with prostate carcinoma and a rising serum prostate-specific antigen level after radical prostatectomy and/or radiation therapy. *Cancer* 101: 1569-1574

Su C, Su B, Tang L, Zhao Y, Zhou C (2007) Effects of collagen iv on cisplatin-induced apoptosis of non-small cell lung cancer cells. *Cancer Invest* 25: 542-549

Theocharis S E, Margeli A P, Koutselinis A (2003) Metallothionein: a multifunctional protein from toxicity to cancer. *Int J Biol Markers* 18: 162-169

Tikoo K, Kumar P, Gupta J (2009) Rosiglitazone synergizes anticancer activity of cisplatin and reduces its nephrotoxicity in 7, 12-dimethyl benz {a} anthracene (DMBA) induced breast cancer rats. *BMC Cancer* 9: 107

Tontonoz P, Spiegelman B M (2008) Fat and beyond: the diverse biology of PPARgamma. *Annu Rev Biochem* 77: 289-312

Varma R R, Hector S M, Clark K, Greco W R, Hawthorn L, Pendyala L (2005) Gene expression profiling of a clonal isolate of oxaliplatin-resistant ovarian carcinoma cell line A2780/C10. *Oncol Rep* 14: 925-932

Zhu K, Chen L, Han X, Wang J (2012) Short hairpin RNA targeting Twist1 suppresses cell proliferation and improves chemosensitivity to cisplatin in HeLa human cervical cancer cells. *Oncol Rep* 27: 1027-1034

The invention claimed is:

1. A monoclonal antibody, or fragment thereof, that specifically binds to the C5 domain of the alpha3 chain of human collagen VI (SEQ ID NO: 5) or mouse collagen VI (SEQ ID NO: 6), wherein the antibody comprises:
   (a) a first $V_H$ CDR comprising the sequence GYTFTSYE (SEQ ID NO: 9);
   (b) a second $V_H$ CDR comprising the sequence IYPESGST (SEQ ID NO: 10);
   (c) a third $V_H$ CDR comprising the sequence TRGLRVLGYVMDV (SEQ ID NO: 11);
   (d) a first $V_L$ CDR comprising the sequence QNINKY (SEQ ID NO: 7);
   (e) a second $V_L$ CDR comprising the sequence NTN; and
   (f) a third $V_L$ CDR comprising the sequence LQHSSLYT (SEQ ID NO: 8).

2. The monoclonal antibody, or fragment thereof, of claim 1, further comprising a light chain framework sequence from an immunoglobulin light chain- and a heavy chain framework sequence from an immunoglobulin heavy chain.

3. The monoclonal antibody, or fragment thereof, of claim 2, comprising: i) the light chain variable region with the amino acid sequence of SEQ ID NO: 2; and ii) the heavy chain variable region with the amino acid sequence of SEQ ID NO: 4.

4. The monoclonal antibody, or fragment thereof, of claim 1, wherein the antibody is recombinant.

5. The monoclonal antibody, or fragment thereof, of claim 1, wherein the antibody is conjugated or fused to an imaging agent or a cytotoxic agent.

6. The monoclonal antibody, or fragment thereof, of claim 1, wherein the antibody is a Fab', a F(ab')2, a F(ab')3, a monovalent scFv, a bivalent scFv, or a single domain antibody.

7. The monoclonal antibody, or fragment thereof, of claim 1, wherein the antibody is a human, humanized antibody or de-immunized antibody.

8. A method of treating a cancer patient comprising administering an effective amount of an antibody in accordance with claim 1, said cancer patient determined to express an elevated level of endotrophin relative to control patient.

9. The method of claim 8, further defined as a method for inhibiting angiogenesis or increasing chemosensitivity to platinum-based chemotherapy in the patient.

10. The method of claim 9, further comprising administering a platinum-based chemotherapy to the patient.

11. The method claim 8, wherein the cancer is a breast cancer or colon cancer.

12. The method of claim 8, wherein the antibody is conjugated or fused to an imaging agent or a cytotoxic agent.

13. The method of claim 8, further comprising administering at least a second anti-cancer therapy.

14. The method of claim 13, wherein the second anti-cancer therapy is a chemotherapy, radiotherapy, gene therapy, surgery, hormonal therapy, anti-angiogenic therapy or cytokine therapy.

15. The method of claim 14, wherein the chemotherapy comprises a platinum-based chemotherapy.

16. The method of claim 15, wherein the platinum-based chemotherapy is cisplatin, oxaliplatin or carboplatin.

17. The method of claim 15, further comprising administering thiazolidinedione to the patient.

* * * * *